US012799106B2

(12) United States Patent
Baati et al.

(10) Patent No.: US 12,799,106 B2
(45) Date of Patent: Nov. 17, 2026

(54) THIAZOLOXIME AND OXAZOLOXIME DERIVATIVES AS REACTIVATORS OF ORGANOPHOSPHOROUS NERVE AGENT (OPNA)-INHIBITED HUMAN ACETYLCHOLINESTERASE FOR THE TREATMENT OF NERVOUS AND/OR RESPIRATORY FAILURE AFTER INTOXICATION WITH OPNA

(71) Applicants: CENTRE NATIONAL DE LA RECHERCHE SCIENTIFIQUE, Paris (FR); UNIVERSITÉ DE STRASBOURG, Stasbourg (FR); ETAT FRANÇAIS REPRÉSENTÉ PAR LA DIRECTION CENTRALE DU SERVICE DE SANTÉ DES ARMEES, Paris (FR)

(72) Inventors: Rachid Baati, Strasbourg (FR); José Dias, Brétigny sur Orge (FR); Florian Nachon, Brétigny sur Orge (FR); Raymond Franck Razafindrainibe, Schiltigheim (FR); Mallikarjuna Reddy Nimmakayala, Strasbourg (FR); Camille Voros, Strasbourg (FR)

(73) Assignees: CENTRE NATIONAL DE LA RECHERCHE SCIENTIFIQUE (CNRS), Paris (FR); UNIVERSITÉ DE STRASBOURG, Strasbourg (FR); ETAT FRANÇAIS REPRÉSENTÉ PAR LA DIRECTION CENTRALE DU SERVICE DE SANTÉ DES ARMÉES, Paris (FR)

( * ) Notice: Subject to any disclaimer, the term of this patent is extended or adjusted under 35 U.S.C. 154(b) by 927 days.

(21) Appl. No.: 17/999,655

(22) PCT Filed: May 25, 2021

(86) PCT No.: PCT/EP2021/063826

§ 371 (c)(1),
(2) Date: Nov. 22, 2022

(87) PCT Pub. No.: WO2021/239695

PCT Pub. Date: Dec. 2, 2021

(65) Prior Publication Data

US 2023/0203024 A1 Jun. 29, 2023

(30) Foreign Application Priority Data

May 26, 2020 (EP) .................................. 20305545.4

(51) Int. Cl.

| | |
|---|---|
| ***C07D 413/06*** | (2006.01) |
| ***A61P 25/28*** | (2006.01) |
| ***C07D 277/28*** | (2006.01) |
| ***C07D 417/06*** | (2006.01) |
| ***C07D 417/12*** | (2006.01) |

(52) U.S. Cl.

CPC ............ *C07D 417/06* (2013.01); *A61P 25/28* (2018.01); *C07D 277/28* (2013.01); *C07D 413/06* (2013.01); *C07D 417/12* (2013.01)

(58) Field of Classification Search

CPC .......... A61P 25/28; A61P 35/00; A61P 39/00; A61P 39/02; C07D 277/28; C07D 413/06; C07D 413/08; C07D 417/06; C07D 417/08; C07D 417/12

See application file for complete search history.

(56) References Cited

FOREIGN PATENT DOCUMENTS

| | | | |
|---|---|---|---|
| WO | 2007/047306 | A1 | 4/2007 |
| WO | 2015/057822 | A1 | 4/2015 |
| WO | 2018/187553 | A1 | 10/2018 |

OTHER PUBLICATIONS

Kovarik et al: "Reversal of Tabun Toxicity Enabled by a Triazole-Annulated Oxime Library-Reactivators pf Acetylcholinesterase", Chemistry—A European Journal, vol. 25, No. 16, p. 4100-4114, Nov. 20, 2018.
Katz et al, ChemBioChem. 2015, 16, 2205-2215.
de Koning et al, Eur. J. Med. Chem. 2018, 157,151-160.
Cadieux et al, Chemico-Biological Interactions 2016, 259, 133-141.
Yerri et al. Eur. J. Med .Chem. 2018, 4161-4165.
Zueva I, Dias J, Lushchekina S, et al. New evidence for dual binding site inhibitors of acetylcholinesterase as improved drugs for treatment of Alzheimer's disease. Neuropharmacology. 2019; 155:131-141. doi: 10.1016/j.neuropharm.2019.05.025.
Carletti, E. et al. 2008.
Ellman, G.L., et al. 1961.
Kitz, R.J., et 10 al. 1965.
Worek, F., et al., 2004.

*Primary Examiner* — Kara R. Mcmillian
*Assistant Examiner* — Sophia P Hirakis
(74) *Attorney, Agent, or Firm* — WCF IP

(57) ABSTRACT

The present invention relates to a compound of formula (I). It also relates to a pharmaceutical composition comprising at least one compound of formula (I) and at least one pharmaceutically acceptable support. Finally, it relates to the compounds of formula (I) for use in a method of medical treatment, preferably in the treatment of a nervous and/or respiratory failure due to intoxication with at least one organo-phosphorous nerve agent (OPNA); in the treatment of neurological diseases such as Alzheimer's disease; and/or in the treatment of cancer. The compounds act as reactivators of OPNA-inhibited hAChE (human acetylcholinesterase).

(I)

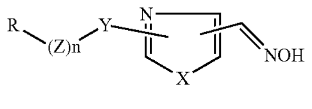

11 Claims, No Drawings

THIAZOLOXIME AND OXAZOLOXIME DERIVATIVES AS REACTIVATORS OF ORGANOPHOSPHOROUS NERVE AGENT (OPNA)-INHIBITED HUMAN ACETYLCHOLINESTERASE FOR THE TREATMENT OF NERVOUS AND/OR RESPIRATORY FAILURE AFTER INTOXICATION WITH OPNA

The present invention relates to novel compounds having a thiazoloxime or oxazoloxime scaffold. Such compounds may be useful for many therapeutic and non-therapeutic applications. The invention also relates to compositions, notably pharmaceutical compositions, comprising said compounds, and their use.

Organophosphorous nerve agents (OPNA) are extremely toxic compounds that comprise chemical warfare agents (CWA) including sarin, soman, cyclosarin, tabun, methylphosphonothioate (VX) and pesticides such as paraoxon, parathion and tetraethyl pyrophosphate (TEPP). Their acute toxicity results from the irreversible inhibition of acetylcholinesterase (AChE) through phosphylation of its catalytic serine, which results in the inability of the enzyme to hydrolyze acetylcholine (ACh). Accumulation of this neurotransmitter at cholinergic synapses occurs, leading to a permanent saturation of the muscarinic and nicotinic receptors which ultimately results in seizure and respiratory arrest. Depending on the class of OPNA and on the administrated dose, death can occur within a few minutes.

Due to the similarity between the chemical precursors of CWA and pesticides, and to the relatively simple chemistry involved in their synthesis, efforts to control the proliferation of these agents have proved of limited success. Therefore, the development of effective measures to counteract OPNA poisoning remains a challenging issue to protect and treat both civilian and military populations. The current treatment for OPNA poisoning consists in the administration of a combination of atropine (antimuscarinic agent) and diazepam (anticonvulsant drug), to limit convulsions, and of a standard pyridinium oxime (pralidoxime, trimedoxime, HI-6, obidoxime, or HL6-7) to reactivate AChE. Oximes exert their action on OPNA-inhibited AChE by attacking the phosphorous atom of the phosphylated serine, leading to the removal of the phosphonate and restoration of the enzyme's catalytic activity. However, it has been demonstrated that the current therapy results in unequal efficiency, and none of these oximes offer broad efficacy across the different OPNAs. Further limitations of oxime-based therapy include inability to cross the blood-brain barrier (BBB), inability to reactivate the "aged" enzyme, and rapid clearance from the circulation when tested in vivo. Animal model studies and recent clinical trials using pesticide poisoned individuals have shown uneven clinical benefits of these oximes, and even harm, so their true efficacy as antidotes has been debated at the World Health Organisation.

To overcome the disadvantages of the current medication, the development of new broad spectrum and bioavailable centrally active drugs is of crucial importance.

Over the past decades, there has been a growing interest in the development of non-ionic oximes reactivators of OPNA-inhibited hAChE (human AChE) to increase BBB permeability. For example, uncharged hybrid reactivators bearing 3-hydroxy-2-pyridinaldoxime as nucleophilic moiety and a peripheral site AChE ligand, exhibited increased affinity for the phosphylated enzyme, a large spectrum of reactivation and the ability to cross efficiently the BBB in vitro. Beside these discoveries, others heterocyclic, aromatic and acyclic nucleophilic oximes, as well as uncharged acetamido bis-oximes have been developed as antidotes, with more or less success in the reactivation of OPNA-inhibited AChE.

Recently, unusual non-oxime non-ionic new functional groups such as Mannich phenols that are capable of reactivating OPNA-inhibited AChE have been reported by Katz, Cadieux and De Koning (Katz et al, *ChemBioChem.* 2015, 16, 2205-2215; de Koning et al, *Eur. J. Med. Chem.* 2018, 157, 151-160; Cadieux et al, *Chemico-Biological Interactions* 2016, 259, 133-141). However, the mechanism of the reactivation is still unclear, and the development of these molecules is hampered by their low stability in biological media.

Recent findings have demonstrated the ability of a zwitterionic, centrally acting, brain penetrating oxime to reverse severe symptoms and rapidly reactivate sarin- and paraoxon inhibited AChE in vivo.

It is further obvious that the above-mentioned compounds are accessed only after tedious, non-flexible and lengthy multistep chemical synthesis due to their increased structural complexity.

Despite these innovative strategies for the development of reactivators, efforts towards shorter and more convergent synthetic routes to innovative broad spectrum and centrally effective antidotes are still needed. There is thus a remaining need for chemical compounds efficient in therapeutic applications, particularly against OPNA intoxications, with a broad spectrum and centrally effective. These compounds have to be quick and easy to synthetize.

Surprisingly, the inventors have now discovered that specific compounds, having a thiazoloxime or an oxazoloxime scaffold, fulfill these needs.

Indeed, such compounds are quick and very easy to produce thanks to a late-stage Sonogashira cross-coupling reaction of bromothiazoloximes isomers, which leads to a short and expedient synthesis, without using protecting groups for the sensitive oximes. The compounds present very interesting properties: they have a low molecular weight, and exhibit a quite simple molecular structural design and a broad spectrum of reactivation of OPNA-inhibited AChE, especially with increased efficacy for VX and paraoxon, and a good potency against sarin.

Notably, these compounds may be used as antidotes against OPNA intoxications or as detoxifying or decontamination agents against organophosphorus compounds, thanks to their effective and fast reactivation of hAChE without denaturing the same. They may also be used in the treatment of neurodegenerative diseases such as Alzheimer's disease. Finally, particularly the oxime compounds of the invention may be used as histone deacetylases (HDAC) inhibitors; consequently, they may be used in the treatment of cancer.

Thus, a first object of the present invention is a compound of formula (I):

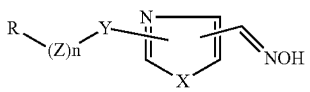

(I)

wherein the different groups are as defined in the detailed description below.

Another object of the present invention is a process for preparing the compounds of formula (I), especially by a Sonogashira reaction, as detailed below.

Another object of the present invention is a pharmaceutical composition comprising at least one compound of formula (I) and at least one pharmaceutically acceptable support.

Another object of the invention is a compound according to the invention, for use as a medicine.

A further object of the invention is a compound according to the invention for use in the treatment of a nervous and/or respiratory failure due to intoxication with at least one organophosphorous nerve agent.

Still a further object of this invention is a compound according to the invention for use in the treatment of neurological diseases such as Alzheimer's disease.

Still a further object of this invention is a compound according to the invention for use in the treatment of cancer.

A first object of the present invention is a compound of formula (I), or one of its pharmaceutically acceptable salts:

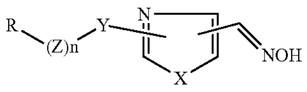

(I)

wherein:

X is O or S;

Y is $-CH_2-CH_2-$, $-C\equiv C-$ or $-CH=CH-$;

Z is $-CH_2-$, n is an integer from 0 to 4; and

R is an alkyl group, a hydroxyalkyl group, an alkyl group ended by a radical —C(=O)—O—CH3, an aryl, a heteroaryl, a cycloalkyl, a heterocyclyl, a biomolecule, a fluorescent probe, or a group —N(R1)(R2), wherein R1 and R2 are each independently H, an alkyl group, an aryl, a heteroaryl or a cycloalkyl.

When X is O, then formula (I) is an oxazoloxime scaffold.

When X is S, then formula (I) is a thiazoloxime scaffold.

By "pharmaceutically acceptable salt", it is meant any salt of a compound of formula (I) with an acid or a base. Preferably, the pharmaceutically acceptable salt is a chlorhydrate salt. Such a salt may be obtained by using HCl. More preferably, the heteroaryl group of R is a nitrogen atom, which is complexed with HCl.

Preferably, the compound of the invention is a salt of a compound of formula (I), more preferably a chlorhydrate salt of a compound of formula (I).

The compound of formula (I) may be labeled with one or more isotopes such as $^{15}N$, $^{18}O$, $^{2}H$ or $^{3}H$. Preferably the compound is labeled on the =N—OH group, with $^{15}N$. Indeed, such a stable, non-toxic and non-radioactive isotope would allow in vivo and in vitro biological studies.

By "alkyl", it is meant a linear hydrocarbon group preferably comprising from 1 to 20 carbon atoms, in particular from 1 to 15 carbon atoms, preferably from 2 to 6 carbon atoms (C2-C6 group) or a branched or cyclic hydrocarbon group comprising from 3 to 20 carbon atoms. Examples of alkyl groups include methyl, ethyl, n-propyl, isopropyl, n-butyl, isobutyl, tert-butyl, n-pentyl, isopentyl, n-hexyl, n-tridecyl, cyclohexyl and cyclohexylmethyl groups, and preferably ethyl, propyl, n-hexyl, n-tridecyl, cyclohexyl or cyclohexylmethyl group. Preferably, the alkyl group is a C2-C6 group or cyclohexylmethyl. Of course, the alkyl is not substituted.

By "hydroxyalkyl", it is meant an alkyl group substituted by at least one hydroxyl group (—OH). Preferably, the hydroxyalkyl group is a monohydroxyalkyl group, preferably a C2-C6 alkyl group substituted by one hydroxyl group. Preferably, the hydroxyalkyl group is methylhydroxy.

By "alkyl group ended by a radical —C(=O)—O—CH3", it is preferably meant a C2-C6 alkyl group ended by a radical —C(=O)—O—CH3. Preferably, the alkyl group ended by a radical —C(=O)—O—CH3 is —(CH2)3-C(=O)—O—CH3.

By "aryl", it is meant a monocyclic or polycyclic aromatic hydrocarbon group, which may be optionally substituted. Preferably, the aryl group is a phenyl, or a polycyclic aromatic hydrocarbon (PAH). A preferred PAH is pyrene. The aryl is preferably not substituted.

By "heteroaryl", it is meant an aryl group in which at least one carbon atom of the aromatic ring is substituted by a heteroatom, and which may be optionally substituted. The heteroatom may be nitrogen, oxygen, phosphorus or sulfur. Preferably the heteroatom is nitrogen. Examples of heteroaryl groups include pyridine, pyrrole, thiophene, furane, pyrimidine, pyrazine, pyridazine, triazole, tetrazine, triazine, imidazole, quinoline, thiazole, oxazole, tetrazole, oxadiazole, thiadiazole, and isoxazole groups. Preferably, the heteroaryl group is a pyridine group such as 2-, 3- or 4-pyridino, or a quinoline group such as a 4-quinolinyl, or a pyrimidine group such as a pyrimidin-2-yl. The heteroaryl is preferably not substituted.

A "cycloalkyl" is refers to a monocyclic or polycyclic saturated hydrocarbon group, which may be optionally substituted.

A "heterocyclyl" is refers to a monocyclic or polycyclic saturated hydrocarbon group in which at least one carbon atom of the ring is substituted by a heteroatom, and which may be optionally substituted. The heteroatom may be nitrogen, oxygen, or sulfur. Preferably, the heterocyclic group is morpholino, pyrazolidine, oxathiolane, tetrahydrofuran, dioxolane, piperidine, piperazine, thiomorpholine, tetrahydropyrane, oxetane or azetidine, such as 4-tetrahydropyrano or 3-oxetano or 3-azetidino. The heterocyclyl may be substituted or not.

By "biomolecule", it is meant a sugar moiety, a peptide moiety, an antibody, a virus, a DNA, a RNA or a protein moiety. The sugar moiety may be for example a glucose, fructose or sucrose moiety. A peptide moiety is a moiety typically comprising 1 to 50 amino acids. A protein moiety is a moiety typically comprising at least 51 amino acids, preferably from 60 to 500 amino acids.

By "fluorescent probe", it is meant a chemical function or a fluorophore endowed with fluorescent properties. The fluorescent moiety may be for example a fluoresceine, boron dipyrromethene (BODIPY), a coumarine, a cyanine, an Alexa Fluor, an acridine, a fluorone, a squaraine, a phenanthridine, a cyanine, an oxazine, a perylene, an anthracene or rhodamine moiety.

Preferably, R is an alkyl, a hydroxyalkyl group, an alkyl group ended by a radical —C(=O)—O—CH3, an aryl or a heteroaryl or a group —N(R1)(R2), wherein R1 and R2 are each independently H, an alkyl group, an aryl, a heteroaryl or a cycloalkyl.

Preferably, R is a heteroaryl or a group —N(R1)(R2), wherein R1 and R2 are each independently H or a heteroaryl. Preferably, the heteroaryl group is a pyridine group such as 2-, 3- or 4-pyridino, or a quinoline group such as a 4-quinolinyl.

Preferably, R is a pyridine group such as 2-, 3- or 4-pyridino.

Preferably, according to another embodiment, R is a group —N(R1)(R2), wherein R1 is H, and R2 is a heteroaryl, preferably a quinoline group such as a 4-quinolinyl.

Preferably, the —Y—(Z)n-R group is in position 2.

According to a first embodiment, preferably, the oxime group is in 4 position, and the compound of the invention is a 2-substituted-4-oxime-(oxazole or thiazole) of formula (II), or one of its pharmaceutically acceptable salts:

(II)

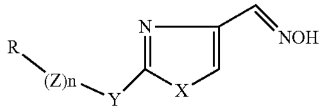

According to a second embodiment, preferably, the oxime group is in 5 position, and the compound of the invention is a 2-substituted-5-oxime-(oxazole or thiazole) of formula (III), or one of its pharmaceutically acceptable salts:

(III)

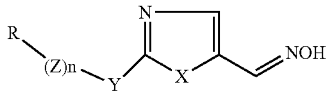

According to said first embodiment, it is preferred that the compound of formula (I) is a 2-substituted-4-oxime-(oxazole or thiazole) of formula (II), or one of its pharmaceutically acceptable salts:

(II)

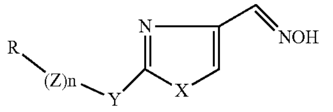

Preferably, X is S. In such a case, the compounds of formula (I) are 2-substituted-4-oxime-1,3-thiazoles.

X may also be O. In such a case, the compounds of formula (I) are 2-substituted-4-oxime-1,3-oxazoles.

Preferably, Y is —$CH_2$—$CH_2$— or —C≡C—, and n is 0, 1 or 2, preferably n is 0 or 2.

Preferably, R is a hydroxyalkyl group, an alkyl group ended by a radical —C(═O)—O—CH3, an aryl group, a heteroaryl or a group —N(R1)(R2). Preferably, the aryl is phenyl, and preferably is not substituted. Preferably, R is a heteroaryl or a group —N(R1)(R2).

Preferably said heteroaryl is not substituted. Preferably, said heteroaryl is a pyridine group such as 2-, 3- or 4-pyridino or a pyrimidine group such as a pyrimidin-2-yl. Preferably, said group —N(R1)(R2) is such that R1 is H, and R2 is a heteroaryl, preferably not substituted, preferably a quinoline group such as a 4-quinolinyl.

Preferably, according to said first embodiment, the compounds of formula (II) are such that:

X is S;

Y is —$CH_2$—$CH_2$— or —C≡C—, n is 0, 1 or 2, preferably n is 0 or 2; and

R is an alkyl, a hydroxyalkyl group, an alkyl group ended by a radical —C(═O)—O—CH3, an aryl group or a heteroaryl or a group —N(R1)(R2), preferably said alkyl is a C2-C6 group or cyclohexylmethyl, preferably said hydroxyalkyl group is methylhydroxy, preferably said alkyl group ended by a radical —C(═O)—O—CH3 is —(CH2)3-C(═O)—O—CH3, preferably said aryl is not substituted and is a phenyl or a polycyclic aromatic hydrocarbon such as a pyrene, preferably said heteroaryl is not substituted and is a pyridine group such as 2-, 3- or 4-pyridino or a pyrimidine group such as 2-pyrimidino; or R1 is H and R2 is a heteroaryl, preferably not substituted, preferably a quinoline group such as a 4-quinolinyl.

Preferably, according to said first embodiment, the compounds of formula (II) are also such that:

X is O;

Y is —$CH_2$—$CH_2$— or —C≡C—, n is 0, 1 or 2, preferably n is 0 or 2; and

R is a heteroaryl, preferably said heteroaryl is not substituted and is a pyridine group such as 2-, 3- or 4-pyridino.

Preferably, when Y is —$CH_2$—$CH_2$—, n is preferably 0 or 2, and R is a heteroaryl, preferably not substituted, and is a pyridine group such as 2-, 3- or 4-pyridino or a pyrimidine group such as 2-pyrimidino.

Preferably, the compound of formula (II) or one of its pharmaceutically acceptable salts is chosen from the following compounds:

4

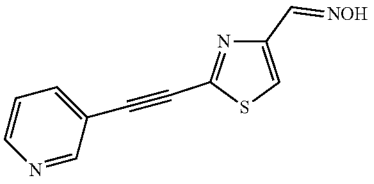

5

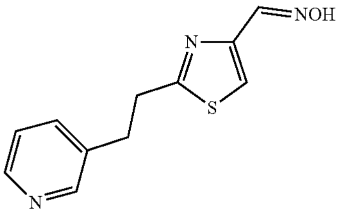

7

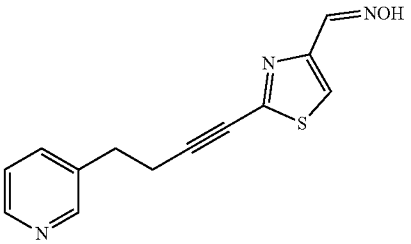

8

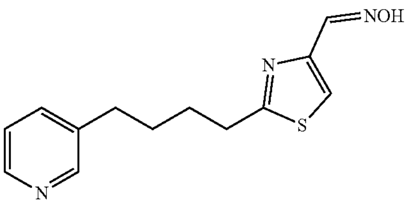

-continued
10
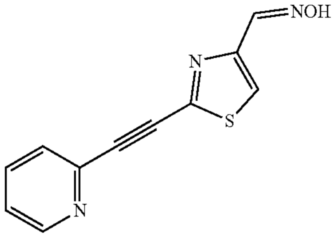
11
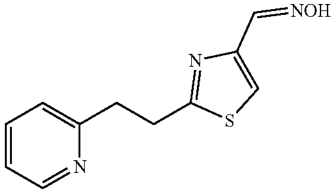
13
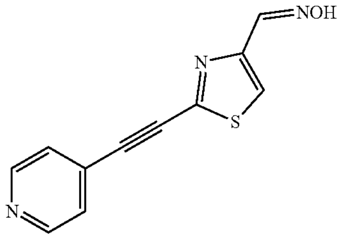
14
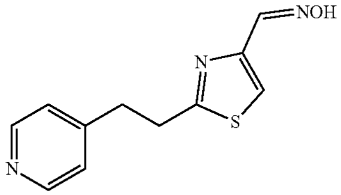
23
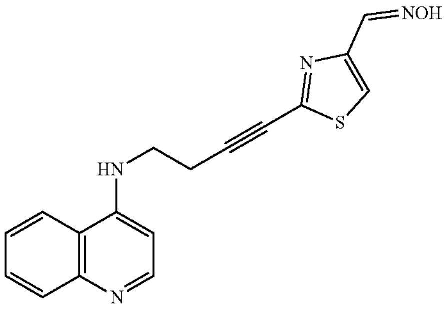
32
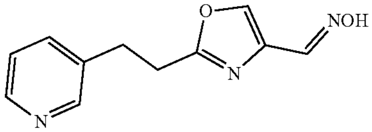
NM-55
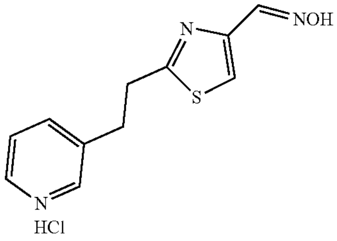
-continued
NM-131
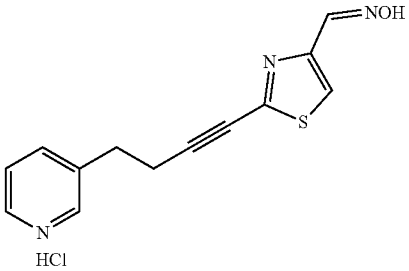
NM-132
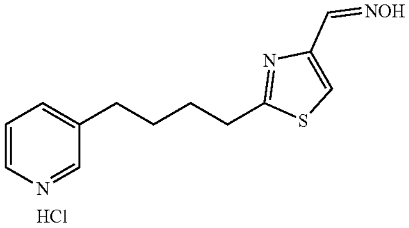
NM-109
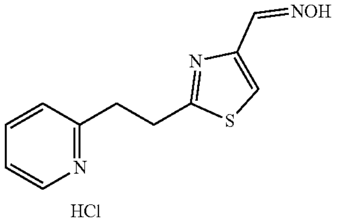
NM-130
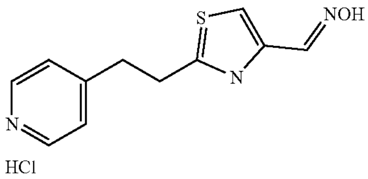
NM-46
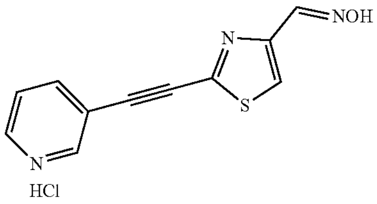
NM-168
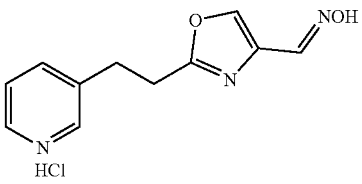

-continued
NM-176
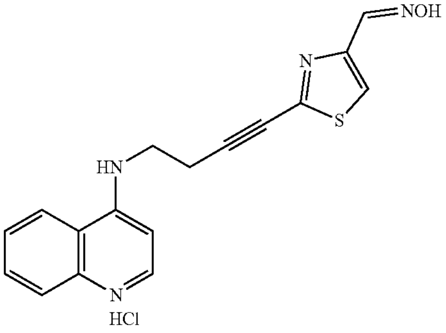
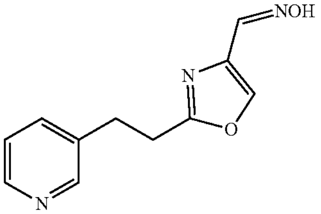
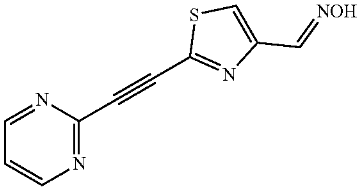
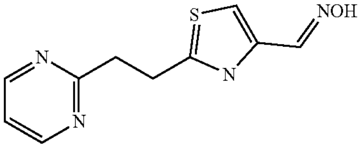
NM-250
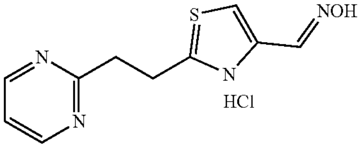
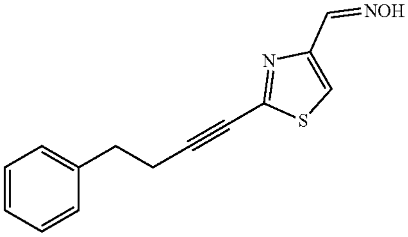
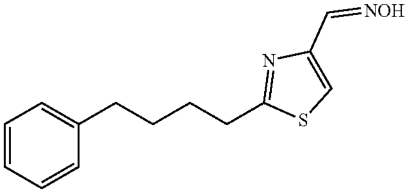
NM-247
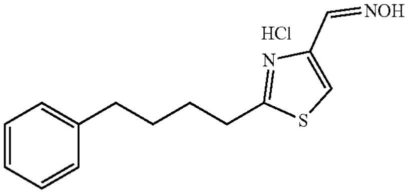
-continued
FR-72
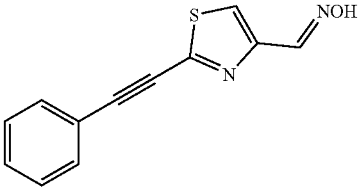
FR-74
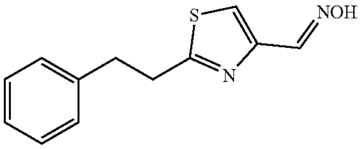
FR-78
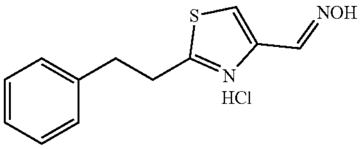
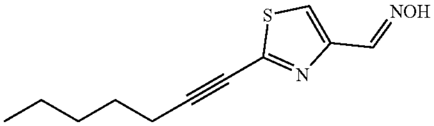
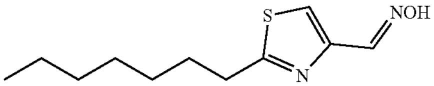
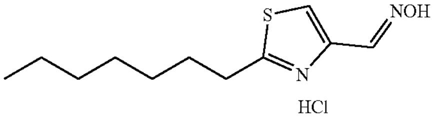
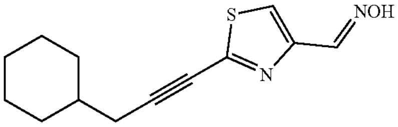
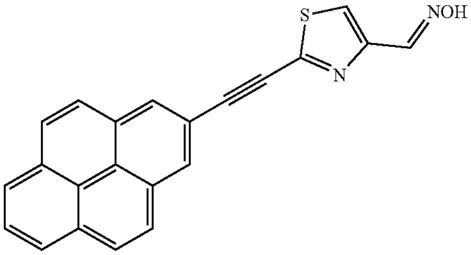
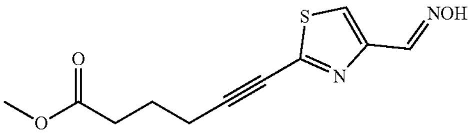
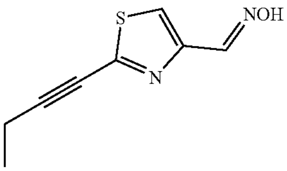

-continued

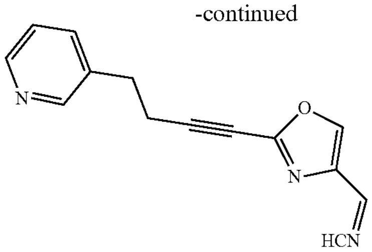

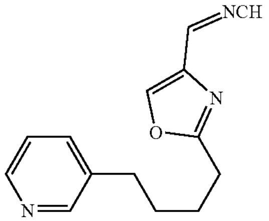

and

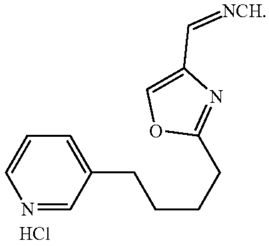

According to said second embodiment, it is preferred that the compound of formula (I) is a 2-substituted-5-oxime-(oxazole or thiazole) of formula (III):

(III)

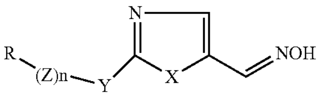

Preferably, X is S. In such a case, the compounds of formula (I) are 2-substituted-5-oxime-1,3-thiazoles.

X may also be O. In such a case, the compounds of formula (I) are 2-substituted-5-oxime-1,3-oxazoles.

Preferably, Y is —$CH_2$—$CH_2$— or —C≡C—, and n is 0, 1 or 2, preferably n is 0 or 2.

Preferably, R is a heteroaryl or a group —N(R1)(R2), wherein R1 and R2 are each independently H or a heteroaryl. Preferably said heteroaryl is not substituted. Preferably, said heteroaryl is a pyridine group such as 2-, 3- or 4-pyridino, or a quinoline group such as a 4-quinolinyl.

Preferably, R is a pyridine group such as 2-, 3- or 4-pyridino.

Preferably, according to another embodiment, R1 is H, and R2 is a heteroaryl, preferably a quinoline group such as a 4-quinolinyl.

Preferably, according to said second embodiment, the compounds of formula (III) are such that:

X is S;

Y is —$CH_2$—$CH_2$— or —C≡C—, n is 0, 1 or 2, preferably n is 0 or 2; and

R is a heteroaryl or a group —N(R1)(R2), preferably said heteroaryl is not substituted and is a pyridine group such as 2-, 3- or 4-pyridino; or R1 is H and R2 is a heteroaryl, preferably not substituted, preferably a quinoline group such as a 4-quinolinyl.

Preferably, according to said second embodiment, the compounds of formula (III) are also such that:

X is O;

Y is —$CH_2$—$CH_2$— or —C≡C—, n is 0, 1 or 2, preferably n is 0 or 2; and

R is a heteroaryl, preferably said heteroaryl is not substituted and is a pyridine group such as 2-, 3- or 4-pyridino.

Preferably, when Y is —$CH_2$—$CH_2$—, n is preferably 0 or 2, and R is a heteroaryl, preferably not substituted, and is a pyridine group such as 2-, 3- or 4-pyridino.

Preferably, the compound of formula (III) is chosen from the following compounds:

17

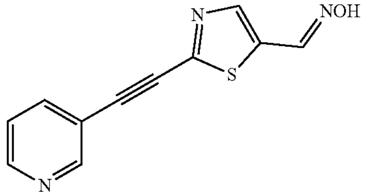

18

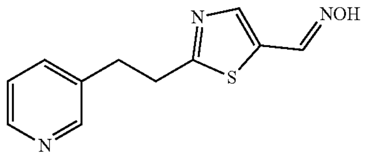

19

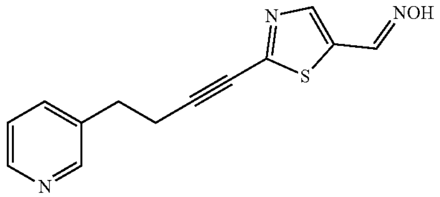

20

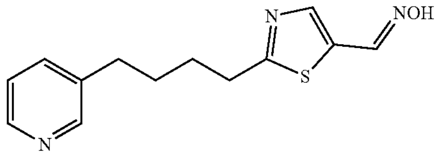

22

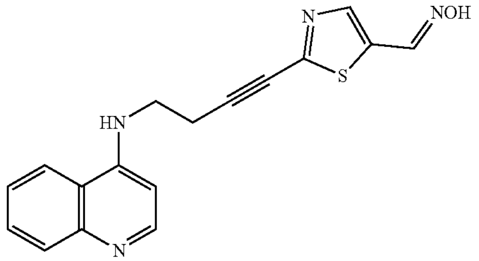

NM-139

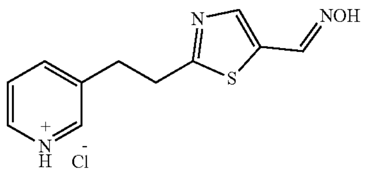

-continued

NM-141

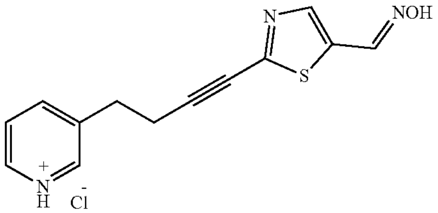

NM-143

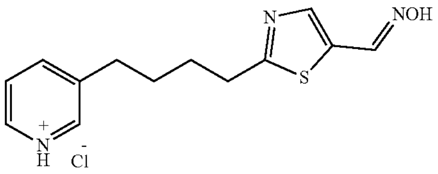

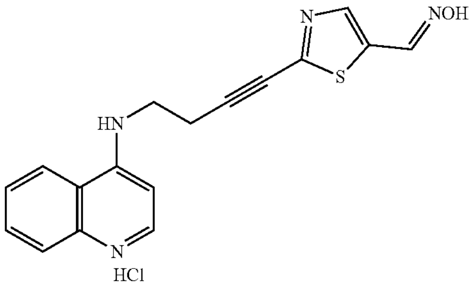

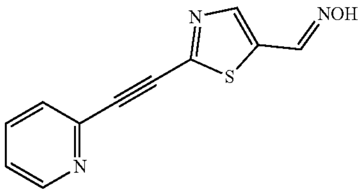

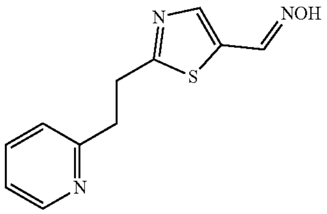

NM-204

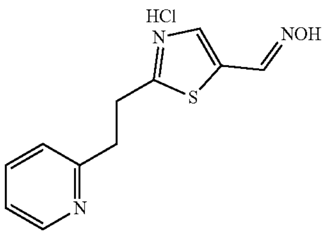

FR-73

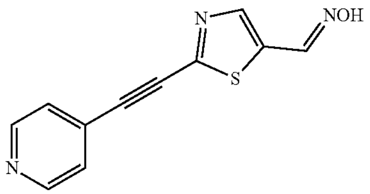

-continued

FR-77

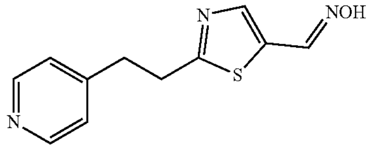

and

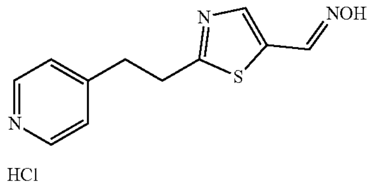

Preferably, the oxime group is in position 2.

According to a third embodiment, preferably, the —Y—(Z)n-R group is in 5 position, and the compound of formula (I) is a 5-substituted-2-oxime-(oxazole or thiazole) of formula (IV):

(IV)

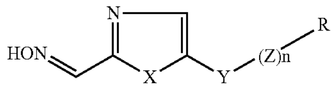

Preferably, X is S.

In such a case, the compounds of formula (I) are 5-substituted-2-oxime-1,3-thiazoles.

Preferably, X is O.

In such a case, the compounds of formula (I) are 5-substituted-2-oxime-1,3-oxazoles.

Preferably, Y is $—CH_2—CH_2—$ or —C≡C—, and n is 0, 1 or 2, preferably n is 0 or 2.

Preferably, R is a heteroaryl. Preferably said heteroaryl is not substituted. Preferably, said heteroaryl is a pyridine group such as 2-, 3- or 4-pyridino.

Preferably, according to said third embodiment, the compounds of formula (IV) are such that:

X is S;

Y is $—CH_2—CH_2—$ or —C≡C—, n is 0, 1 or 2, preferably n is 0 or 2; and

R is a heteroaryl, preferably said heteroaryl is not substituted and is a pyridine group such as 2-, 3- or 4-pyridino.

Preferably, when Y is $—CH_2—CH_2—$, n is preferably 0 or 2, and R is a heteroaryl, preferably not substituted, and is a pyridine group such as 2-, 3- or 4-pyridino.

Preferably, the compound of formula (IV) is chosen from the following compounds:

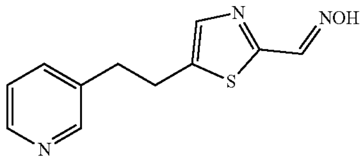

-continued

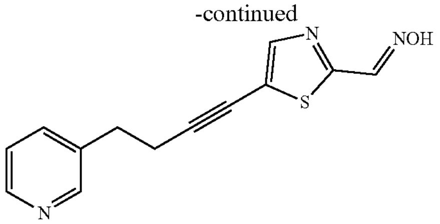

and

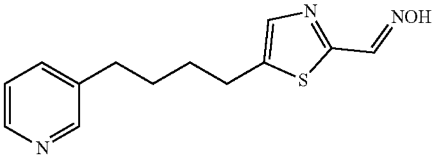

According to a fourth embodiment, preferably, the —Y—(Z)n-R group is in 4 position, and the compound of formula (I) is a 4-substituted-2-oxime-(oxazole or thiazole) of formula (V):

(V)

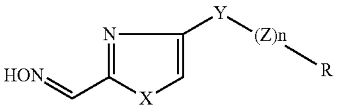

Preferably, X is S.

In such a case, the compounds of formula (I) are 4-substituted-2-oxime-1,3-thiazoles.

Preferably, X is O.

In such a case, the compounds of formula (I) are 4-substituted-2-oxime-1,3-oxazoles.

Preferably, Y is $—CH_2—CH_2—$ or —C≡C—, and n is 0, 1 or 2, preferably n is 0 or 2.

Preferably, R is a heteroaryl. Preferably said heteroaryl is not substituted. Preferably, said heteroaryl is a pyridine group such as 2-, 3- or 4-pyridino.

Preferably, according to said third embodiment, the compounds of formula (V) are such that:

X is S;

Y is $—CH_2—CH_2—$ or —C≡C—, n is 0, 1 or 2, preferably n is 0 or 2; and

R is an aryl or a heteroaryl, preferably said aryl is not substituted and is a phenyl, preferably said heteroaryl is not substituted and is a pyridine group such as 2-, 3- or 4-pyridino.

Preferably, when Y is $—CH_2—CH_2—$, n is preferably 0 or 2, and R is a heteroaryl, preferably not substituted, and is a pyridine group such as 2-, 3- or 4-pyridino.

Preferably, the compound of formula (V) is chosen from the following compounds:

26

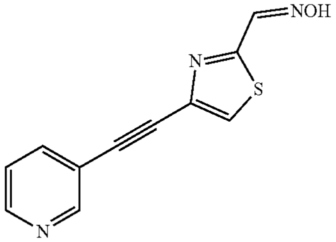

-continued

27

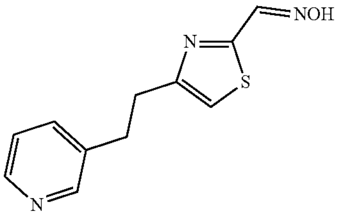

NM-171

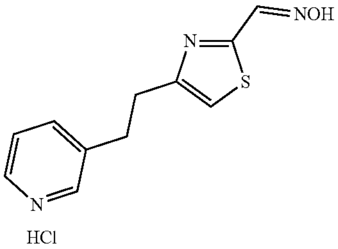

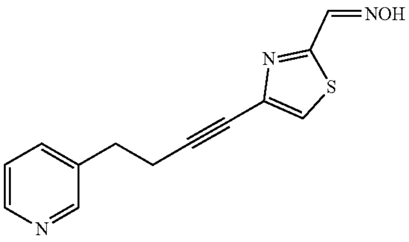

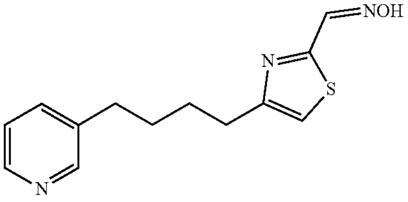

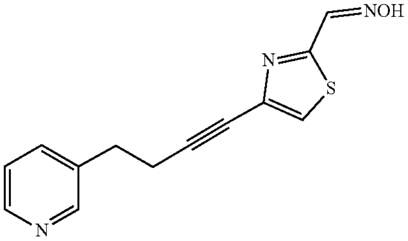

NM-259

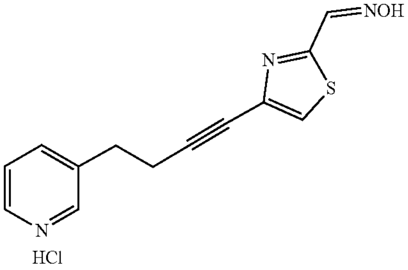

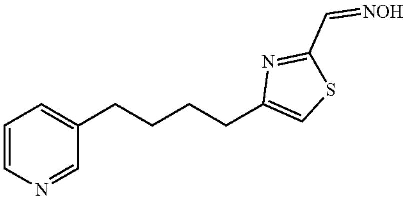

-continued
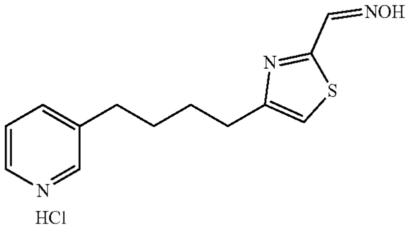
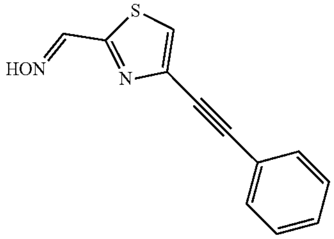
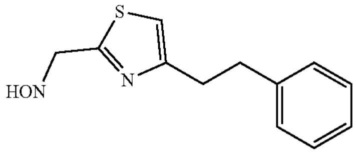
and
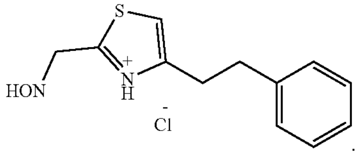
.
Preferably, the compound of formula (I) is chosen from compounds of formula (II), (III), (IV) and (V).
More preferably, the compound of formula (I) is chosen from:
NM-55
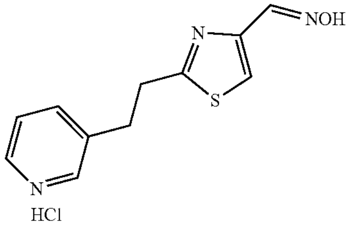
NM-131
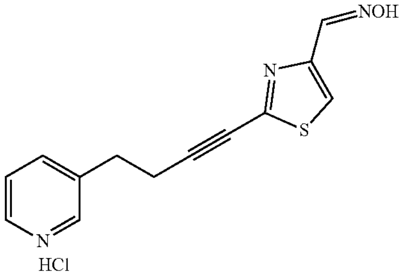
-continued
NM-132
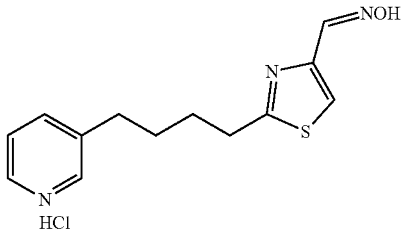
NM-109
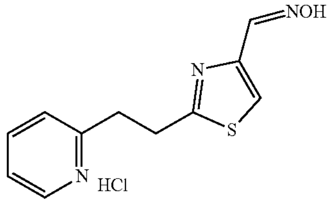
NM-130
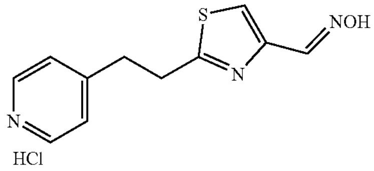
NM-46
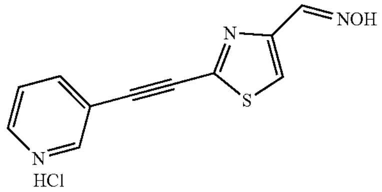
NM-176
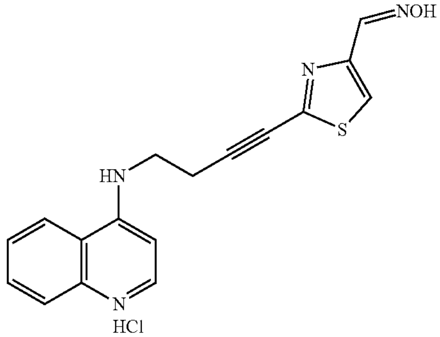
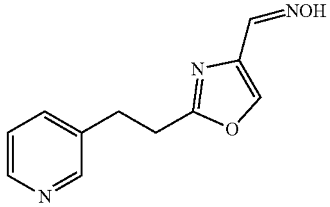
NM-139
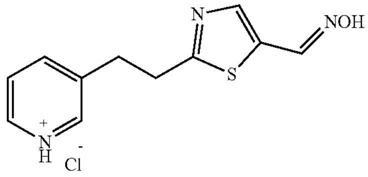

-continued
NM-141
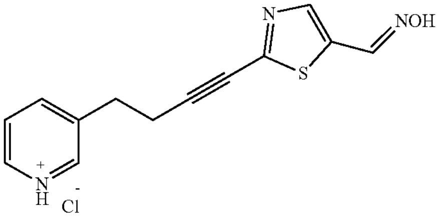
NM-143
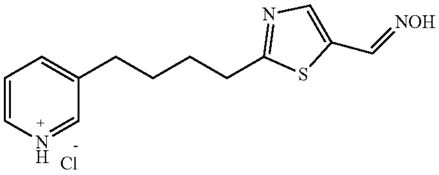
NM-152
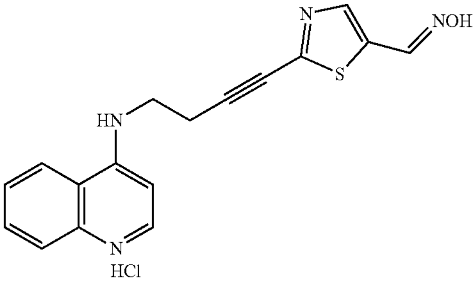
NM-168
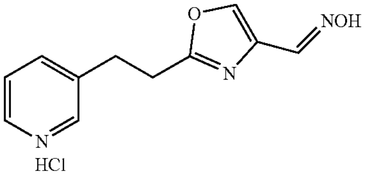
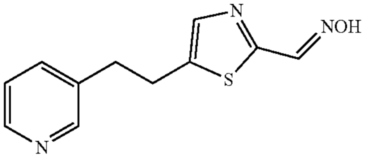
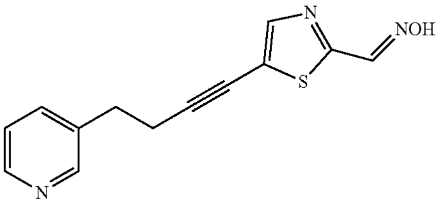
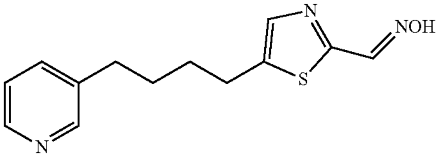
NM-171
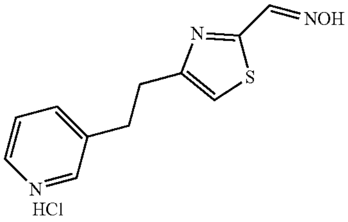
-continued
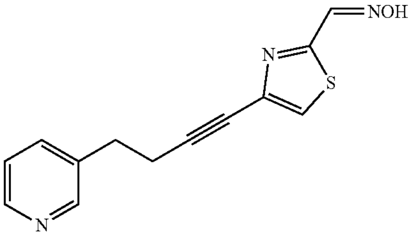
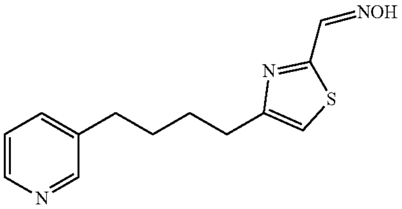
4
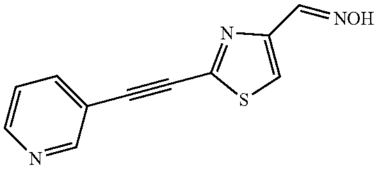
5
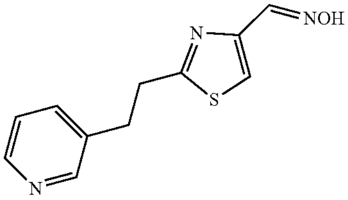
7
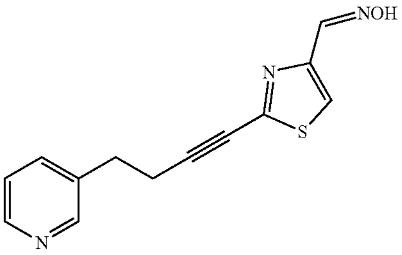
8
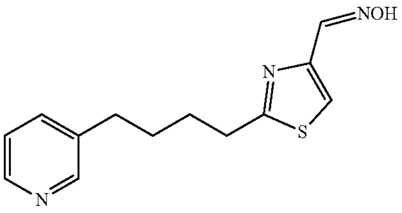
10
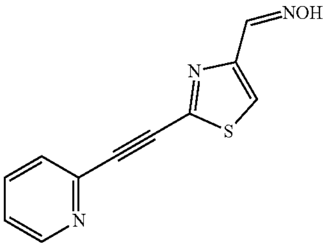

-continued
11
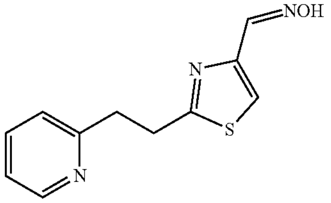
13
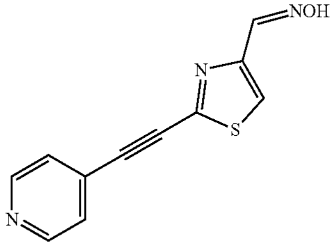
14
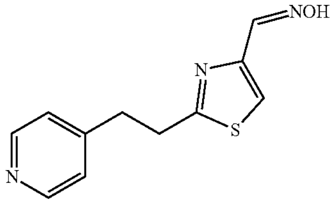
17
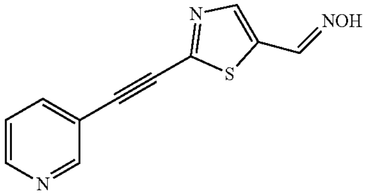
18
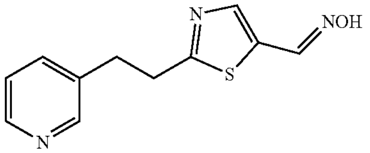
19
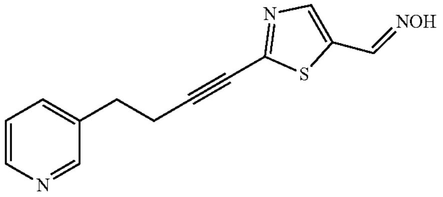
20
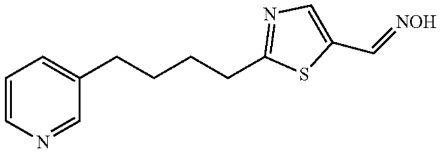
-continued
22
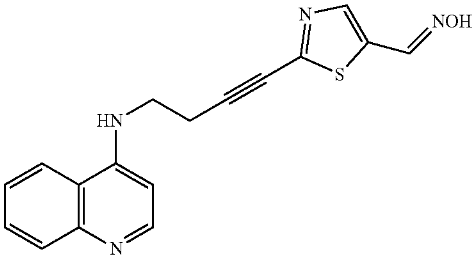
23
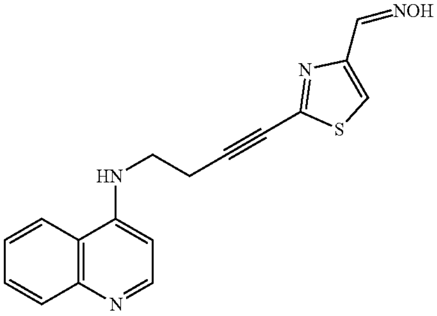
26
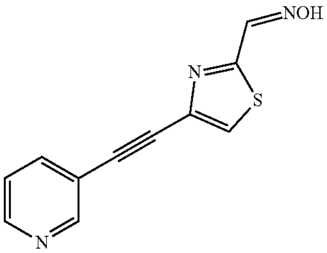
27
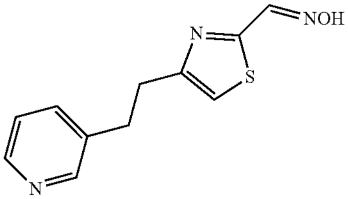
32
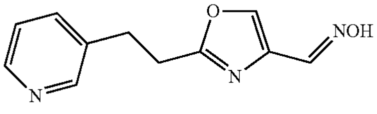
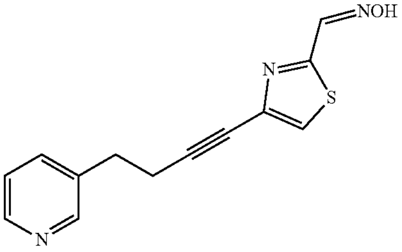

-continued
NM-259
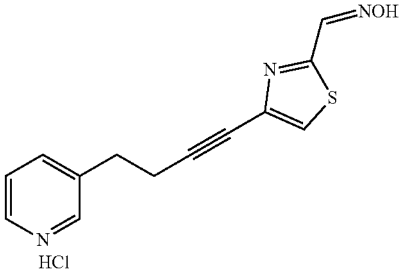
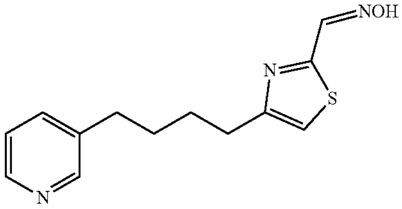
NM-261
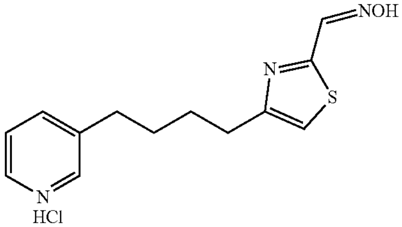
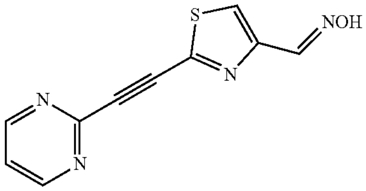
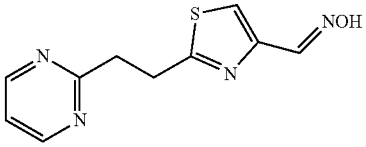
NM-250
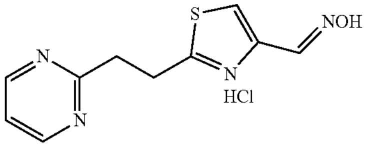
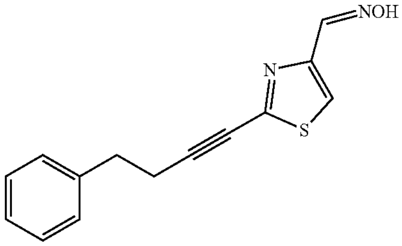
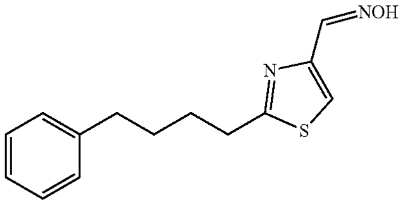
-continued
NM-247
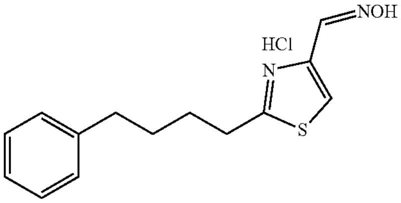
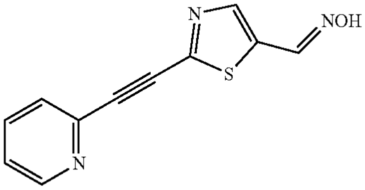
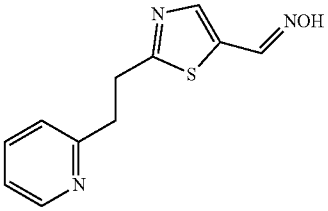
NM-204
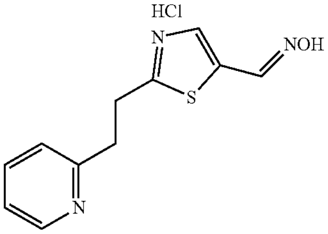
FR-72
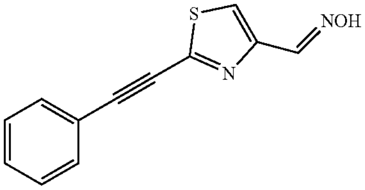
FR-74
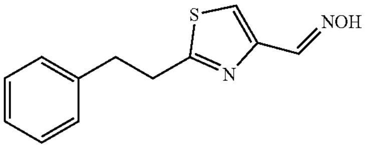
FR-78
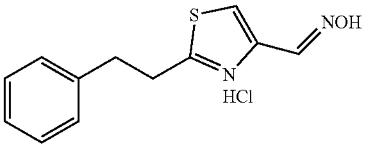
FR-73
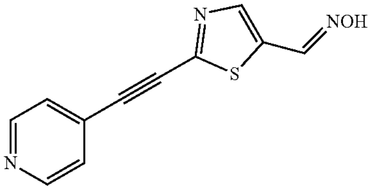

FR-77
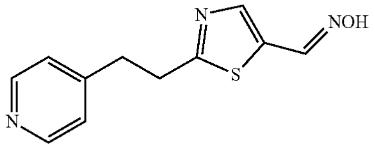
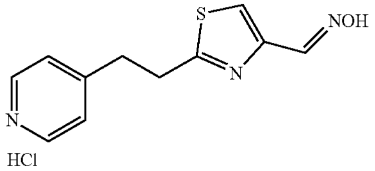
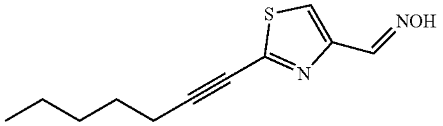
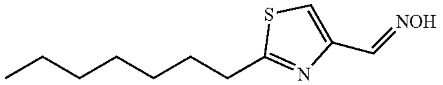
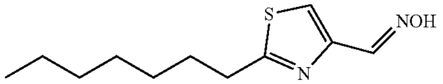
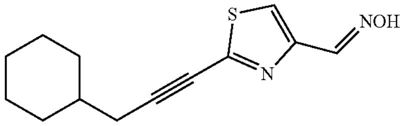
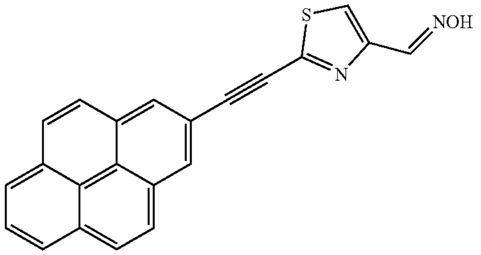
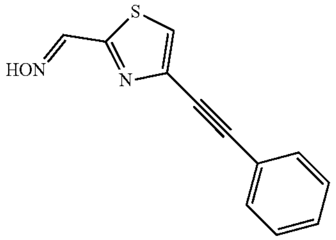
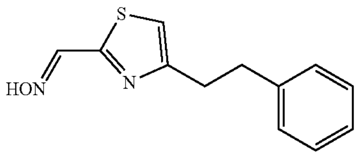
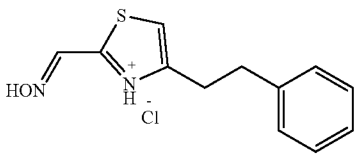
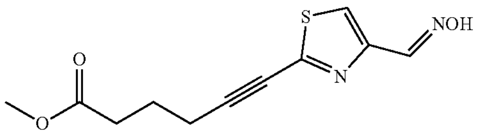
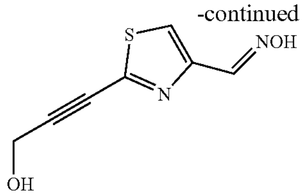
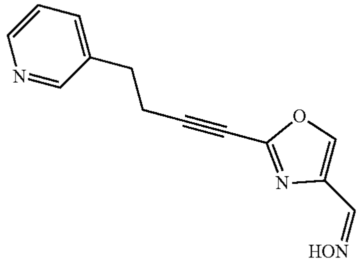
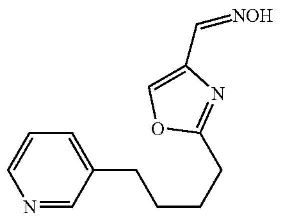
and
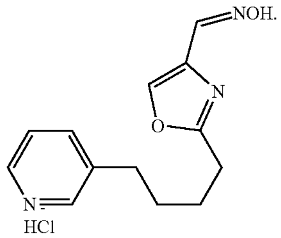
More preferably, the compound of formula (I) is chosen from:
NM-55
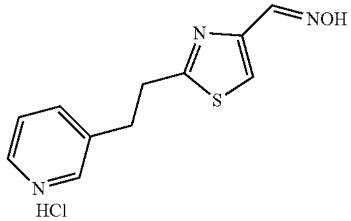
NM-131
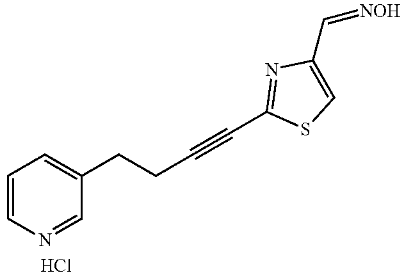

-continued
NM-132
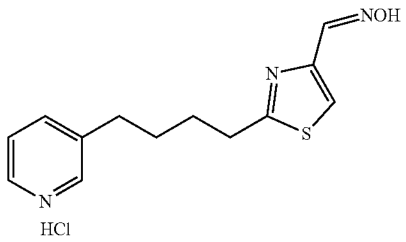
NM-109
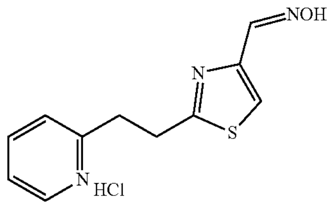
NM-130
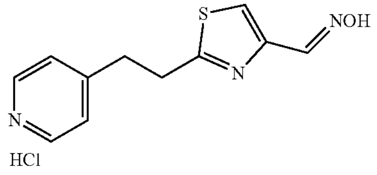
NM-46
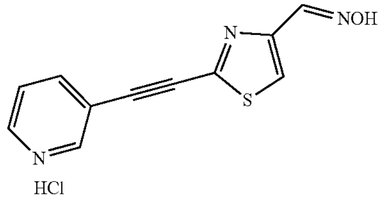
NM-176
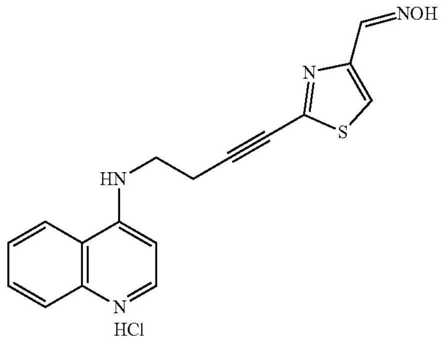
NM-139
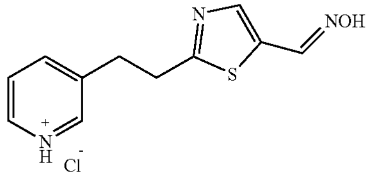
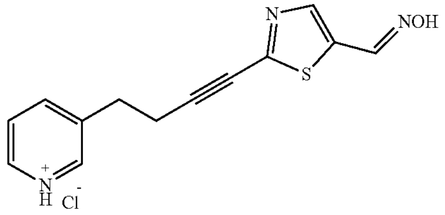
-continued
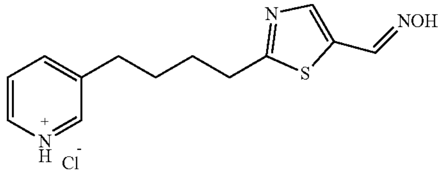
NM-152
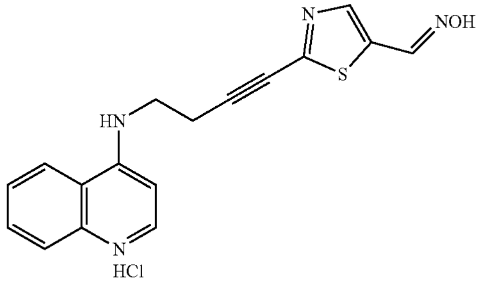
NM-168
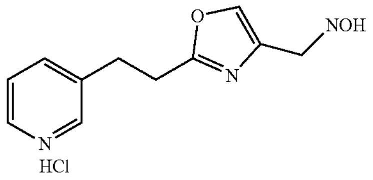
NM-171
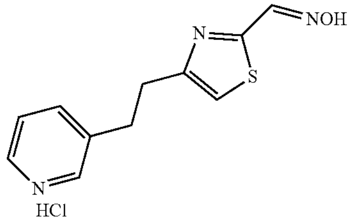
NM-259
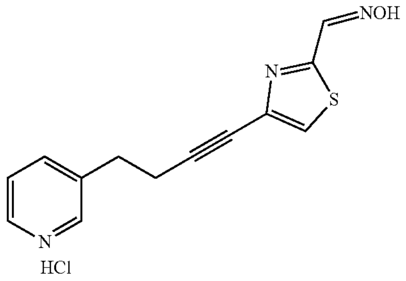
NM-261
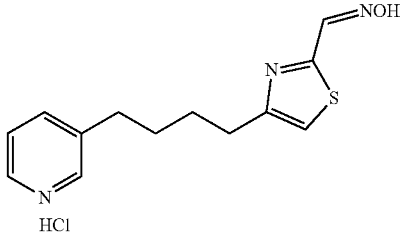
NM-250
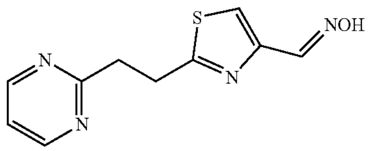

-continued

NM-247

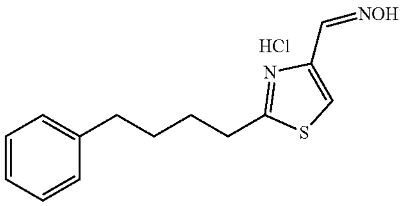

NM-204

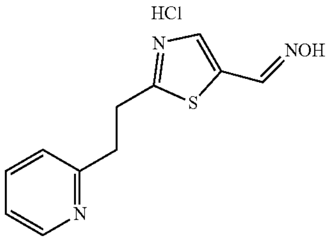

FR-78

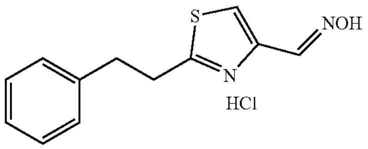

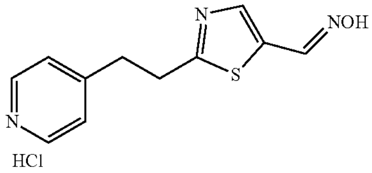

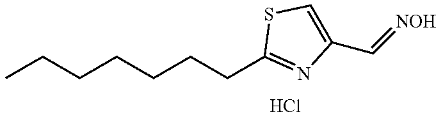

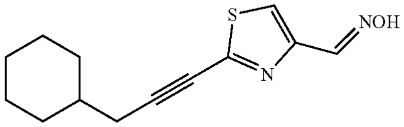

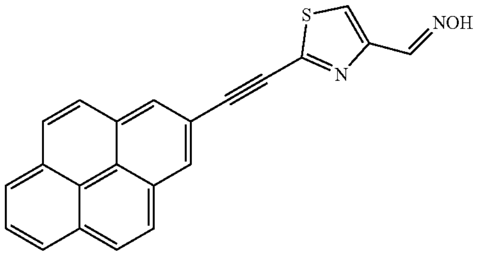

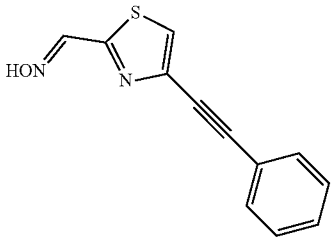

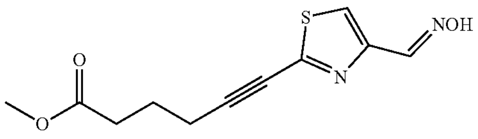

-continued

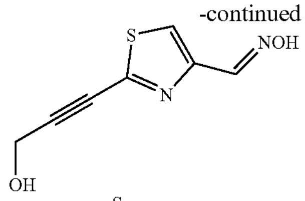

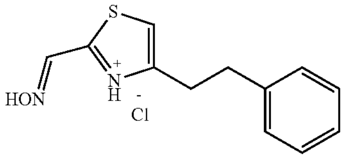

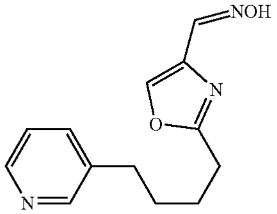

and

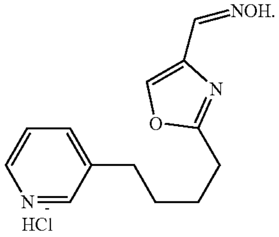

Preparation of the Compounds of Formula (I)

A compound of formula (I) according to the invention may be synthesized by any appropriate method. For example, when n is 0, the compounds of formula (I) may be prepared according to the following scheme

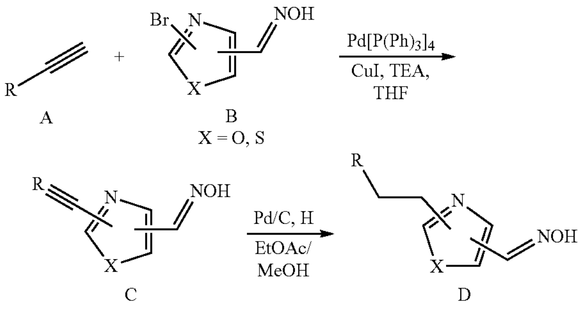

Such methods are exemplified in the following examples.

Preferably, the compounds of formula (I) are synthetized as described below. Such a process is chemoselective. Particularly, it does not necessitate any previous protection step of the oxime. Said process comprises a minimal number of steps (one or two), is quickly performed, at ambient temperature.

The main steps are as follows:

The late stage Sonogashira C—C cross-coupling reaction, recently developed by the group of the inventors (Yerri et al. *Eur. J. Med. Chem.* 2018, 4161-4165) was applied between terminal alkyne A and isomers of unprotected bromo-oxime-1,3-thiazole or unprotected isomers of bromo-oxime-1,3-oxazole B under palladium catalysis afford the conjugate C (which is of formula (I)). Said conjugate is then submitted to hydrogenation with Pd/C catalyst in heterogeneous conditions, to provide the corresponding alkene, and finally the hybrid reactivator D (which is of formula (I)).

Compounds C, alkene and D are all according to the invention.

When n is 1, 2, 3 or 4, then the above process is also applicable.

Thus, the present invention also relates to a process for preparing a compound of formula (I), which comprises the following steps:

a Sonogashira coupling reaction between a terminal alkyne

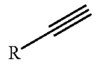

and an isomer of unprotected bromo-oxime-1,3-thiazole or an isomer of unprotected bromo-oxime-1,3-oxazole, preferably under palladium catalysis, to obtain the conjugate

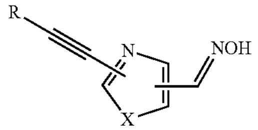

(which is of formula (I)):

optionally, said conjugate is then submitted to hydrogenation, preferably with Pd/C catalyst in heterogeneous conditions, to provide the corresponding alkene, and finally the hybrid reactivator

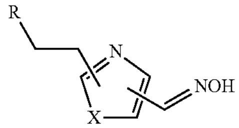

(which is of formula (I)).

Pharmaceutical Uses of the Compounds of the Invention

The compounds of this invention may be used in the treatment of a nervous and/or respiratory failure due to intoxication with at least one organophosphorous nerve agent which may preferably be selected from warfare agents such as O-ethyl S-[2-(diisopropylamino)ethyl] methylphosphonothioate (VX), tabun, sarin, cyclosarin and soman and pesticides such as paraoxon, parathion and tetraethyl pyrophosphate (TEPP). The compounds of the invention may be used in the treatment of a nervous and/or respiratory failure due to intoxication with at least one organophosphorous nerve agent, by virtue of their reactivation potency of organophosphorous inhibited cholinesterases, including acetylcholinesterase and butyrylcholinesterase. These compounds may alternatively be used in the treatment of diseases, which involve a reduced production of acetylcholine that may be overcome by the administration of acetylcholinesterase inhibitors. Examples of such diseases include in particular neurological diseases such as Alzheimer's disease.

These compounds may alternatively be used in the treatment of cancer, thanks to their action as inhibitors of histone deacetylases (HDAC).

The compound of this invention is usually included in a pharmaceutical composition comprising at least one compound according to the invention and a pharmaceutically acceptable support.

The amount of compound of formula (I) in the composition according to the invention may vary in a broad range depending upon the patient, the mode of administration and the expected effect.

The compound or composition according to the invention can be administered orally or non-orally, for instance via topical, parenteral, intramuscular, intravenous, cutaneous, nasal or rectal route.

The pharmaceutical composition of the invention can present different forms including granules, powders, tablets, capsules, syrups, emulsions, suspensions, and forms used for non-oral administration, for instance injections, sprays, transdermal patches or suppositories. These pharmaceutical forms can be prepared via known conventional techniques.

The preparation of an orally administered solid pharmaceutical form can be for instance performed by the following process: an excipient (for example lactose, sucrose, starch or mannitol), a desintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active principle and the mixture obtained is then tabletted. If necessary, the tablet can be coated via the known techniques, in order to mask the taste (for example with cocoa powder, mint, borneol or cinnamon powder) or to allow enteric dissolution or sustained release of the active principles. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active principle is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween® 80, HCO® 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as, if desired, a solubilizing agent (for example sodium salicylate or sodium acetate) or a stabilizer (for example human serum albumin).

Pharmaceutical forms for external use (topical use) can be obtained from a solid, semi-solid or liquid composition containing the active principle. For example, to obtain a solid form, the active principle can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

A method for the treatment of a nervous and/or respiratory failure due to intoxication with at least one organophosphorous nerve agent, comprising administering at least one compound according to the invention is also described herein.

A method for the treatment of a neurological disease such as Alzheimer's disease, comprising administering at least one compound according to the invention is also described herein.

A method for the treatment of a cancer, comprising administering at least one compound according to the invention is also described herein.

A method for the treatment of a virus, comprising administering at least one compound according to the invention is also described herein.

Within the context of the invention, the term treatment denotes curative, symptomatic, and/or preventive treatments. In particular, it can refer to reducing the progression of the disease, reducing or suppressing at least one of its symptoms or complications, or improving in any way the state of health of patients.

The administration of the compounds or of the composition according to the invention may be performed before, during or after the exposition of the subject to the organophosphorous nerve agent.

In the present invention, the terms "subject" and "patient" are used indifferently and designate a human subject.

The amount of compound according to the invention to be administered according to the invention may vary in a broad range depending upon the patient, the mode of administration and the expected effect. In particular, the amount of compound according to the invention may be comprised between 200 mg and 4000 mg, with up to 3 daily intakes.

The compound or composition according to the invention may be co-administered with at least one other active agent, such as an antimuscarinic agent, in particular atropine, an anticonvulsant, in particular diazepam or one of its prodrugs, such as avizafone, and/or a bioscavenger able to capture and/or degrade OPNAs in blood, such as human butyrylcholinesterase.

The term co-administered means that the administration of the compound or composition according to the invention and that of the other active agent can be simultaneous, sequential and/or separate.

Other Uses of the Compounds of the Invention

The compounds of this invention may further be used as tools for in vivo and/or in vitro biological studies. In this application, the compounds according to the invention may include one or more isotopes, which will allow for their detection.

The following examples are provided as illustrative, and not limitative, of the present invention.

EXAMPLES

Example 1: Synthesis of Compounds of the Invention

2-(2-(pyridin-3-yl)ethyl)thiazole-4-carbaldehyde oxime hydrochloride NM-55

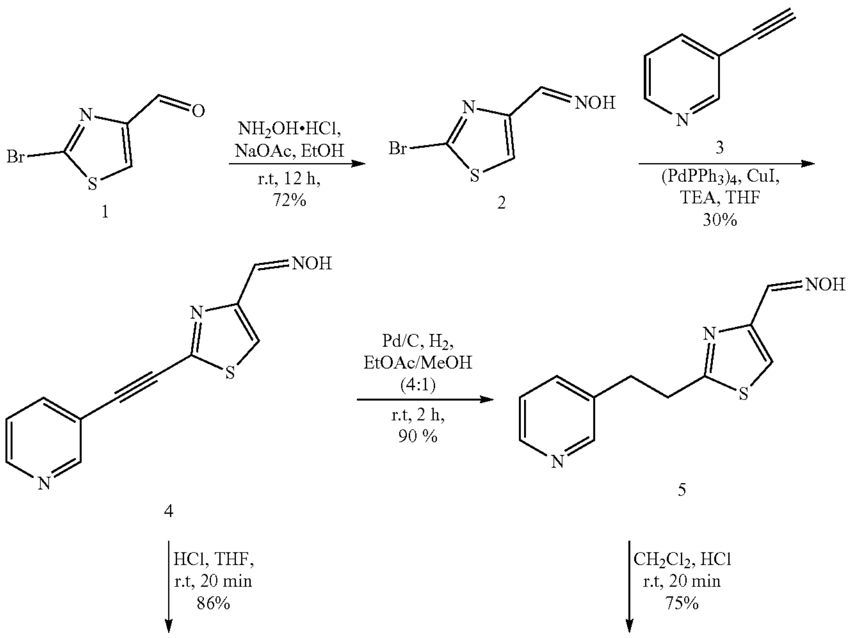

-continued

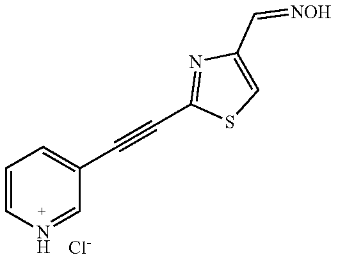

NM-46

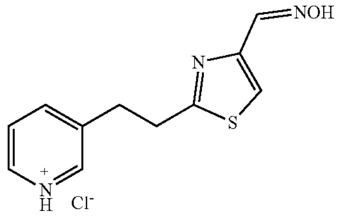

NM-55

2-bromothiazole-4-carbaldehyde oxime (2)

2

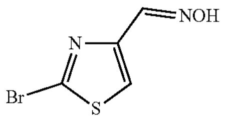

A solution of commercially available 2-bromothiazole-4-carbaldehyde 1 (200 mg, 1.04 mmol, 1 equiv), hydroxylamine hydrochloride (144 mg, 2.04 mmol, 2 equiv), and NaOAc (256 mg, 3.12 mmol, 3 equiv) in EtOH (6 mL) was stirred at room temperature for 12 h. Upon completion, the reaction mixture was filtered through a small celite pad. The filtrate was concentrated under reduced pressure and the residue was purified by column chromatography (EtOAc/PE 1:9) to afford cis/trans isomers (1/0.56 ratio) of (E/Z)-2-bromothiazole-4-carbaldehyde oxime 2 as off white solid (155 mg, 72%); $R_f$ (20% EtOAc/PE) 0.50; NMR (400 MHz, $CDCl_3$): δ ppm 8.37 (s, 0.56H), 8.18 (s, 1H), 7.73 (s, 0.56H), 7.49 (s, 1H); $^{13}C$ NMR (101 MHz, $CDCl_3$): δ ppm 148.78, 145.45, 143.45, 140.09, 137.26, 135.63, 129.52, 121.89.

2-(pyridin-3-ylethynyl)thiazole-4-carbaldehyde oxime 4

4

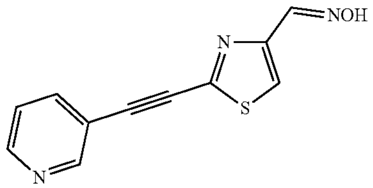

To a degassed solution of (E/Z)-2-bromothiazole-4-carbaldehyde oxime 2 (132 mg, 0.637 mmol, 1.1 equiv) in THF/$Et_3N$ (6 mL/2 mL), Pd[$PPh_3$]$_4$ (101 mg, 0.087 mmol, 0.15 equiv) and CuI (33 mg, 0.173 mmol, 0.3 equiv) were added. After degassing the reaction mixture for 5 min at room temperature, 3-ethynylpyridine 3 (60 mg, 0.582 mmol, 1 equiv) was added dropwise and the reaction mixture was stirred at room temperature for 16 h. Upon completion, the reaction mixture was concentrated under reduced pressure and the residue was purified by column chromatography (EtOAc/PE 50:50) to afford cis/trans isomers (7.5/2.5 ratio) of (E/Z)-2-(pyridin-3-ylethynyl)thiazole-4-carbaldehyde oxime 4 as a light yellowish solid (30 mg, 30%); IR (neat): $v_{max}$ 3081, 2784, 1478, 1405, 1281, 1104, 969, 778, 744, 696, 635, 569, 522, 486 $cm^{-1}$; $R_f$ (40% EtOAc/PE) 0.30; HRMS ($ESI^+$): m/z calcd for $C_{11}H_8N_3OS^+$ 230.038586 found 230.03829; $^1H$ NMR (400 MHz, $CDCl_3$): δ ppm 8.88-8.81 (m, 1H), 8.64 (dt, J=9.0, 4.4 Hz, 1H), 8.52 (s, 0.75H), 8.27 (d, J=8.8 Hz, 0.25H), 7.91 (tt, J=7.7, 1.8 Hz, 1H), 7.81 (s, 0.75H), 7.65 (s, 0.25H), 7.40-7.33 (m, 1H). $^{13}C$ NMR (101 MHz, $CDCl_3$): δ ppm 152.36, 152.32, 149.81, 149.78, 149.75, 149.36, 148.42, 146.66, 146.08, 140.26, 139.58, 139.07, 139.04, 127.15, 123.31, 119.70, 118.58, 118.53, 90.93, 90.88, 84.95, 84.70.

2-(pyridin-3-ylethynyl)thiazole-4-carbaldehyde oxime hydrochloride NM-46

NM-46

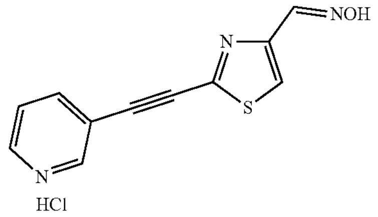

To a solution of (E/Z)-2-(pyridin-3-ylethynyl)thiazole-4-carbaldehyde oxime 4 (12 mg, 0.052 mmol) in water (2 mL) was added 2N HCl (1 mL) at room temperature and stirred for 20 min at same temperature. Upon completion, solvent was distilled off under reduced pressure and the resulting solid was washed with diethyl ether (2×3 mL). The solid was dried under vacuum to give cis/trans isomers (3/2 ratio) of (E/Z)-2-(pyridin-3-ylethynyl)thiazole-4-carbaldehyde oxime hydrochloride NM-46 as a pale yellow solid (12 mg, 86%); IR (neat): $v_{max}$ 3075, 2359, 1530, 955, 888, 798, 761, 667 $cm^{-1}$; HRMS ($ESI^+$): m/z calcd for $C_{11}H_9ClN_3OS^+$ 266.014937 found 266.013282; $^1H$ NMR (500 MHz, DMSO-$d_6$): δ ppm 12.22 (s, 0.4H), 11.50 (s, 0.6H), 9.22 (s, 1H), 8.79 (s, 1H), 8.74 (s, 0.4H), 8.25 (s, 0.6H), 8.16 (s, 0.6H), 8.13-8.10 (m, 1H), 7.80 (m, 1H), 7.75 (s, 0.4H); $^{13}C$ NMR (126 MHz, DMSO-$d_6$): δ ppm 161.94, 160.30, 149.85, 147.73, 145.70, 144.95, 143.28, 139.85, 138.24, 134.07, 131.23, 130.98, 127.63, 125.65, 123.74, 123.56, 121.08.

2-(2-(pyridin-3-yl)ethyl)thiazole-4-carbaldehyde oxime 5

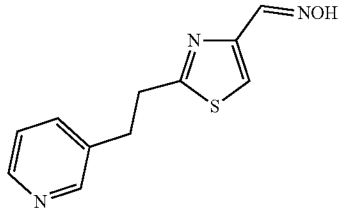

5

To a solution of (E/Z)-2-(pyridin-3-ylethynyl)thiazole-4-carbaldehyde oxime 4 (20 mg, 0.087 mmol) in 4:1 ratio of EtOAc/MeOH (5 mL) was added 10% Pd/C (10 mg) at room temperature under Argon atmosphere and stirred the mixture for 1 h under $H_2$ atmosphere using balloon pressure. Upon completion, the mixture was filtered through a small celite pad and concentrated under reduced pressure. The crude was purified by column chromatography (EtOAc/PE, 70:30) to afford cis/trans isomers (6/4 ratio) of (E/Z)-2-(2-(pyridin-3-yl)ethyl)thiazole-4-carbaldehyde oxime 5 as a white solid (17 mg, 83%); $R_f$(50% EtOAc/PE) 0.20; IR (neat): $\nu_{max}$ 2921, 2850, 2360, 1731, 1579, 1421, 1123, 969, 913, 794, 704 $cm^{-1}$; HRMS (ESI$^+$): m/z calcd for $C_{11}H_{12}N_3OS^+$ 234.069559 found 234.068309; $^1H$ NMR (400 MHz, $CDCl_3$): δ ppm 8.50 (bs, 2H), 8.22 (s, 0.4H), 8.12 (s, 0.6H), 7.74 (s, 0.6H), 7.54 (d, J=7.8 Hz, 1H), 7.37 (s, 0.4H), 7.27-7.18 (m, 1H), 3.40-3.28 (m, 2H), 3.18-3.14 (m, 2H); $^{13}C$ NMR (101 MHz, $CDCl_3$): δ 170.08, 168.13, 149.73, 149.70, 148.64, 147.83, 147.74, 144.21, 136.23, 135.64, 135.44, 124.16, 123.61, 118.38, 34.63, 34.25, 32.84, 32.71.

2-(2-(pyridin-3-yl)ethyl)thiazole-4-carbaldehyde oxime hydrochloride NM-55

NM-55

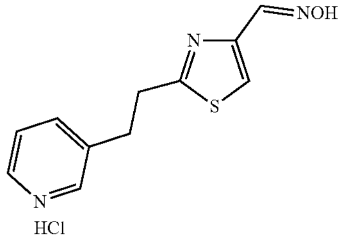

To a solution of (E/Z)-2-(2-(pyridin-3-yl)ethyl)thiazole-4-carbaldehyde oxime 5 (14 mg, 0.06 mmol) in $CH_2Cl_2$ (3 ml) was added 2N HCl (0.1 mL) at room temperature and stirred for 30 min at same temperature. Upon completion, solvent was distilled off under reduced pressure and the resulting solid was washed with diethyl ether (2×3 mL). The solid was dried under vacuum to give cis/trans isomers (6.5/3.5 ratio) of (E/Z)-2-(2-(pyridin-3-yl)ethyl)thiazole-4-carbaldehyde oxime hydrochloride NM-55 as a light brown solid (12 mg, 74%); IR (neat): $\nu_{max}$ 3056, 2360, 1632, 1556, 1470, 1263, 984, 926, 775, 679 $cm^{-1}$; $^1H$ NMR (400 MHz, $CD_3OD$): δ ppm 8.94 (s, 0.65H), 8.90 (s, 0.35H), 8.86-8.74 (m, 1H), 8.67 (t, J=9.1 Hz, 1H), 8.55 (s, 0.35H), 8.22 (s, 1.7H), 7.96 (s, 0.65H), 7.65 (s, 0.35H), 3.75-3.59 (m, 2H), 3.48 (t, J=7.3 Hz, 2H). $^{13}C$ NMR (101 MHz, $CD_3OD$): δ ppm 169.64, 147.20, 141.36, 141.31, 140.73, 140.26, 139.75, 139.59, 136.98, 127.21, 127.13, 125.72, 31.52, 31.35, 31.32.

2-(4-(pyridin-3-yl)butyl)thiazole-4-carbaldehyde oxime hydrogen chloride NM-131

2-(4-(pyridin-3-yl)but-1-yn-1-yl)thiazole-4-carbaldehyde oxime hydrogen chloride NM-132

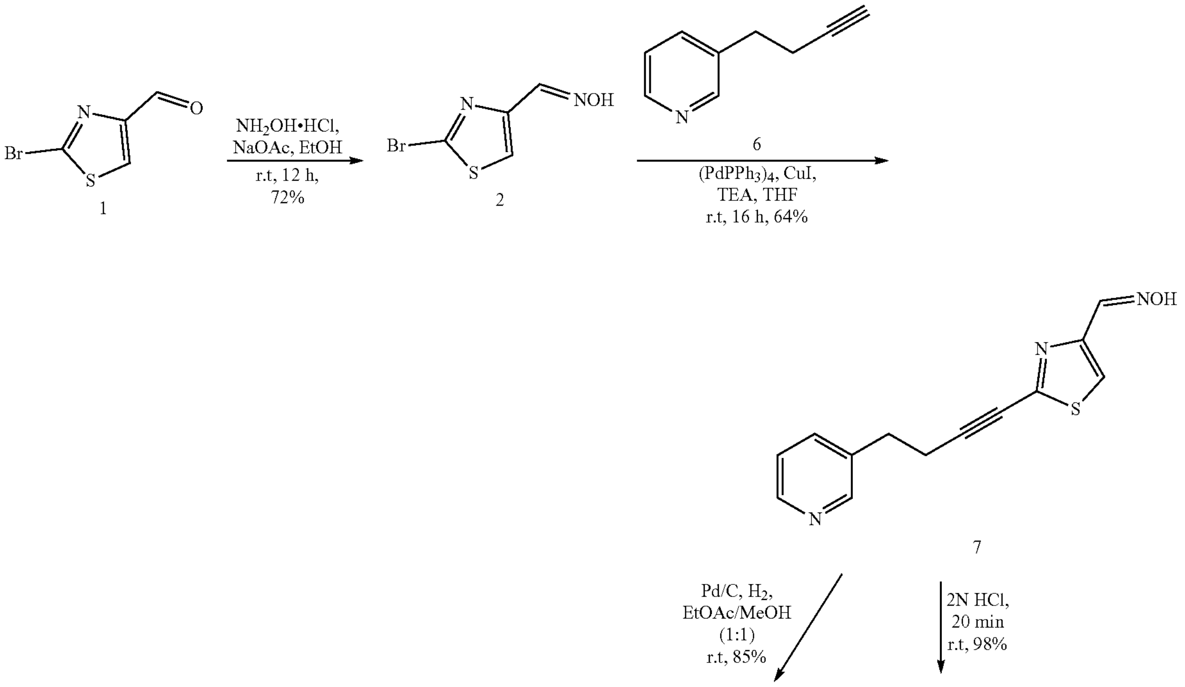

-continued

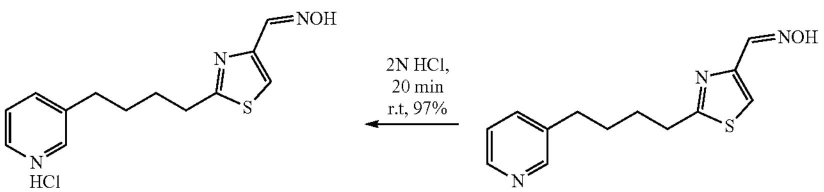

NM-132 8

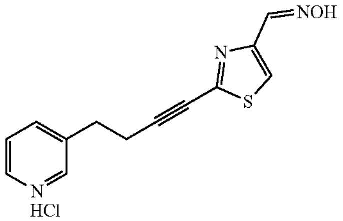

NM-131

2-(4-(pyridin-3-yl)but-1-yn-1-yl)thiazole-4-carbaldehyde oxime 7

7

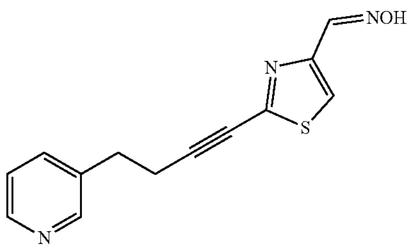

To a degassed solution of (E/Z)-2-bromothiazole-4-carbaldehyde oxime 2 (104 mg, 0.502 mmol, 1.1 equiv) in THF/$Et_3N$ (6 mL/2 mL), $Pd[PPh_3]_4$ (79.4 mg, 0.068 mmol, 0.15 equiv) and CuI (26 mg, 0.137 mmol, 0.3 equiv) were added. After degassing the reaction mixture for 5 min at room temperature, 3-(but-3-yn-1-yl)pyridine 6 (60 mg, 0.458 mmol, 1 equiv) was added dropwise and the reaction mixture was stirred at the room temperature for 16 h. Upon completion, the reaction mixture was concentrated under reduced pressure and the residue was purified by column chromatography (EtOAc/PE 70:30) to afford cis/trans isomers (8/2 ratio) of (E)-2-(4-(pyridin-3-yl)but-1-yn-1-yl)thiazole-4-carbaldehyde oxime 7 as an off white solid (75 mg, 64%); $R_f$ (40% EtOAc/PE) 0.50; IR (neat): $v_{max}$ 3069, 2689, 2234, 1580, 1447, 1428, 1205, 1032, 969, 798, 772, 709, 643 $cm^{-1}$; HRMS ($ESI^+$): m/z calcd for $C_{13}H_{12}N_3OS^+$ 258.069559 found 258.067414; $^1H$ NMR (400 MHz, $CD_3OD$): δ ppm 8.50 (bs, 3H), 7.84 (d, J=7.8 Hz, 1H), 7.72 (s, 0.2H) 7.55 (s, 0.8H), 7.44 (bs, 1H), 3.00 (t, J=6.9 Hz, 2H), 2.86 (t, J=6.9 Hz, 2H); $^{13}C$ NMR (101 MHz, $CD_3OD$): δ ppm 150.27, 149.12, 148.20, 146.75, 140.21, 138.48, 127.49, 96.98, 96.75, 75.45, 32.10, 21.79.

As a note, 3-(but-3-yn-1-yl)pyridine 6 may be described as in Galli et al, *Chem Med Chem* 2008, 3, 771-779; or Joseph et al, *J. Org. Chem.* 2013, 78, 1670-1676.

2-(4-(pyridin-3-yl)but-1-yn-1-yl)thiazole-4-carbaldehyde oxime hydrochloride NM-131

NM-131

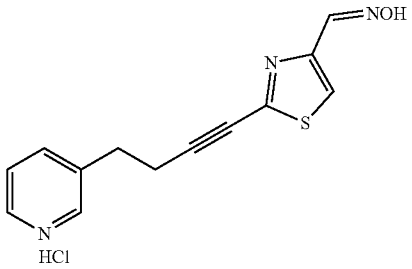

To a solution of (E/Z)-2-(4-(pyridin-3-yl)but-1-yn-1-yl) thiazole-4-carbaldehyde oxime 7 (16 mg, 0.062 mmol) was added 2N HCl (2 mL) at room temperature and stirred for 20 min at same temperature. Upon completion, solvent was distilled off under reduced pressure and the resulting solid was washed with diethyl ether (2×4 mL). The solid was dried under vacuum to give cis/trans mixture (6.5/3.5 ratio) of (E/Z)-2-(4-(pyridin-3-yl)but-1-yn-1-yl)thiazole-4-carbaldehyde oxime hydrochloride NM-131 as a light brown solid (18 mg, 98%); IR (neat): $v_{max}$ 3037, 2361, 1632, 1544, 1463, 979, 912, 792, 771, 678, 618 $cm^{-1}$; HRMS ($ESI^+$): m/z calcd for $C_{13}H_{13}ClN_3OS^+$ 294.046237 found 294.04566; $^1H$ NMR (400 MHz, $CD_3OD$): δ ppm 8.91-8.61 (m, 4H), 8.08 (s, 1H), 7.64-7.56 (m, 0.35H), 7.23-6.91 (m, 0.65H), 3.32-3.02 (m, 4H); $^{13}C$ NMR (101 MHz, $CD_3OD$): δ ppm 162.40, 149.17, 148.96, 143.42, 143.13, 142.22, 142.13, 141.53, 141.35, 140.90, 129.11, 128.90, 127.12, 122.27, 42.42, 41.89, 31.74, 31.65.

2-(4-(pyridin-3-yl)butyl)thiazole-4-carbaldehyde oxime 8

8

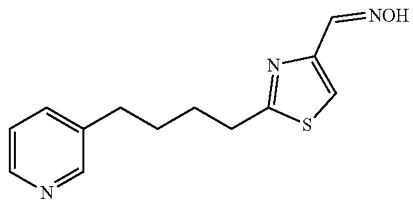

To a solution of (E/Z)-2-(4-(pyridin-3-yl)but-1-yn-1-yl) thiazole-4-carbaldehyde oxime 7 (20 mg, 0.077 mmol) in 4:1 ratio of EtOAc/MeOH (5 mL) was added 10% Pd/C (10 mg) at room temperature under Argon atmosphere and stirred the mixture for 2 h under $H_2$ atmosphere using balloon pressure. Upon completion, the mixture was filtered through a small celite pad and concentrated under reduced pressure. The crude was purified by preparative TLC (EtOAc/PE, 1:1) to afford cis/trans isomers (1/1 ratio) of (E/Z)-2-(4-(pyridin-3-yl)butyl)thiazole-4-carbaldehyde oxime 8 as white solid (17.6 mg, 83%); $R_f$ (60% EtOAc/PE) 0.20; IR (neat): $v_{max}$ 3063, 2922, 2854, 2360, 2340, 1579, 1462, 1424, 1098, 967, 924, 796, 781, 706, 642 $cm^{-1}$; HRMS ($ESI^+$): m/z calcd for $C_{13}H_{16}N_3OS^+$ 262.100860 found 260.100806; $^1H$ NMR (400 MHz, $CD_3OD$): δ ppm 8.34-8.22 (m, 2.5H), 8.02 (s, 0.5H) 7.60 (d, J=7.8 Hz, 1H), 7.47 (d, J=9.1 Hz, 1H), 7.25 (dd, J=7.4, 4.9 Hz, 1H), 2.96 (t, J=7.4 Hz, 2H), 2.62 (t, J=6.7 Hz, 2H), 1.80-1.50 (m, 4H); $^{13}C$ NMR (101 MHz, $CD_3OD$): δ ppm 173.92, 171.67, 150.04, 147.55, 146.20, 144.27, 140.67, 139.78, 138.28, 125.88, 125.21, 119.08, 33.57, 33.33, 33.30, 33.28, 31.44, 30.49, 30.44.

2-(4-(pyridin-3-yl)butyl)thiazole-4-carbaldehyde oxime hydrochloride NM-132

NM-132

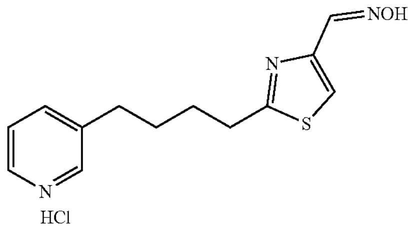

To a solution of (E/Z)-2-(4-(pyridin-3-yl)butyl)thiazole-4-carbaldehyde oxime 8 (10 mg, 0.06 mmol) was added 2N HCl (2 mL) at room temperature and stirred for 20 min at same temperature. Upon completion, solvent was distilled off under reduced pressure and the resulting solid was washed with diethyl ether (2x3 mL). The solid was dried under vacuum to give cis/trans mixture (7.5/2.5 ratio) of (E/Z)-2-(4-(pyridin-3-yl)butyl)thiazole-4-carbaldehyde oxime hydrochloride NM-132 as a light brown solid (11 mg, 97.3%); IR (neat): $v_{max}$ 3049, 1629, 1612, 1552, 1466, 1381, 1261, 991, 793, 680 $cm^{-1}$; HRMS ($ESI^+$): m/z calcd for $C_{13}H_{16}N_3OS^+$ 262.100860 found 260.1004291; $^1H$ NMR (500 MHz, $CD_3OD$): δ ppm 9.02-8.50 (m, 3.5H), 8.37-78.94 (m, J=2.25H), 7.67 (s, 0.25H) 3.37 (s, 2H), 3.03 (s, 2H), 2.18-1.76 (m, 4H); $^{13}C$ NMR (126 MHz, $CD_3OD$): δ ppm 173.92, 171.67, 150.04, 147.55, 146.20, 144.27, 140.67, 139.78, 138.28, 125.88, 125.21, 119.08, 33.57, 33.33, 33.30, 33.28, 31.44, 30.49, 30.44.

2-(2-(pyridin-2-yl)ethyl)thiazole-4-carbaldehyde oxime hydrochloride NM-109

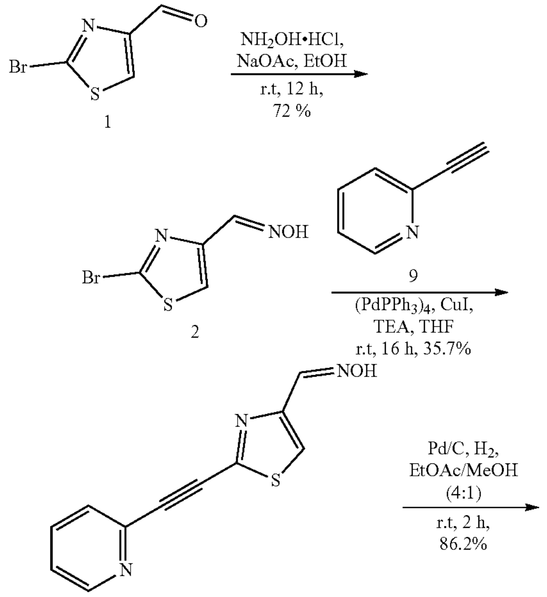

1
2
9
10

-continued

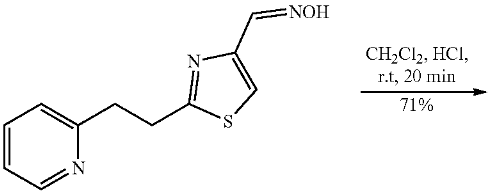

11

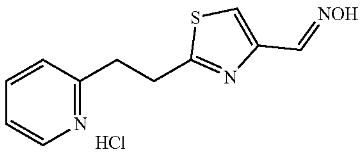

NM-109

2-(pyridin-2-ylethynyl)thiazole-4-carbaldehyde oxime 10

10

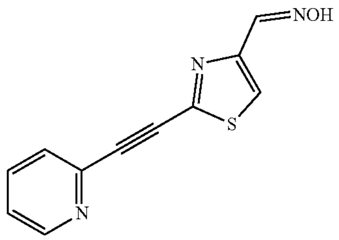

To a degassed solution of (E/Z)-2-bromothiazole-4-carbaldehyde oxime 2 (132 mg, 0.637 mmol, 1.1 equiv) in THF/$Et_3N$ (6 mL/2 mL), Pd[$PPh_3$]$_4$ (101 mg, 0.087 mmol, 0.15 equiv) and CuI (33 mg, 0.173 mmol, 0.3 equiv) were added. After degassing the reaction mixture for 5 min at room temperature, 2-ethynylpyridine 9 (60 mg, 0.582 mmol, 1 equiv) was added dropwise and the reaction mixture was stirred at the room temperature for 16 h. Upon completion, the reaction mixture was concentrated under reduced pressure and the residue was purified by column chromatography (EtOAc/PE 50:50) to afford (E)-2-(pyridin-2-ylethynyl) thiazole-4-carbaldehyde oxime 10 as an off white solid (40.5 mg, 35.7%); $R_f$(40% EtOAc/PE) 0.25; IR (neat): $v_{max}$ 3055, 2850, 1581, 1465, 1435, 1275, 1110, 996, 979, 769, 720, 692, 537 $cm^{-1}$; HRMS ($ESI^+$): m/z calcd for $C_{11}H_8N_3OS^+$ 230.038259 found 230.038791; $^1H$ NMR (400 MHz, $CD_3OD$): δ ppm 8.71 (s, 1H), 8.66-8.63 (m, 1H), 7.95 (td, J=7.8, 1.7 Hz, 1H), 7.78 (d, J=7.9 Hz, 1H), 7.67 (s, 1H), 7.53 (ddd, J=7.7, 5.0, 1.1 Hz, 1H); $^{13}C$ NMR (101 MHz, $CD_3OD$): δ ppm 151.25, 147.71, 147.57, 142.28, 140.18, 138.79, 129.43, 128.97, 125.97, 93.08, 81.94.

2-(2-(pyridin-2-yl)ethyl)thiazole-4-carbaldehyde oxime 11

11

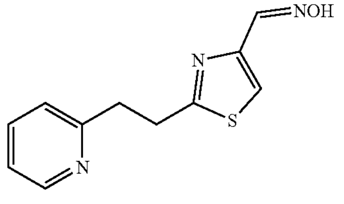

To a solution of (E)-2-(pyridin-2-ylethynyl)thiazole-4-carbaldehyde oxime 10 (40 mg, 0.087 mmol) in 4:1 ratio of EtOAc/MeOH (5 mL) was added 10% Pd/C (20 mg) at room temperature under Argon atmosphere and stirred the mixture for 2 h under $H_2$ atmosphere using balloon pressure. Upon completion, the mixture was filtered using celite pad and concentrated under reduced pressure. The crude was purified by column chromatography (EtOAc/PE, 70:30) to afford trans-cis isomers (6/4 ratio) of (E/Z)-2-(2-(pyridin-2-yl)ethyl)thiazole-4-carbaldehyde oxime 11 as pale yellow solid (35 mg, 86.2%); $R_f$ (50% EtOAc/PE) 0.20; IR (neat): $v_{max}$ 2920, 2851, 1592, 1569, 1476, 1435, 1174, 1117, 975, 922, 748, 721, 694, 539 $cm^{-1}$; HRMS ($ESI^+$): m/z calcd for $C_{11}H_{12}N_3OS^+$ 234.069559 found 234.069476. $^1H$ NMR (400 MHz, $CD_3OD$): δ 8.52-8.50 (m, 1H), 8.38 (s, 0.5H) 8.13 (s, 0.5H), 7.86-7.78 (m, 1H), 7.58-7.55 (m, 1H), 7.41-7.31 (m, 2H), 3.51-3.47 (m, 2H), 3.35-3.30 (m, 2H). $^{13}C$ NMR (101 MHz, $CD_3OD$): δ 170.79, 168.58, 159.02, 148.71, 147.93, 147.78, 142.91, 139.32, 138.22, 138.06, 131.79, 130.74, 124.67, 123.94, 123.86, 122.17, 122.12, 117.83, 36.58, 36.50, 32.17, 31.95.

2-(2-(pyridin-2-yl)ethyl)thiazole-4-carbaldehyde oxime hydrochloride NM-109

NM-109

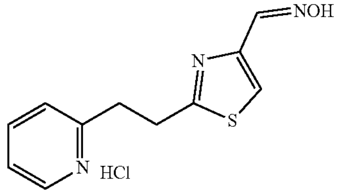

To a solution of (E/Z)-2-(2-(pyridin-2-yl)ethyl)thiazole-4-carbaldehyde oxime 11 (25 mg, 0.06 mmol) in $CH_2Cl_2$ (3 mL) was added 2N HCl (0.5 mL) at room temperature and stirred for 30 min at same temperature. Upon completion, solvent was distilled off under reduced pressure and the resulting solid was washed with diethyl ether (2×3 mL). The solid was dried under vacuum to give cis/trans isomer (6.5/3.5 ratio) of (E/Z)-2-(2-(pyridin-2-yl)ethyl)thiazole-4-carbaldehyde oxime hydrochloride NM-109 as a light brown solid (20 mg, 71%); IR (neat): $v_{max}$ 3055, 2922, 1617, 1435, 1189, 1117, 996, 752, 718, 692, 536 $cm^{-1}$; HRMS ($ESI^+$): m/z calcd for $C_{11}H_{12}N_3OS^+$ 234.0696 found 234.0697; $^1H$ NMR (400 MHz, $CD_3OD$): δ ppm 8.82-8.79 (m, 1H), 8.61-8.56 (m, 1H), 8.47 (s, 0.3H), 8.17 (s, 0.7H), 8.09 (dd, J=8.1, 4.9 Hz, 1H), 8.00 (d, J=6.4 Hz, 1H), 7.80 (s, 0.7H), 7.59 (s, 0.3H), 3.68 (m, 4H); $^{13}C$ NMR (101 MHz, $CD_3OD$): δ ppm 168.63, 156.79, 156.41, 148.23, 148.19, 145.46, 142.93, 142.49, 142.41, 139.86, 128.93, 126.90, 126.67, 126.60, 121.13, 33.41, 33.27, 31.72.

(E/Z)-2-(2-(pyridin-4-yl)ethyl)thiazole-4-carbaldehyde oxime hydrochloride NM-130

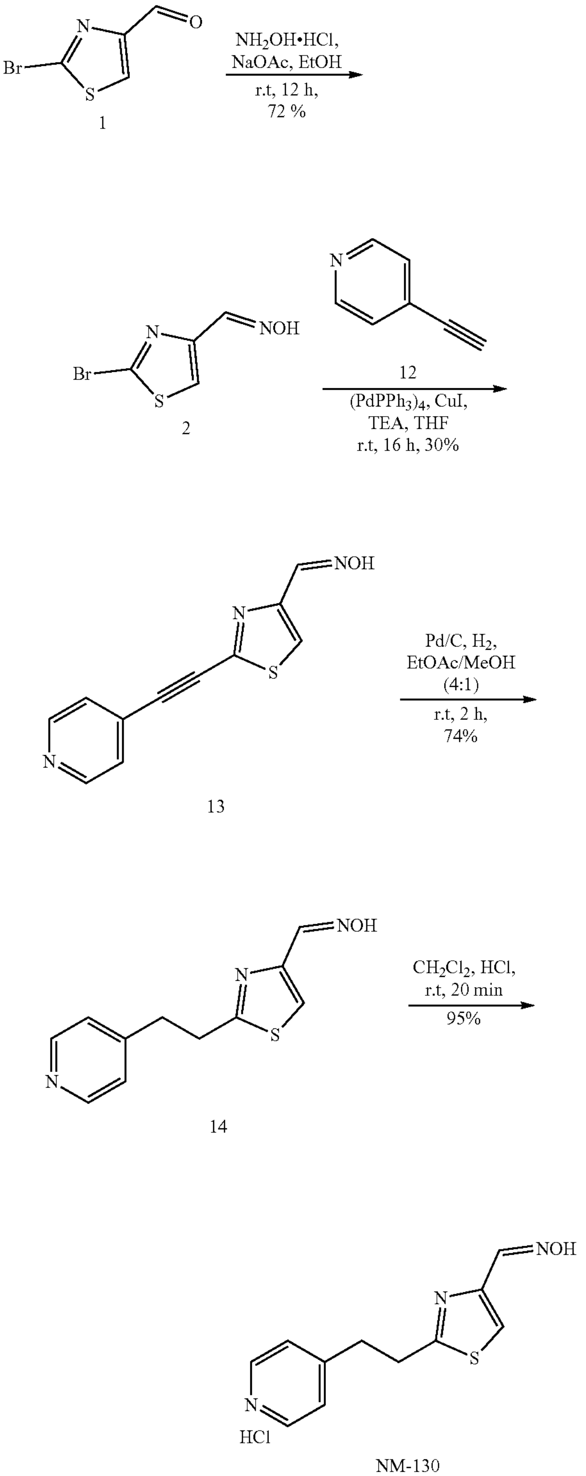

2-(pyridin-4-ylethynyl)thiazole-4-carbaldehyde oxime 13

13

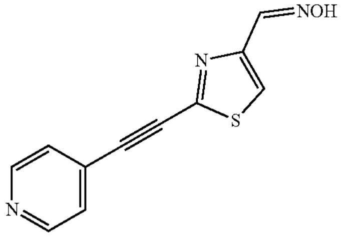

To a degassed solution of (E/Z)-2-bromothiazole-4-carbaldehyde oxime 2 (132 mg, 0.637 mmol, 1.1 equiv) in THF/$Et_3N$ (6 mL/2 mL), Pd$[PPh_3]_4$ (101 mg, 0.087 mmol, 0.15 equiv) and CuI (33 mg, 0.173 mmol, 0.3 equiv) were added. After degassing the reaction mixture for 5 min at room temperature, 4-ethynylpyridine 12 (60 mg, 0.582 mmol, 1 equiv) was added dropwise and the reaction mixture was stirred at the room temperature for 16 h. Upon completion, the reaction mixture was concentrated under reduced pressure and the residue was purified by column chromatography (EtOAc/PE 50:50) to afford cis/trans isomer (6/4 ratio) of (E/Z)-2-(pyridin-4-ylethynyl)thiazole-4-carbaldehyde oxime 13 as off white solid (30 mg, 30%); $R_f$ (50% EtOAc/PE) 0.25; IR (neat): $v_{max}$ 3062, 2715, 2359, 1569, 1497, 1405, 1322, 1099, 994, 978, 925, 820, 701, 571, 542 $cm^{-1}$; HRMS ($ESI^+$): m/z calcd for $C_{11}H_8N_3OS^+$ 230.038259 found 230.038473; $^1H$ NMR (400 MHz, DMSO-$d_6$): δ ppm 12.27 (s, 0.6H), 11.56 (s, 0.4H), 8.73-8.71 (m, 2.6H), 8.24 (s, 0.4H), 8.14 (s, 0.4H), 7.75 (s, 0.6H), 7.69-7.62 (m, 2H); $^{13}C$ NMR (101 MHz, DMSO-$d_6$): δ ppm 150.19, 146.61, 146.01, 145.21, 142.64, 139.00, 131.55, 131.45, 128.84, 128.73, 128.62, 128.19, 121.90, 90.67, 90.63, 85.50, 85.35.

2-(2-(pyridin-4-yl)ethyl)thiazole-4-carbaldehyde oxime 14

14

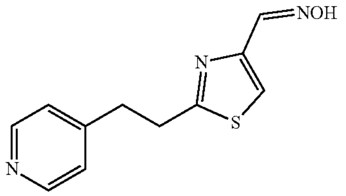

To a solution of (E/Z)-2-(pyridin-4-ylethynyl)thiazole-4-carbaldehyde oxime 13 (20 mg, 0.087 mmol) in 1:1 ratio of EtOAc/MeOH (5 mL) was added 10% Pd/C (20 mg) at room temperature under Argon atmosphere and stirred the mixture for 1 h under $H_2$ atmosphere using balloon pressure. Upon completion, the mixture was filtered using celite pad and concentrated under reduced pressure. the crude was purified by column chromatography (EtOAc/PE, 80:20) to afford cis/trans isomers (5.5/4.5 ratio) of (E/Z)-2-(2-(pyridin-4-yl)ethyl)thiazole-4-carbaldehyde oxime 14 as off white solid (15 mg, 74%); $R_f$ (100% EtOAc) 0.25; IR (neat) $v_{max}$ 2922, 2852, 2359, 1605, 1419, 1189, 1111, 969, 920, 853, 805, 751, 721, 540, 502 $cm^{-1}$; HRMS ($ESI^+$): m/z calcd for $C_{11}H_{12}N_3OS^+$ 234.069559 found 234.069628; $^1$HNMR (400 MHz, $CD_3OD$): δ ppm 8.31 (bs, 2H), 8.28 (s, 0.45H), 8.02 (s, 0.55H), 7.48 (s, 0.55H), 7.47 (s, 0.45H), 7.22 (m, 2H), 3.28 (td, J=7.6, 3.1 Hz, 2H), 3.08 (t, J=7.6 Hz, 2H); $^{13}C$ NMR (101 MHz, $CD_3OD$): δ ppm 171.98, 169.73, 152.18, 150.19, 150.02, 150.02, 146.36, 144.27, 140.70, 126.09, 125.73, 119.32, 35.80, 35.76, 34.19, 33.93.

2-(2-(pyridin-4-yl)ethyl)thiazole-4-carbaldehyde oxime hydrochloride NM-130

NM-130

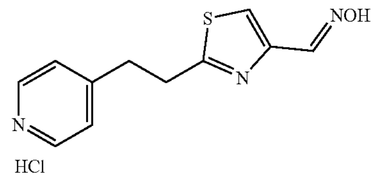

To a solution of (E/Z)-2-(2-(pyridin-4-yl)ethyl)thiazole-4-carbaldehyde oxime 14 (15 mg, 0.064 mmol) was added 2N HCl (2 mL) at room temperature and stirred for 30 min at same temperature. Upon completion, solvent was distilled off under reduced pressure and the resulting solid was washed with diethyl ether (2×4 mL). The solid was dried under vacuum to give cis/trans isomers (7/3 ratio) of (E/Z)-2-(2-(pyridin-4-yl)ethyl)thiazole-4-carbaldehyde oxime hydrochloride NM-130 as a light brown solid (16.5 mg, 95%); IR (neat) $v_{max}$ 3298, 3107, 2989, 2599, 1635, 1304, 1436, 1011, 888, 849, 809, 785, 542 $cm^{-1}$; HRMS ($ESI^+$): m/z calcd for $C_{11}H_{12}N_3OS^+$ 234.069559 found 234.069336; $^1H$ NMR (400 MHz, $CD_3OD$): δ ppm 8.82 (m, 2H), 8.56 (s, 0.3H), 8.21 (s, 0.7H), 8.11 (m, 2H), 7.97 (s, 0.7H), 7.65 (s, 0.3H), 3.82-3.63 (m, 2H), 3.57 (m, 2H); $^{13}C$ NMR (101 MHz, $CD_3OD$): δ ppm 169.68, 162.07, 161.45, 141.16, 141.03, 139.55, 139.53, 136.84, 127.51, 125.85, 120.39, 120.32, 34.57, 34.52, 30.69, 30.35.

2-(2-(pyridin-3-yl)ethyl)thiazole-5-carbaldehyde oxime hydrogen chloride NM-139

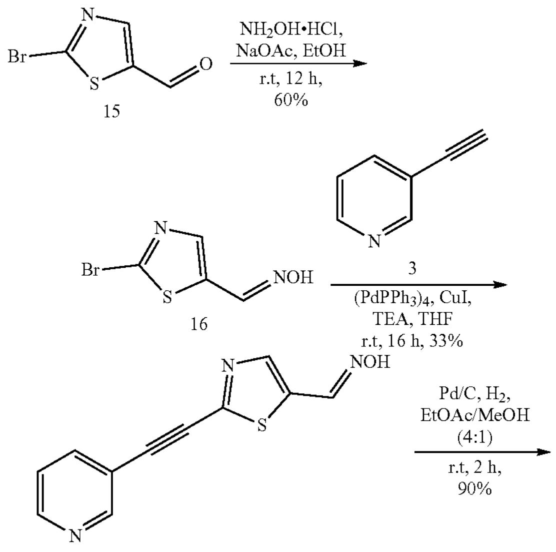

15
16
3
17

-continued

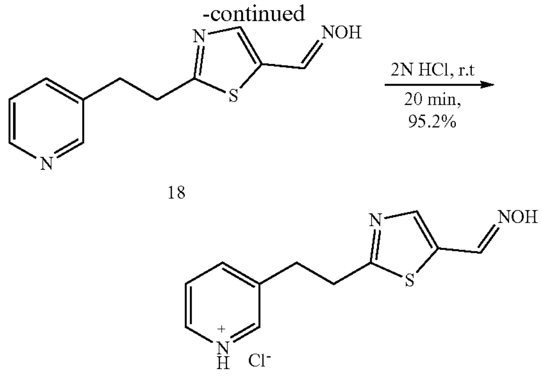

18

NM-139

(E/Z)-2-bromothiazole-4-carbaldehyde oxime 16

16

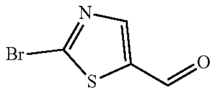

A solution of commercially available 2-bromothiazole-5-carbaldehyde 15 (500 mg, 2.60 mmol, 1 equiv), hydroxylamine hydrochloride (361 mg, 5.19 mmol, 2 equiv), and $CH_3CO_2Na$ (640 mg, 7.80 mmol, 3 equiv) in EtOH (15 mL) was stirred at 80° C. for 12 h. Upon completion, the reaction mixture was filtered through a small celite pad. The filtrate was concentrated under reduced pressure and the residue was purified by column chromatography (EtOAc/PE 1:9) to afford cis/trans isomers (1/0.7 ratio) of (E/Z)-2-bromothiazole-5-carbaldehyde oxime 16 as off white solid (330 mg, 61.2%); $R_f$ (20% EtOAc/PE) 0.45; $^1$H NMR (400 MHz, DMSO-$d_6$): δ ppm 12.50 (s, 1H), 11.68 (s, 0.7H), 8.38 (s, 0.7H), 8.08 (s, 1H), 8.00 (s, 1H), 7.85 (s, 0.7H); $^{13}$C NMR (101 MHz, DMSO-$d_6$): δ ppm 145.81, 143.85, 141.60, 141.28, 137.98, 136.72, 136.69, 129.34.

2-(pyridin-3-ylethynyl)thiazole-5-carbaldehyde oxime 17

17

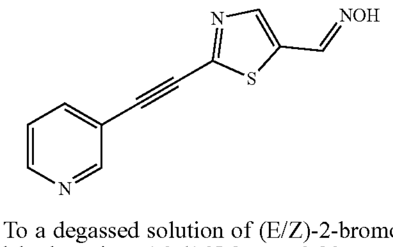

To a degassed solution of (E/Z)-2-bromothiazole-5-carbaldehyde oxime 16 (165.8 mg, 0.80 mmol, 1.1 equiv) in THF/$Et_3N$ (6 mL/2 mL), Pd[$PPh_3$]$_4$ (126.3 mg, 0.109 mmol, 0.15 equiv) and CuI (41.6 mg, 0.218 mmol, 0.3 equiv) were added. After degassing the reaction mixture for 5 min at room temperature, 3-ethynylpyridine 3 (75 mg, 0.728 mmol, 1 equiv) was added dropwise and the reaction mixture was stirred at room temperature for 16 h. Upon completion, the reaction mixture was concentrated under reduced pressure and the residue was purified by column chromatography (EtOAc/PE 50:50) to afford cis/trans isomers (9/1 ratio) of (E/Z)-2-(pyridin-3-ylethynyl)thiazole-5-carbaldehyde oxime 17 as a pale yellow solid (55 mg, 33%); $R_f$ (50% EtOAc/PE) 0.25; IR (neat): $\nu_{max}$ 2665, 2358, 1482, 1410, 1266, 1212, 1110, 927, 889, 839, 805, 692, 625, 590 cm$^{-1}$; HRMS (ESI$^+$): m/z calcd for $C_{11}H_8N_3OS^+$ 230.038259 found 230.037096; $^1$H NMR (400 MHz, DMSO-$d_6$): δ ppm 12.64 (s, 0.9H), 11.78 (s, 0.1H), 8.88 (s, 1H), 8.70 (s, 1H), 8.45 (s, 0.1H), 8.36 (s, 1H), 8.17-8.05 (m, 2H), 7.54 (dd, J=7.8, 4.7 Hz, 1H); $^{13}$C NMR (101 MHz, DMSO-$d_6$): δ ppm 152.42, 150.69, 149.92, 147.63, 139.59, 138.00, 135.19, 127.30, 124.29, 92.69, 85.55.

2-(2-(pyridin-3-yl)ethyl)thiazole-5-carbaldehyde oxime 18

18

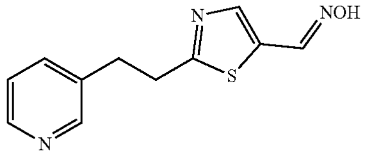

To a solution of (E/Z)-2-(pyridin-3-ylethynyl)thiazole-5-carbaldehyde oxime 17 (25 mg, 0.109 mmol) in 1:1 ratio of MeOH/THF (5 mL) was added 10% Pd/C (20 mg) at room temperature under Argon atmosphere and stirred the mixture for 2 h under $H_2$ atmosphere using balloon pressure. Upon completion, the mixture was filtered through a small celite pad and concentrated under reduced pressure and the crude was purified by column chromatography (EtOAc/PE, 70:30) to afford cis/trans isomers (9/1 ratio) of (E/Z)-2-(2-(pyridin-3-yl)ethyl)thiazole-5-carbaldehyde oxime 18 as white solid (23 mg, 90%); $R_f$ (100% EtOAc/PE) 0.25; IR (neat): $\nu_{max}$ 2996, 2348, 1578, 1480, 1416, 1187, 916, 884, 799, 704, 663, 609 cm$^{-1}$; HRMS (ESI$^+$): m/z calcd for $C_{11}H_{12}N_3OS^+$ 234.069559 found 234.070401; $^1$H NMR (400 MHz, $CD_3OD$): δ ppm 8.39 (bs, 2H), 8.23 (s, 0.1H), 8.00 (s, 0.9H), 7.75 (s, 1H), 7.72 (d, J=7.9 Hz, 1H), 7.36 (s, 1H), 3.37 (t, J=7.7 Hz, 2H), 3.17 (t, J=7.5 Hz, 2H); $^{13}$C NMR (101 MHz, $CD_3OD$): δ ppm 173.88, 148.78, 146.67, 144.99, 142.28, 140.93, 137.54, 137.03, 125.71, 33.29, 32.25.

2-(2-(pyridin-3-yl)ethyl)thiazole-5-carbaldehyde oxime hydrochloride NM-139

NM-139

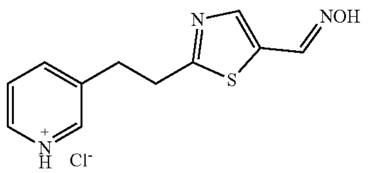

To a solution of (E/Z)-2-(2-(pyridin-3-yl)ethyl)thiazole-4-carbaldehyde oxime 18 (20 mg, 0.06 mmol) in 2N HCl (2 mL) at room temperature and stirred for 20 min at same temperature. Upon completion, solvent was distilled off under reduced pressure and the resulting solid was washed with diethyl ether (2×4 mL). The solid was dried under vacuum to give cis/trans isomers (8/2 ratio) of (E/Z)-2-(2-(pyridin-3-yl)ethyl)thiazole-4-carbaldehyde oxime hydrochloride NM-139 as a light brown solid (22 mg, 95.2%); IR (neat): $\nu_{max}$ 3047, 1555, 1468, 1216, 994, 928, 799, 734, 679, 626 cm$^{-1}$; HRMS (ESI$^+$): m/z calcd for $C_{11}H_{12}N_3OS^+$ 234.06959 found 234.069456; $^1$H NMR (400 MHz, $CD_3OD$): δ ppm 8.95 (bs, 1H), 8.82 (d, J=5.0 Hz, 1H), 8.69 (d, J=7.2 Hz, 1H), 8.47 (s, 0.8H), 8.32 (s, 0.2H), 8.17-8.05 (m, 1.2H), 7.98 (s, 0.8H), 3.81-3.63 (m, 2H), 3.56-3.41 (m, 2H); $^{13}C$ NMR (101 MHz, $CD_3OD$): δ ppm 175.36, 148.62, 142.80, 141.65, 141.44, 141.29, 141.19, 141.01, 139.13, 138.08, 137.34, 128.71, 128.65, 128.52, 128.29, 33.15, 32.88, 32.67, 32.01.

2-(4-(pyridin-3-yl)but-1-yn-1-yl)thiazole-5-carbaldehyde oxime hydrogen chloride NM-141

2-(4-(pyridin-3-yl)butyl)thiazole-5-carbaldehyde oxime hydrogen chloride NM-143

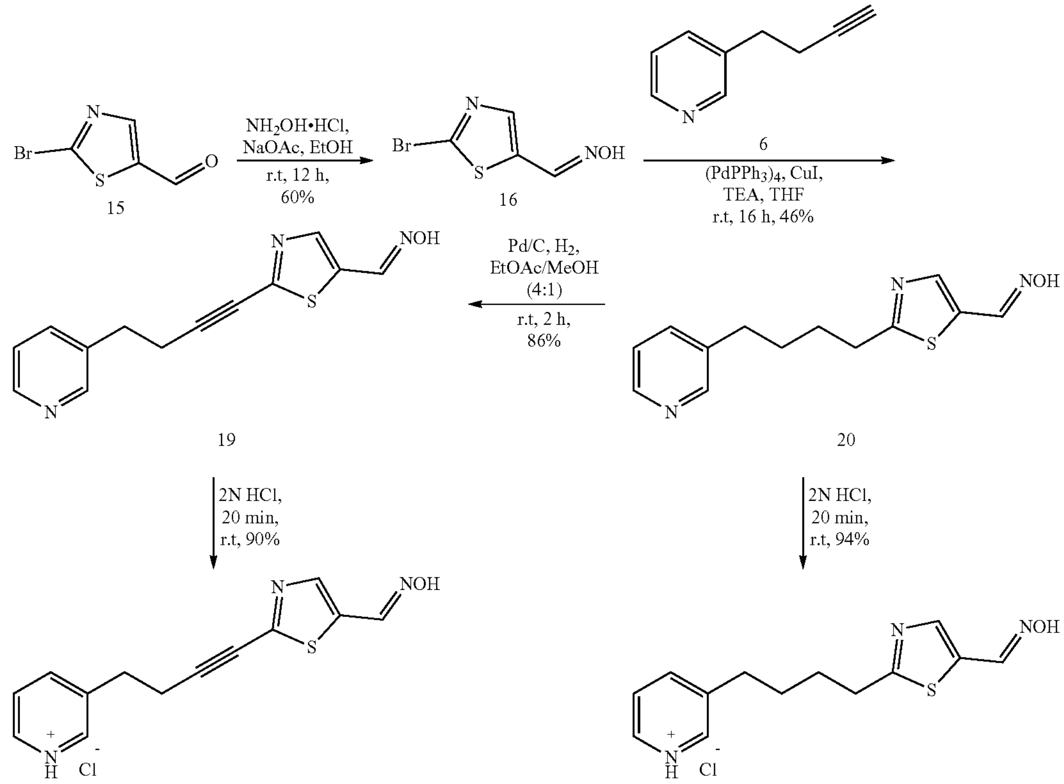

NM-141 NM-143

2-(4-(pyridin-3-yl)but-1-yn-1-yl)thiazole-5-carbaldehyde oxime 19

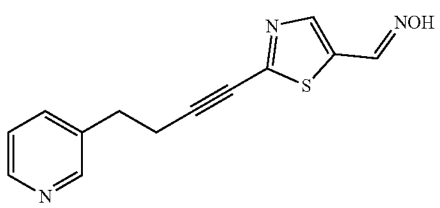

19

To a degassed solution of (E/Z)-2-bromothiazole-5-carbaldehyde oxime 16 (173 mg, 0.835 mmol, 1.1 equiv) in $THF/Et_3N$ (9 mL/3 mL), $Pd[PPh_3]_4$ (132 mg, 0.114 mmol, 0.15 equiv) and CuI (43.6 mg, 0.228 mmol, 0.3 equiv) were added. After degassing the reaction mixture for 5 min at room temperature, 3-(but-3-yn-1-yl)pyridine 6 (100 mg, 0.763 mmol, 1 equiv) was added dropwise and the reaction mixture was stirred at the room temperature for 16 h. Upon completion, the reaction mixture was concentrated under reduced pressure and the residue was purified by column chromatography (EtOAc 100%) to afford cis/trans isomers (95/5 ratio) of (E/Z)-2-(4-(pyridin-3-yl)but-1-yn-1-yl)thiazole-5-carbaldehyde oxime 19 as an off white solid (90 mg, 46%); $R_f$ (100% EtOAc) 0.25; IR (neat): $v_{max}$ 3357, 3160, 2360, 2340, 2224, 1651, 1605, 1411, 1264, 1139, 791, 711, 624 $cm^{-1}$; HRMS ($ESI^+$): m/z calcd for $C_{13}H_{12}N_3OS^+$ 258.069559 found 258.068945; $^1H$ NMR (400 MHz, DMSO-$d_6$): δ ppm 12.45 (s, 0.95H), 11.64 (s, 0.5H), 8.77-8.28 (m, 2H), 8.20 (s, 1H), 8.01 (s, 1H), 7.76 (d, J=7.7 Hz, 1H), 7.44-7.32 (m, 1H), 2.91 (m, 4H); $^{13}C$ NMR (101 MHz, DMSO-$d_6$): δ ppm 151.17, 150.26, 148.25, 148.09, 148.09, 147.07, 138.00, 136.47, 126.15, 98.15, 75.42, 30.98, 21.02.

2-(4-(pyridin-3-yl)but-1-yn-1-yl)thiazole-5-carbaldehyde oxime hydrochloride NM-141

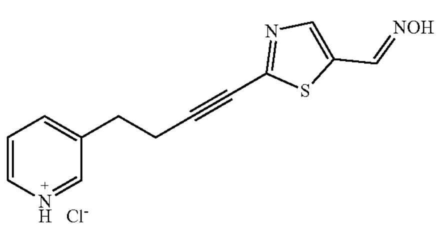

NM-141

To a solution of (E/Z)-2-(4-(pyridin-3-yl)but-1-yn-1-yl) thiazole-5-carbaldehyde oxime 19 (20 mg, 0.077 mmol) was added 2N HCl (2 mL) at room temperature and stirred for 20 min at same temperature. Upon completion, solvent was distilled off under reduced pressure and the resulting solid was washed with diethyl ether (2×4 mL). The solid was dried under vacuum to give cis/trans mixture isomers (7.5/2.5 ratio) of (E/Z)-2-(4-(pyridin-3-yl)but-1-yn-1-yl)thiazole-5-carbaldehyde oxime hydrochloride NM-141 as a light brown solid (20.5 mg, 90%); IR (neat): $v_{max}$ 3004, 2555, 2360, 2341, 1633, 1558, 1263, 1156, 928, 802, 681 $cm^{-1}$; HRMS ($ESI^+$): m/z calcd for $C_{13}H_{13}ClN_3OS^+$ 294.046237 found 294.046258; $^1H$ NMR (400 MHz, $CD_3OD$): δ ppm 8.91 (bs, 1H), 8.78 (bs, 1H), 8.67 (d, J=7.3 Hz, 1H), 8.47 (s, 0.75H), 8.34 (s, 2.5H), 8.12 (bs, 1H), 7.28 (bs, 0.75H), 7.12 (bs, 0.25), 341-3.34 (m, 4H), 3.21 (m, 4H); $^{13}C$ NMR (101 MHz, $CD_3OD$): δ ppm 147.30, 147.24, 145.24, 141.26, 140.58, 139.99, 139.69, 138.01, 127.26, 118.15, 40.39, 40.35, 30.04.

2-(4-(pyridin-3-yl)butyl)thiazole-5-carbaldehyde oxime 20

20

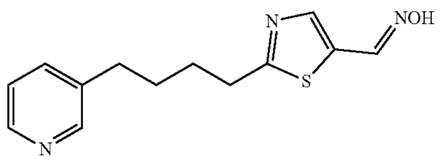

To a solution of (E/Z)-2-(4-(pyridin-3-yl)but-1-yn-1-yl)thiazole-5-carbaldehyde oxime 19 (40 mg, 0.0155 mmol) in 4:1 ratio of EtOAc/MeOH (5 mL) was added 10% Pd/C (40 mg) at room temperature under Argon atmosphere and stirred the mixture for 2 h under $H_2$ atmosphere using balloon pressure. Upon completion, the mixture was filtered through a small celite pad and concentrated under reduced pressure and the crude was purified by column chromatography (EtOAc, 100%) to afford cis/trans isomers (9.4/0.6 ratio) of (E/Z)-2-(4-(pyridin-3-yl)butyl)thiazole-5-carbaldehyde oxime 20 as white solid (35 mg, 86%); $R_f$(100% EtOAc) 0.20; IR (neat): $v_{max}$ 2949, 1578, 1461, 1421, 1188, 1050, 1036, 924, 801, 708, 664, 643, 662 $cm^{-1}$; HRMS ($ESI^+$): m/z calcd for $C_{13}H_{16}N_3OS^+$ 260.100860 found 262.101595; $^1H$ NMR (400 MHz, $CD_3OD$): δ ppm 8.48-8.30 (m, 2H), 8.26 (s, 0.06H) 8.00 (s, 0.94H), 7.78 (s, 0.94H), 7.74 (s, 0.06H) 7.70 (d, J=7.9 Hz, 1H), 7.36 (dd, J=7.7, 4.9 Hz, 1H), 3.08 (t, J=7.4 Hz, 2H), 2.72 (t, J=7.6 Hz, 2H), 1.89-1.82 (m, 2H), 1.78-1.70 (m, 2H); $^{13}C$ NMR (101 MHz, $CD_3OD$): δ ppm 175.68, 148.63, 146.16, 144.88, 138.37, 137.61, 136.88, 125.52, 123.79, 31.91, 31.86, 30.09, 29.02.

2-(4-(pyridin-3-yl)butyl)thiazole-4-carbaldehyde oxime hydrochloride NM-143

NM-143

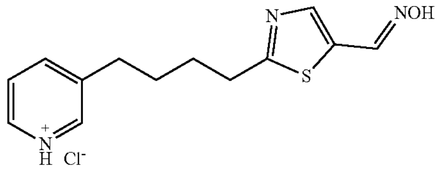

To a solution of (E/Z)-2-(4-(pyridin-3-yl)butyl)thiazole-5-carbaldehyde oxime 20 (30 mg, 0.06 mmol) was added 2N HCl (2.5 mL) at room temperature and stirred for 30 min at same temperature. Upon completion, solvent was distilled off under reduced pressure and the resulting solid was washed with diethyl ether (2×5 mL). The solid was dried under vacuum to give cis/trans isomers (8/2 ratio) of (E/Z)-2-(4-(pyridin-3-yl)butyl)thiazole-5-carbaldehyde oxime hydrochloride NM-143 as a light brown solid (32 mg, 93.8%); IR (neat): $v_{max}$ 2934, 2360, 1555, 1468, 1219, 997, 930, 797, 734, 681 $cm^{-1}$; HRMS ($ESI^+$): m/z calcd for $C_{13}H_{16}N_3OS^+$ 262.100860 found 262.101253; $^1H$ NMR (400 MHz, $CD_3OD$): δ ppm 8.85 (s, 1H), 8.75 (d, J=5.4 Hz, 1H), 8.61 (d, J=7.7 Hz, 1H), 8.55 (s, 0.8H), 8.34 (s, 0.2H), 8.24 (s, 0.2H), 8.08-8.04 (m, 1H), 7.99 (s, 0.8H), 3.48-3.35 (m, 2H), 3.04-2.94 (m, 2H), 2.07-1.81 (m, 4H); $^{13}C$ NMR (101 MHz, $CD_3OD$): δ ppm 178.40, 178.08, 148.40, 144.05, 142.33, 140.48, 140.21, 136.80, 136.27, 136.23, 134.03, 128.50, 128.20, 32.82, 31.48, 30.80, 30.66, 30.62, 29.85, 29.79.

5-(4-(quinolin-4-ylamino)but-1-yn-1-yl)furan-2-carbaldehyde oxime NM-152

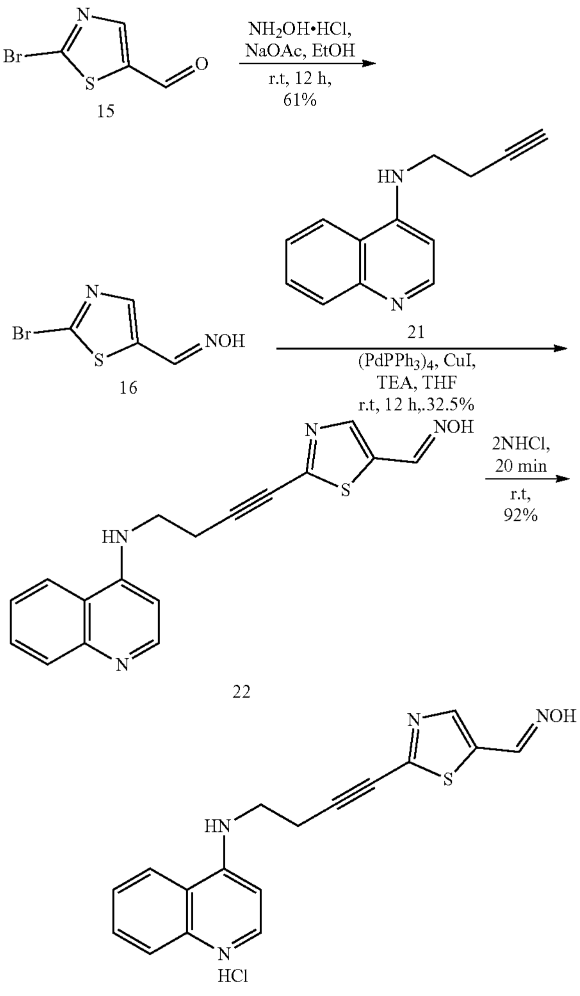

NM-152

2-(4-(quinolin-4-ylamino)but-1-ynyl)thiazole-5-carbaldehyde oxime 22

22

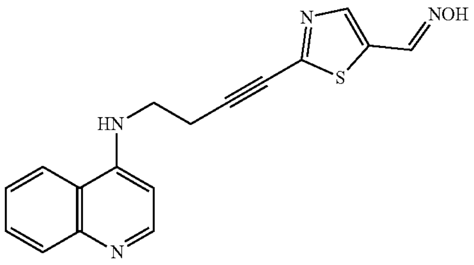

To a degassed solution of (E/Z)-2-bromothiazole-5-carbaldehyde oxime 16 (69 mg, 0.333 mmol, 1.1 equiv) in THF/$Et_3N$ (6 mL/2 mL), Pd[$PPh_3$]$_4$ (53 mg, 0.045 mmol, 0.15 equiv) and CuI (17 mg, 0.0892 mmol, 0.3 equiv) were added. After degassing the reaction mixture for 5 min at room temperature, N-(but-3-yn-1-yl)quinolin-4-amine 21 (60 mg, 0.305 mmol, 1.0 equiv) was added dropwise and the reaction mixture was stirred at the room temperature for 16 h. After completion, the reaction mixture was concentrated under reduced pressure and the residue was purified by column chromatography (MeOH/$CH_2Cl_2$, 10:90) to afford cis-trans isomers (94/6) of (E/Z)-2-(4-(quinolin-4-ylamino)but-1-ynyl)thiazole-5-carbaldehyde oxime 22 as pale yellow solid (32 mg, 32.5%); $R_f$ (10% MeOH/$CH_2Cl_2$) 0.20; HRMS (ESI$^+$): m/z calcd for $C_{17}H_{15}N_4OS^+$ 323.096109 found 323.095000; $^1$H NMR (400 MHz, DMSO-$d_6$): δ ppm 12.46 (s, 0.94H), 11.64 (s, 0.06H), 9.14 (s, 1H), 8.57 (d, J=6.8 Hz, 1H), 8.50 (d, J=8.5 Hz, 1H), 8.38 (s, 0.06H), 8.20 (s, 0.94H), 8.01 (s, 0.94H), 7.98 (s, 0.06H), 7.96-7.86 (m, 2H), 7.71 (ddd, J=8.3, 5.6, 2.6 Hz, 1H), 7.02 (d, J=6.9 Hz, 0.94H), 6.79 (d, J=6.8 Hz, 0.06H), 3.92-3.80 (m, 2H), 3.03 (t, J=6.7 Hz, 2H); $^{13}$C NMR (101 MHz, DMSO-$d_6$): δ ppm 155.29, 150.95, 147.05, 144.08, 139.63, 137.94, 133.43, 126.86, 126.28, 123.25, 121.91, 117.37, 99.01, 96.24, 75.87, 41.47, 19.55.

2-(4-(quinolin-4-ylamino)but-1-ynyl)thiazole-5-carbaldehyde oxime hydrochloride NM-152

NM-152

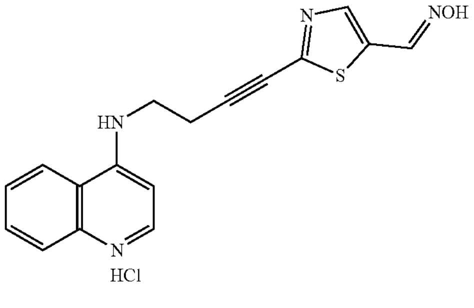

To a solution of (E/Z)-2-(4-(quinolin-4-ylamino)but-1-ynyl)thiazole-5-carbaldehyde oxime 22 (20 mg, 0.062 mmol) was added 2N HCl (2 mL) at room temperature and stirred for 20 min at same temperature. Upon completion, solvent was distilled off under reduced pressure and the resulting solid was washed with diethyl ether (2×4 mL). The solid was dried under vacuum to give cis-trans mixture of (E/Z)-2-(4-(quinolin-4-ylamino)but-1-ynyl)thiazole-5-carbaldehyde oxime hydrochloride as a light brown solid NM-152 (20.5 mg, 92%); HRMS (ESI$^+$): m/z calcd for $C_{17}H_{15}N_4OS^+$ 323.096109 found 323.0951581; $^1$H NMR (400 MHz, $CD_3OD$): δ ppm 8.59-8.31 (m, 2.5H), 8.26-8.05 (m, 0.5H), 8.03-7.81 (m, 2.5H), 7.80-7.59 (m, 1H), 7.44 (bs, 0.5H), 7.15-6.94 (m, 1H), 4.07 (s, 2H), 3.34 (d, 2H); $^{13}$C NMR (101 MHz, $CD_3OD$): δ ppm 156.39, 145.43, 144.72, 144.46, 142.32, 139.78, 137.88, 137.54, 136.18, 133.72, 133.58, 127.11, 126.85, 122.67, 122.33, 119.82, 119.68, 118.57, 117.07, 98.47, 98.43, 41.33, 41.29, 39.24, 39.19.

2-(4-(quinolin-4-ylamino)but-1-ynyl)thiazole-4-carbaldehyde hydrochloride NM-176

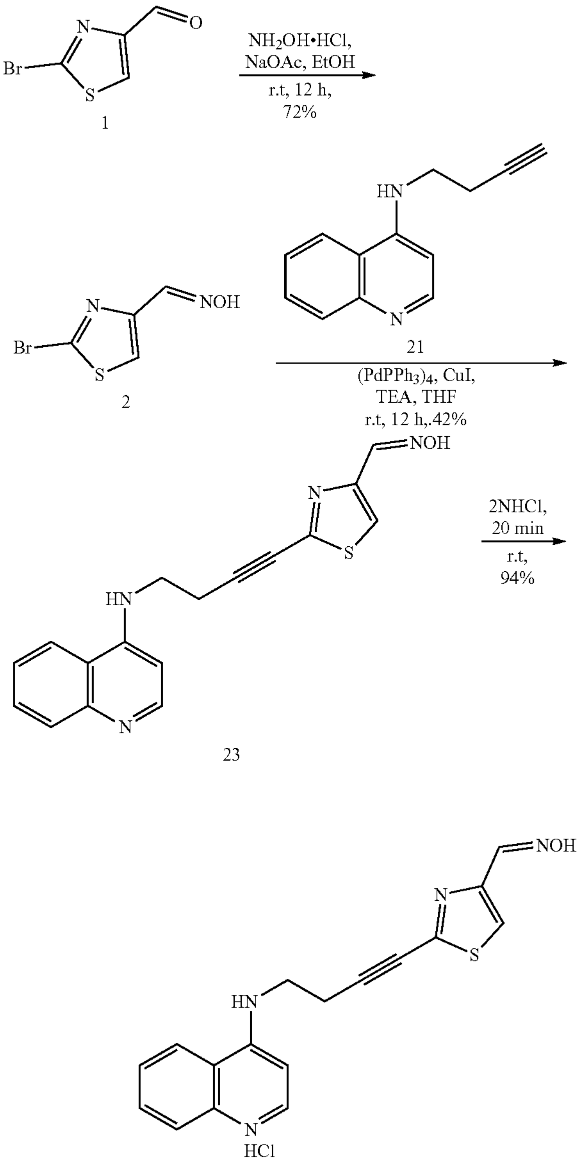

NM-176

2-(4-(quinolin-4-ylamino)but-1-ynyl)thiazole-4-carbaldehyde oxime 23

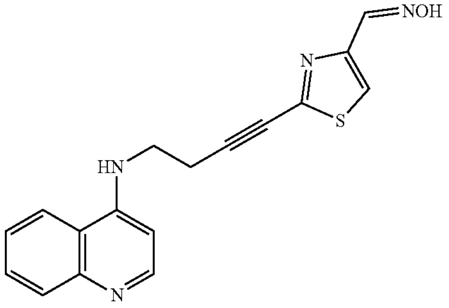

23

To a degassed solution of (E/Z)-2-bromothiazole-4-carbaldehyde oxime 2 (69 mg, 0.570 mmol, 1.1 equiv) in THF/$Et_3N$ (6 mL/2 mL), $Pd[PPh_3]_4$ (53 mg, 0.0778 mmol, 0.15 equiv) and CuI (17 mg, 0.155 mmol, 0.3 equiv) were added. After degassing the reaction mixture for 5 min at room temperature, N-(but-3-yn-1-yl)quinolin-4-amine 15 (100 mg, 0.519 mmol, 1.0 equiv) was added dropwise and the reaction mixture was stirred at the room temperature for 16 h. After completion, the reaction mixture was concentrated under reduced pressure and the residue was purified by column chromatography (MeOH/$CH_2Cl_2$, 10:90) to afford cis-trans isomers (7.5/2.5) of (E/Z)-2-(4-(quinolin-4-ylamino)but-1-ynyl)thiazole-5-carbaldehyde oxime 23 as a pale yellow solid (32 mg, 42%); $R_f$ (10% MeOH/$CH_2Cl_2$) 0.20; IR (neat): $v_{max}$ 3281, 3054, 2360, 2235, 1579, 974, 724 $cm^{-1}$; HRMS ($ESI^+$): m/z calcd for $C_{17}H_{15}N_4OS^+$ 323.096109 found 323.0957321; $^1H$ NMR (400 MHz, DMSO-$d_6$): δ ppm 12.17 (s, 0.75H), 11.45 (s, 0.25H), 8.52 (s, 0.75H), 8.44 (s, 0.75H), 8.22 (d, J=8.3 Hz, 1H), 8.15 (s, 0.25H), 7.92 (s, 0.25H), 7.81 (d, J=8.0 Hz, 1H), 7.69-7.58 (m, 2H), 7.53-7.39 (m, 2H), 6.62 (d, J=5.1 Hz, 1H), 3.63 (dd, J=12.7, 6.6 Hz, 2H), 2.94 (t, J=6.8 Hz, 2H); $^{13}C$ NMR (101 MHz, DMSO-$d_6$): δ ppm 150.81, 150.15, 149.74, 148.60, 147.13, 145.68, 143.17, 139.55, 129.43, 129.23, 127.19, 124.55, 122.09, 120.39, 95.40, 75.19, 74.98, 41.15, 19.41, 19.37.

2-(4-(quinolin-4-ylamino)but-1-ynyl)thiazole-4-carbaldehyde oxime hydrochloride NM-176

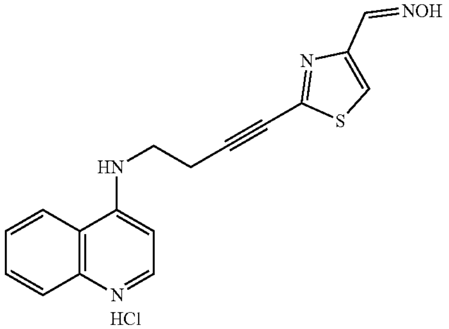

NM-176

To a solution of (E/Z)-2-(4-(quinolin-4-ylamino)but-1-ynyl)thiazole-4-carbaldehyde oxime 23 (20 mg, 0.062 mmol) was added 2N HCl (2 mL) at room temperature and stirred for 20 min at same temperature. Upon completion, solvent was distilled off under reduced pressure and the resulted solid was washed with diethyl ether (2×4 mL). The solid was dried under vacuum to give cis-trans mixture of (E/Z)-2-(4-(quinolin-4-ylamino)but-1-ynyl)thiazole-4-carbaldehyde oxime hydrochloride NM-176 as a light brown solid (21 mg, 94%); IR (neat): $v_{max}$ 3186, 3098, 2828, 1608, 1592, 1564, 1447, 1350, 1219, 759 $cm^{-1}$; HRMS ($ESI^+$): m/z calcd for $C_{17}H_{15}N_4OS^+$ 323.096109 found 323.0959331; $^1H$ NMR (400 MHz, $CD_3OD$): δ ppm 8.53-8.37 (m, 2.25H), 8.18-7.80 (m, 2.75H), 7.73 (dd, J=17.0, 8.5 Hz, 1H), 7.64-7.49 (m, 0.5H), 7.45-7.22 (m, 0.5H), 7.12-6.95 (m, 1H), 4.09-3.90 (m, 2H), 3.23 (dt, J=16.4, 6.5 Hz, 1H), 3.13-3.00 (m, 1H); $^{13}C$ NMR (101 MHz, $CD_3OD$): δ ppm 156.59, 156.43, 142.15, 142.04, 141.98, 141.98, 141.94, 137.92, 137.88, 133.67, 133.67, 127.05, 127.01, 122.53, 122.46, 119.78, 117.07, 117.00, 98.33, 98.30, 41.28, 41.14, 19.12, 18.99.

4-(2-(pyridin-3-yl)ethyl)thiazole-2-carbaldehyde oxime hydrochloride NM-171

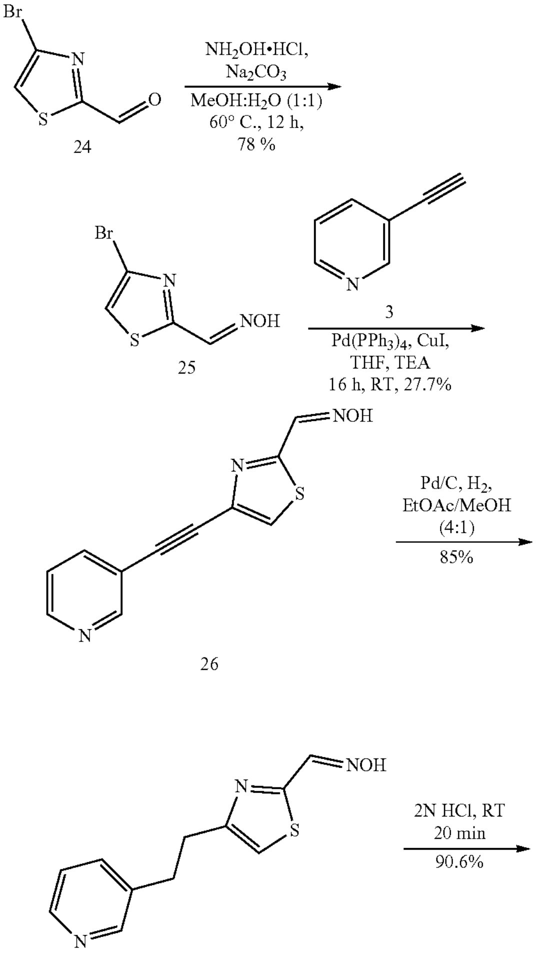

24
25
3
26
27

-continued

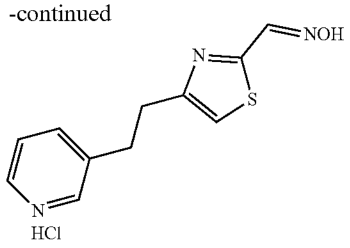

NM-171

4-bromothiazole-2-carbaldehyde oxime 25

25

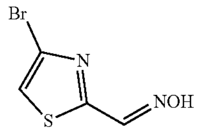

A solution of commercially available 4-bromothiazole-2-carbaldehyde 24 (1 g, 5.20 mmol, 1 equiv), hydroxylamine hydrochloride (723 mg, 10.40 mmol, 2 equiv) and $Na_2CO_3$ (1.655 g, 15.61 mmol, 3 equiv) in 1:1 ratio of $MeOH/H_2O$ (20 mL) was stirred at 60° C. for 2 h. Upon completion, the reaction mixture was concentrated under reduced pressure and 30 mL of water was added. The mixture was extracted with EtOAc (2×30 mL), dried over anhydrous $Na_2SO_4$, concentrated under reduced pressure and the residue was purified by column chromatography (EtOAc/PE 2:8) to afford cis-trans isomers (1/0.66) of (E/Z)-4-bromothiazole-2-carbaldehyde oxime 25 as an off white solid (824 mg, 78%); $R_f$ (20% EtOAc/PE) 0.35; $^1$H NMR (400 MHz, Acetone-$d_6$): δ ppm 12.19 (s, 1H), 11.28 (s, 0.66H), 8.29 (d, J=0.8 Hz, 0.66H), 7.93 (d, J=0.8 Hz, 1H), 7.90 (d, J=1.0 Hz, 1H), 7.65 (d, J=0.8 Hz, 0.66H); $^{13}$C NMR (101 MHz, Acetone-$d_6$): δ ppm 143.50, 139.97, 126.00, 125.10, 122.16, 118.46.

4-(pyridin-3-ylethynyl)thiazole-2-carbaldehyde oxime 26

26

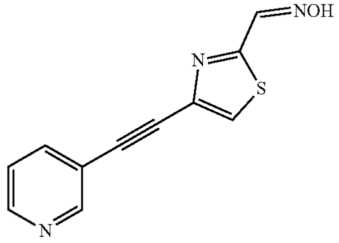

To a degassed solution of (E/Z)-4-bromothiazole-2-carbaldehyde oxime 25 (165.8 mg, 0.80 mmol, 1.1 equiv) in $THF/Et_3N$ (9 mL/3 mL), $Pd[PPh_3]_4$ (126.3 mg, 0.109 mmol, 0.15 equiv) and CuI (41.6 mg, 0.109 mmol, 0.3 equiv) were added. After degassing the reaction mixture for 5 min at room temperature, 3-ethynylpyridine 3 (75 mg, 0.728 mmol, 1 equiv) was added dropwise and the reaction mixture was stirred at the room temperature for 16 h. Upon completion, the reaction mixture was concentrated under reduced pressure and the residue was purified by column chromatography (EtOAc/PE 50:50) to give cis-trans isomers (7/3, ratio) of (E/Z)-4-(pyridin-3-ylethynyl)thiazole-2-carbaldehyde oxime 26 as an off white solid (46 mg, 27.7%); $R_f$ (50% EtOAc/PE) 0.25; IR (neat): $v_{max}$ 3061, 2918, 1566, 1494, 1407, 1007, 799, 697, 639, 539 $cm^{-1}$; HRMS ($ESI^+$): m/z calcd for $C_{11}H_8N_3OS^+$ 230.038259 found 230.039853; $^1$H NMR (400 MHz, Acetone-$d_6$): δ ppm 8.79 (s, 1H), 8.64 (dd, J=9.3, 8.0 Hz, 1H), 8.33 (d, J=0.8 Hz, 0.7H), 8.20 (d, J=0.9 Hz, 0.3H), 8.03-7.92 (m, 2H), 7.47 (dd, J=7.5, 5.2 Hz, 1H); $^{13}$C NMR (101 MHz, Acetone-$d_6$): δ ppm 162.24, 151.94, 149.33, 143.92, 143.83, 138.42, 137.26, 128.16, 124.98, 123.41, 119.30, 86.13, 85.35.

2-(2-(pyridin-3-yl)ethyl)thiazole-4-carbaldehyde oxime 27

27

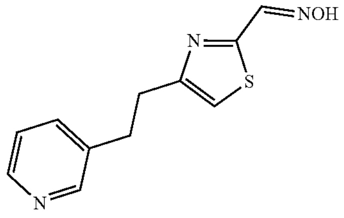

To a solution of (E/Z)-4-(pyridin-3-ylethynyl)thiazole-2-carbaldehyde oxime 26 (20 mg, 0.087 mmol) in EtOAc (3 mL) was added 10% Pd/C (10 mg) at room temperature under Argon atmosphere and stirred the mixture for 1 h under $H_2$ atmosphere using balloon pressure. Upon completion, the mixture was filtered through a small celite pad, concentrated under reduced pressure followed by column chromatography (10% $MeOH/CH_2Cl_2$) to afford (E/Z)-4-(2-(pyridin-3-yl)ethyl)thiazole-4-carbaldehyde oxime 27 as an off white solid (17.3 mg, 85%). $R_f$ (100% EtOAc) 0.20. $^1$H NMR (400 MHz, $CD_3OD$): δ 8.42-8.30 (m, 2H), 8.24 (d, J=1.0 Hz, 0.3H), 7.86 (d, J=1.0 Hz, 0.7H), 7.71-7.66 (m, 1H), 7.40-7.31 (m, 1.7H), 7.09-7.07 (m, 0.3H), 3.20-3.05 (m, 4H). $^{13}$C NMR (101 MHz, $CD_3OD$): δ 162.73, 155.94, 155.22, 154.62, 148.73, 148.61, 146.36, 146.13, 143.17, 139.68, 138.54, 137.47, 137.45, 136.99, 136.83, 123.73, 119.09, 115.04, 32.06, 32.02, 31.94, 31.90.

4-(2-(pyridin-3-yl)ethyl)thiazole-2-carbaldehyde oxime hydrochloride NM-171

NM-171

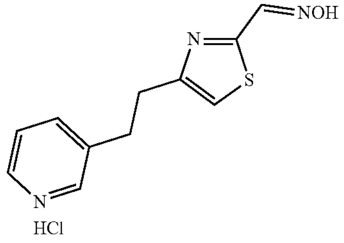

To a solution of (E/Z)-4-(2-(pyridin-3-yl)ethyl)thiazole-2-carbaldehyde oxime 27 (11 mg, 0.085 mmol) in $CH_2Cl_2$ (3 ml) was added 2N HCl (1 mL) at room temperature and stirred for 30 min at same temperature. Upon completion, solvent was distilled off under reduced pressure and the resulting solid was washed with diethyl ether (2×3 mL). The solid was dried under vacuum to give mixture of cis-trans isomers (1/1, ratio) of (E/Z)-4-(2-(pyridin-3-yl)ethyl)thiazole-2-carbaldehyde oxime hydrochloride NM-171 as a light brown solid (11.5 mg, 90.6%); HRMS ($ESI^+$): m/z calcd for $C_{11}H_{12}N_3OS^+$ 234.0696 found 234.0694; $^1H$ NMR (400 MHz, $CD_3OD$): δ ppm 8.93-8.69 (m, 2H), 8.61 (d, J=7.0 Hz, 1H), 8.14 (s, 0.5H), 8.08 (bs, 1H), 7.83 (s, 0.5H), 7.70-7.55 (m, 1H), 3.55-3.33 (m, 4H); $^{13}C$ NMR (101 MHz, $CD_3OD$): δ ppm 149.31, 147.19, 141.38, 141.27, 141.27, 141.14, 139.57, 138.88, 135.87, 132.44, 132.42, 131.73, 131.63, 128.67, 128.55, 127.21, 127.15, 121.58, 31.17, 31.14, 29.66, 29.08.

2-(2-(pyridin-3-yl)ethyl)oxazole-4-carbaldehyde oxime NM-168

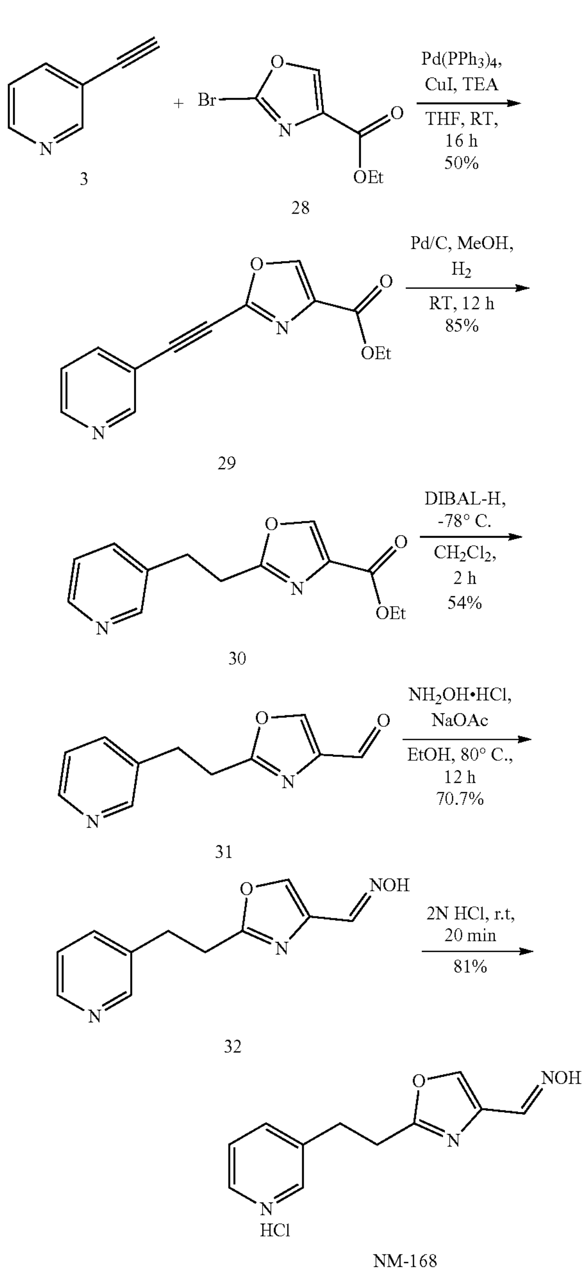

3, 28, 29, 30, 31, 32, NM-168

Ethyl 2-(pyridin-3-ylethynyl)oxazole-4-carboxylate 29

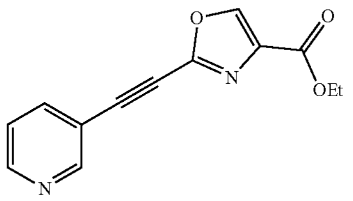

29

To a degassed solution of ethyl 2-bromooxazole-4-carboxylate 28 (470 mg, 2.135 mmol, 1.1 equiv) in THF/$Et_3N$ (12 mL/4 mL), $Pd[PPh_3]_4$ (336 mg, 0.290 mmol, 0.15 equiv) and CuI (110 mg, 0.577 mmol, 0.3 equiv) were added. After degassing the reaction mixture for 5 min at room temperature, 3-ethynylpyridine 3 (200 mg, 1.941 mmol, 1 equiv) was added dropwise and the reaction mixture was stirred at the room temperature for 16 h. Upon completion, the reaction mixture was concentrated under reduced pressure and the residue was purified by column chromatography (EtOAc/PE, 1:1) to afford ethyl 2-(2-(pyridin-3-yl)ethyl)oxazole-4-carboxylate 29 as an off white solid (220 mg, 46.8%); $R_f$(50% EtOAc/PE) 0.35; IR (neat): $\nu_{max}$ 3148, 2922, 2852, 2360, 2228, 1731, 1543, 1330, 1307, 1174, 1148, 1107, 812, 771, 702 $cm^{-1}$; HRMS ($ESI^+$): m/z calcd for $C_{13}H_{10}N_2NaO_3^+$ 265.058363 found 265.059171; $^1H$ NMR (400 MHz, $CDCl_3$): δ ppm 8.85 (bs, 1H), 8.68 (bs, 1H), 8.28 (s, 1H), 7.90 (d, J=7.9 Hz, 1H), 7.37 (dd, J=7.5, 5.0 Hz, 1H), 4.43 (q, J=7.1 Hz, 2H), 1.42 (t, J=7.1 Hz, 3H); $^{13}C$ NMR (101 MHz, $CDCl_3$): δ ppm 160.38, 152.74, 150.42, 146.63, 144.53, 139.17, 134.71, 89.04, 79.17, 77.34, 77.02, 76.71, 61.58, 14.26.

Ethyl 2-(2-(pyridin-3-yl)ethyl)oxazole-4-carboxylate 30

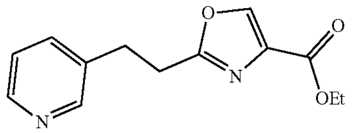

30

To a solution of ethyl 2-(2-(pyridin-3-yl)ethyl)oxazole-4-carboxylate 29 (120 mg, 0.495 mmol) in MeOH (10 mL) was added 10% Pd/C (60 mg) at room temperature under Argon atmosphere and stirred the mixture for 12 h under $H_2$ atmosphere using balloon pressure. Upon completion, the mixture was filtered through a small celite pad, concentrated under reduced pressure and purified by $SiO_2$ column chromatography (EtOAc/PE, 70:30) ethyl 2-(2-(pyridin-3-yl)ethyl)oxazole-4-carboxylate 30 as a light brown syrup (91 mg, 74.6%); $R_f$(50% EtOAc+PE) 0.3; IR (neat): $\nu_{max}$ 3134, 3092, 2990, 1717, 1583, 1314, 1165, 1024, 780, 715 $cm^{-1}$; HRMS ($ESI^+$): m/z calcd for $C_{13}H_{14}N_2NaO_3^+$ 269.089663 found 269.089903; $^1H$ NMR (400 MHz, $CDCl_3$): δ ppm 8.42 (bs, 2H), 8.12 (s, 1H), 7.50 (dd, J=6.2, 1.6 Hz, 1H), 7.21 (dd, J=7.7, 4.8 Hz, 1H), 4.36 (q, J=7.1 Hz, 2H), 3.12 (bs, 4H), 1.36 (t, J=7.1 Hz, 3H); $^{13}C$ NMR (101 MHz, $CDCl_3$): δ ppm 164.16, 161.16, 149.72, 148.08, 143.73, 135.70, 135.12, 133.52, 123.49, 61.18, 30.09, 29.48, 14.28.

2-(2-(pyridin-3-yl)ethyl)oxazole-4-carbaldehyde oxime 32

32

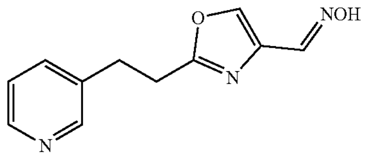

To a solution of ethyl 2-(2-(pyridin-3-yl)ethyl)oxazole-4-carboxylate 30 (80 mg, 0324 mmol, 1 equiv) in $CH_2Cl_2$ (4 mL) was added DIBAL-H (0.8 mL, 1M in THF, 0.809 mmol, 2.5 equiv) at −78° C. and stirred over 2 h at same temperature. The mixture was quenched with MeOH (2 mL) at −78° C. and concentrated under reduced pressure. The white aluminum salts were removed by filtered in $CH_2Cl_2$, concentrated under reduced pressure and purified by column chromatography to give 2-(2-(pyridin-3-yl)ethyl)oxazole-4-carbaldehyde 31 as an off white solid (22 mg, 53.6% w.r.t SM, 30 mg SM recovered). $^1H$ NMR (400 MHz, $CDCl_3$): δ 9.92 (s, 1H), 8.50 (d, J=2.3 Hz, 2H), 8.19 (d, J=4.4 Hz, 1H), 7.57-7.53 (m, 1H), 7.25 (dd, J=7.8, 4.2 Hz, 1H), 3.18 (s, 4H). To a solution of 2-(2-(pyridin-3-yl)ethyl)oxazole-4-carbaldehyde 31 (20 mg, 0.0989 mmol, 1 equiv) in EtOH (5 mL) was added hydroxylamine hydrochloride (13.7 mg, 0.1971 mmol, 2 equiv), NaOAc (24.34 mg, 2.429 mmol, 3 equiv) and refluxed for 16 h. After concentration under reduced pressure, the crude product was purified by $SiO_2$ column chromatography (100% EtOAc) to afford cis-trans isomers of (8/2, ratio) of (E/Z)-2-(2-(pyridin-3-yl)ethyl)oxazole-4-carbaldehyde oxime 32 as an off white solid (15.2 mg, 70.7%); $R_f$ (100% EtOAc) 0.35; HRMS ($ESI^+$): m/z calcd for $C_{11}H_{12}N_3O_2^+$ 218.092403 found 218.091853; $^1H$ NMR (400 MHz, $CDCl_3$): δ ppm 8.51 (bs, 2H), 8.43 (s, 0.8H), 8.06 (s, 0.2H), 7.77 (s, 0.2H), 7.61-7.50 (m, 1.8H), 7.28-7.23 (m, 1H), 3.17 (bs, 4H); $^{13}C$ NMR (101 MHz, $CDCl_3$): δ ppm 162.59, 149.53, 147.74, 143.02, 136.16, 135.52, 123.64, 30.07, 29.28.

2-(2-(pyridin-3-yl)ethyl)oxazole-4-carbaldehyde oxime hydrochloride NM-168

NM-168

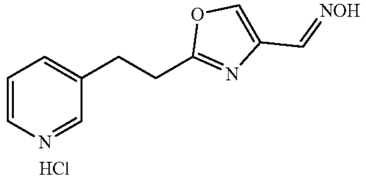

To a solution of ((E/Z)-2-(2-(pyridin-3-yl)ethyl)oxazole-4-carbaldehyde oxime 32 (13.5 mg, 0.062 mmol) in $CH_2Cl_2$ (2 ml) was added 2N HCl (2 mL) at room temperature and stirred for 20 min at same temperature. Upon completion, solvent was distilled off under reduced pressure and the resulting solid was washed with diethyl ether (2×3 mL). The solid was dried under vacuum to give (E)-2-(2-(pyridin-3-yl)ethyl)oxazole-4-carbaldehyde oxime hydrochloride NM-168 as an off white solid (12.8 mg, 81.3%); $^1H$ NMR (400 MHz, $CD_3OD$): δ ppm 8.88 (s, 1H), 8.77 (d, J=5.7 Hz, 1H), 8.63 (d, J=8.1 Hz, 1H), 8.52 (s, 1H), 8.07 (dd, J=8.0, 5.8 Hz, 1H), 7.37 (s, 1H), 3.42 (t, J=7.0 Hz, 2H), 3.32-3.27 (m, 2H); $^{13}C$ NMR (101 MHz, $CD_3OD$): δ ppm 162.42, 147.09, 143.08, 141.33, 141.23, 141.16, 139.44, 137.95, 127.03, 28.69, 27.33.

(E/Z)-4-(4-(pyridin-3-yl)butyl)thiazole-2-carbaldehyde oxime hydrochloride-260

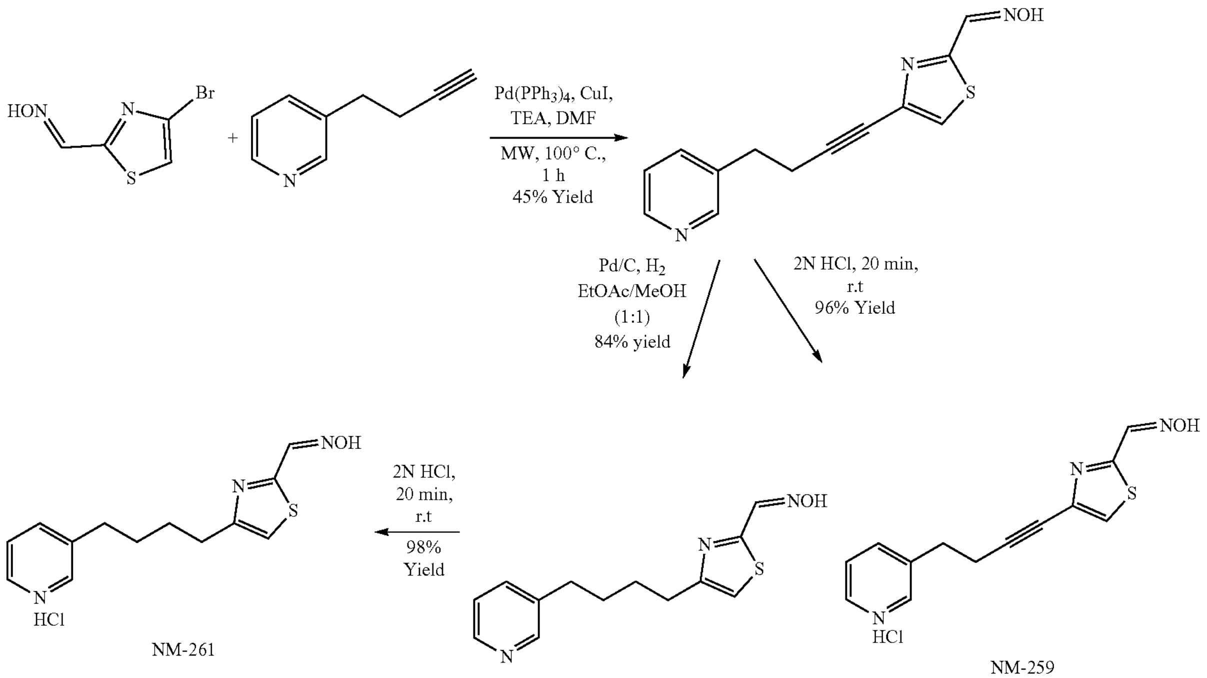

NM-261 NM-260 NM-259

(E/Z)-4-(4-(pyridin-3-yl)but-1-yn-1-yl)thiazole-2-carbaldehyde oxime

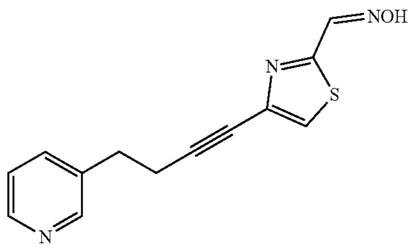

To a degassed solution of (E/Z)-4-bromothiazole-2-carbaldehyde oxime (150 mg, 0.724 mmol, 1 equiv) in DMF/$Et_3N$ (9 mL/3 mL), $Pd[PPh_3]_4$ (167.6 mg, 0.144 mmol, 0.20 equiv) and CuI (55.18 mg, 0.289 mmol, 0.4 equiv) were added. After degassing the reaction mixture for 5 min at r.t, 3-(but-3-yn-1-yl)pyridine 6 (113.9 mg, 0.869 mmol, 1 equiv) was added to the mixture and the reaction mixture was subjected to microwave irradiation at 100° C. for 1 h. Upon completion, the reaction mixture was concentrated under reduced pressure and the residue was purified by column chromatography (EtOAc/PE 70:30) to afford cis/trans isomers (5.5/4.5 ratio) of (E/Z)-4-(4-(pyridin-3-yl)but-1-yn-1-yl)thiazole-2-carbaldehyde oxime as an off white solid (85 mg, 46%). $R_f$ (100% EtOAc) 0.30; IR (neat): $v_{max}$ 2831, 1684, 1481, 1436, 1181, 1118, 992, 719, 693, 536 $cm^{-1}$; HRMS ($ESI^+$): m/z calcd for $C_{13}H_{12}N_3OS^+$ 258.069559 found 258.067707. $^1H$ NMR (400 MHz, $CDCl_3$): δ 8.87-8.43 (m, 2H), 8.31 (s, 0.55), 7.95 (s, 0.45H) 7.70-7.62 (m, 1H), 7.52 (s, 0.45H), 7.38-7.28 (m, 1H), 7.24 (s, 0.55), 3.02-2.89 (m, 2H), 2.81-2.68 (m, 2H). $^{13}C$ NMR (101 MHz, $CDCl_3$): δ 161.87, 154.10, 149.47, 149.43, 147.00, 146.92, 144.38, 140.62, 137.86, 137.24, 137.18, 137.09, 136.66, 136.25, 132.11, 126.49, 125.88, 123.95, 122.59, 88.87, 88.75, 31.74, 29.70, 21.36, 21.30.

(E/Z)-4-(4-(pyridin-3-yl)but-1-yn-1-yl)thiazole-2-carbaldehyde oxime hydrochloride NM-259

NM-259

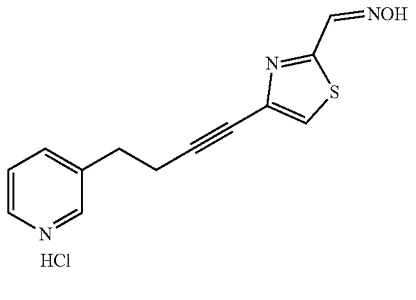

To a solution of (E/Z)-4-(4-(pyridin-3-yl)but-1-yn-1-yl) thiazole-2-carbaldehyde oxime (11 mg, 0.042 mmol) was added 2N aq.HCl (2 mL) at room temperature and stirred for 20 min at same temperature. Upon completion, solvent was distilled off under reduced pressure and the resulting solid was washed with diethyl ether (2×3 L). The solid was dried under vacuum to give cis/trans mixture (6/4 ratio) of (E/Z)-4-(4-(pyridin-3-yl)but-1-yn-1-yl)thiazole-2-carbaldehyde oxime hydrochloride NM-259 as an off white solid (14 mg, 94%). IR (neat): $v_{max}$ 3071, 2985, 2360, 2340, 1156, 1395, 1043, 1002, 930, 908, 830, 727, 682, 514 $cm^{-1}$; HRMS ($ESI^+$): m/z calcd for $C_{13}H_{12}N_3OS^+$ 258.069559 found 258.068295. $^1H$ NMR (400 MHz, $CD_3OD$): δ 8.98-8.91 (bs, 1H), 8.83-8.78 (m, 1H), 8.75-8.68 (m, 1H), 8.21 (s, 0.4H), 8.15-8.08 (m, 1H), 7.88 (s, 0.6H), 7.87 (s, 0.6H), 7.63 (s, 0.4H), 3.27-3.19 (m, 2H), 3.00-2.91 (m, 2H). $^{13}C$ NMR (101 MHz, $CD_3OD$): δ 162.92, 154.27, 147.33, 142.37, 141.24, 141.20, 139.51, 138.51, 136.71, 127.05, 126.61, 123.26, 88.76, 88.16, 75.71, 75.47, 30.58, 19.46, 19.44.

(E/Z)-4-(4-(pyridin-3-yl)butyl)thiazole-2-carbaldehyde oxime

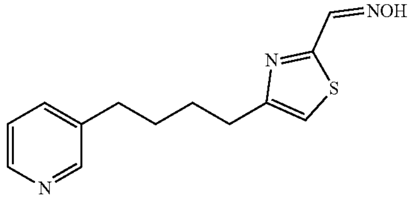

To a solution of (E/Z)-4-(4-(pyridin-3-yl)but-1-yn-1-yl) thiazole-2-carbaldehyde oxime (20 mg, 0.116 mmol) in 3:1 ratio of EtOAc/MeOH (5 mL) was added 10% Pd/C (20 mg) at r.t under Argon atmosphere and stirred the mixture for 2 h under $H_2$ atmosphere using balloon pressure. Upon completion, the mixture was filtered using celite pad, concentrated under reduced pressure and purified by column chromatography to afford cis/trans isomers (1/1 ratio) of ((E/Z)-4-(4-(pyridin-3-yl)butyl)thiazole-2-carbaldehyde oxime as an off white solid (25 mg, 87%). $R_f$(100% EtOAc) 0.3; IR (neat): $v_{max}$ 3012, 2929, 2853, 1577, 1505, 1459, 1419, 1225, 1188, 906, 758, 703, 642 $cm^{-1}$; HRMS ($ESI^+$): m/z calcd for $C_{13}H_{16}N_3OS^+$ 262.100860 found 260.100262. 1H NMR (400 MHz, $CDCl_3$): δ 8.46 (s, 2H), 8.38 (s, 0.05H), 8.02 (d, J=1.0 Hz, 1H), 7.57-7.54 (m, 1H), 7.30-7.23 (m, 1H), 7.12 (d, J=0.9 Hz, 1H), 6.83 (d, J=0.9 Hz, 0.05H), 2.87 (t, J=7.4 Hz, 2H), 2.67 (t, J=7.6 Hz, 2H), 1.85-1.60 (m, 4H). $^{13}C$ NMR (101 MHz, $CDCl_3$): δ 162.17, 157.59, 156.77, 154.74, 148.94, 146.35, 144.63, 140.74, 138.22, 136.92, 123.76, 117.80, 113.98, 32.79, 31.01, 30.95, 30.54, 30.49, 29.70, 28.86, 28.66.

(E/Z)-4-(4-(pyridin-3-yl)butyl)thiazole-2-carbaldehyde oxime hydrochloride NM-261

NM-261

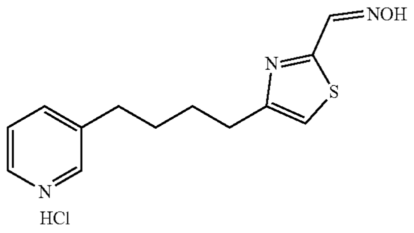

To a solution of (E/Z)-4-(4-(pyridin-3-yl)butyl)thiazole-2-carbaldehyde oxime (20 mg, 0.076 mmol) was added 2N HCl (2 mL) at r.t and stirred for 30 min at same temperature. Upon completion, solvent was distilled off under reduced pressure and the resulting solid was washed with diethyl ether. The solid was dried under vacuum to give cis/trans mixture (8/2 ratio) of (E/Z)-4-(4-(pyridin-3-yl)butyl)thiazole-2-carbaldehyde oxime hydrochloride NM-261 as an off white solid (22 mg, 96%). IR (neat): $v_{max}$ 3381, 3114, 3045, 2937, 2360, 1620, 1466, 1114, 967, 942 $cm^{-1}$; HRMS ($ESI^+$): m/z calcd for $C_{13}H_{16}N_3OS^+$ 262.100860 found 262.099918. 1H NMR (400 MHz, Methanol-d4): δ 8.86 (s, 1H), 8.76 (d, J=5.5 Hz, 1H), 8.62 (d, J=7.9 Hz, 1H), 8.48 (s, 0.2H), 8.29 (s, 0.8H), 8.09-8.06 (m, 1H), 8.00 (s, 0.8H), 7.75 (s, 0.2H), 3.08-2.99 (m, 4H), 2.01-1.72 (m, 4H). 13C NMR (101 MHz, MeOD) δ 153.76, 148.73, 146.99, 143.00, 142.96, 140.89, 139.02, 138.48, 133.72, 127.08, 121.60, 31.61, 31.59, 29.31, 27.62, 27.56, 27.18.

(E/Z)-2-(2-(pyrimidin-2-yl)ethyl)thiazole-4-carbaldehyde oxime hydrochloride NM-250

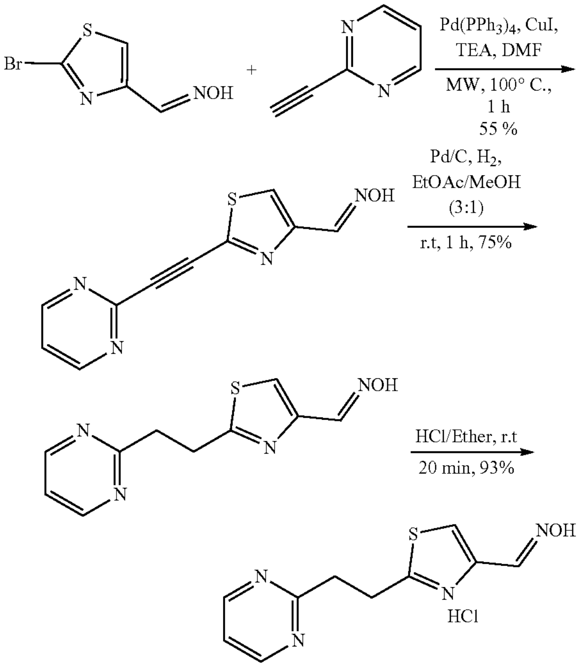

NM-250

(E/Z)-2-(pyrimidin-2-ylethynyl)thiazole-4-carbaldehyde oxime

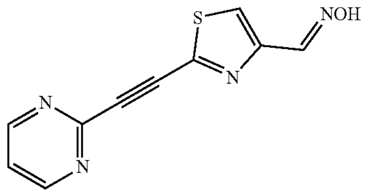

To a degassed solution of (E/Z)-2-bromothiazole-4-carbaldehyde oxime (100 mg, 0.483 mmol, 1.0 equiv) in DMF/$Et_3N$ (6 mL/2 mL), $Pd[PPh_3]_4$ (101 mg, 0.096 mmol, 0.2 equiv) and CuI (36.8 mg, 0.1931 mmol, 0.4 equiv) were added. After degassing the reaction mixture for 5 min at room temperature, 2-ethynylpyrimidine (60.35 mg, 0.579 mmol, 1.2 equiv) was added dropwise and the reaction mixture was subjected to microwave irradiation at 100° C. for 1 h. Upon completion, the reaction mixture was concentrated under reduced pressure and the residue was purified by column chromatography (EtOAc/PE 50:50) to afford cis/trans isomer (1:0.25 ratio) of (E/Z)-2-(pyrimidin-2-ylethynyl)thiazole-4-carbaldehyde oxime as off white solid (60 mg, 55%). IR (neat): $v_{max}$ 3174, 3042, 2918, 2850, 2359, 1546, 1406, 1282, 1182, 1118, 1082, 711, 691, 640, 539 $cm^{-1}$; $R_f$ (50% EtOAc/PE) 0.25; HRMS ($ESI^+$): m/z calcd for $C_{10}H_7N_4OS^+$ 231.033508 found 231.033347. $^1H$ NMR (400 MHz, DMSO-$d_6$): δ 12.27 (s, 1H), 11.15 (s, 0.25H), 9.29 (s, 1.25H), 9.15 (s, 2.5H), 8.73 (s, 1H), 8.24 (s, 0.25), 8.12 (s, 0.25), 7.75 (s, 1H). $^{13}C$ NMR (101 MHz, DMSO-$d_6$): δ 160.61, 159.75, 159.73, 158.25, 150.64, 147.05, 146.43, 145.66, 143.10, 139.46, 128.98, 122.22, 117.70, 88.24, 88.08, 87.79.

(E/Z)-2-(2-(pyrimidin-2-yl)ethyl)thiazole-4-carbaldehyde oxime

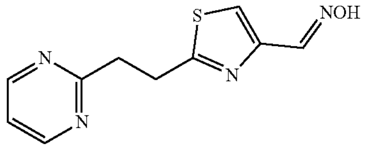

To a solution of (E/Z)-2-(pyrimidin-2-ylethynyl)thiazole-4-carbaldehyde oxime (20 mg, 0.086 mmol) in 3:1 ratio of EtOAc/MeOH (5 mL) was added 10% Pd/C (20 mg) at r.t under Argon atmosphere and stirred the mixture for 1 h under $H_2$ atmosphere using balloon pressure. Upon completion, the mixture was filtered using celite pad and concentrated under reduced pressure. the crude was purified by preparative TLC to afford cis/trans isomers (1/1 ratio) of (E)-2-(2-(pyrimidin-2-yl)ethyl)thiazole-4-carbaldehyde oxime as an off white solid (15 mg, 75%). $R_f$ (100% EtOAc) 0.25; IR (neat): $v_{max}$ 3150, 2852, 2360, 1567, 1448, 1411, 1096, 959, 914, 741, 722, 643 $cm^{-1}$; HRMS ($ESI^+$) m/z calcd for $C_{10}H_{11}N_4OS^+$ 235.064808 found 235.065823. $^1H$ NMR (400 MHz, Methanol-$d_4$) δ 9.01 (d, J=2.3 Hz, 1H), 8.70 (s, 2H), 8.42 (s, 0.5H), 8.14 (s, 0.5H), 7.60 (d, J=11.3 Hz, 1H), 3.45-3.40 (m, 2H), 3.22 (t, J=7.5 Hz, 2H). $^{13}C$ NMR (101 MHz, MeOD): δ 170.13, 167.87, 156.96, 156.94, 155.98, 148.89, 142.86, 139.30, 134.39, 124.80, 118.11, 32.94, 32.67, 29.49, 29.47.

(E/Z)-2-(2-(pyrimidin-2-yl)ethyl)thiazole-4-carbaldehyde oxime hydrochloride NM-250

NM-250

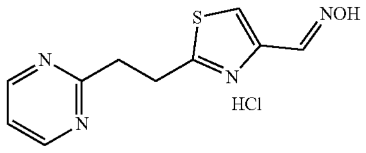

To a solution of (E/Z)-2-(2-(pyridin-4-yl)ethyl)thiazole-4-carbaldehyde oxime 14 (15 mg, 0.064 mmol) was added 2N HCl/Ether (2 mL) at r.t and stirred for 20 min at same temperature. Upon completion, solvent was distilled off under reduced pressure and the resulting solid was washed with diethyl ether. The solid was dried under vacuum to give cis/trans isomers (7/3 ratio) of (E/Z)-2-(2-(pyridin-4-yl) ethyl)thiazole-4-carbaldehyde oxime hydrochloride NM-130 as a light brown solid (16 mg, 93%). IR (neat): $v_{max}$ 3415, 2924, 2360, 1569, 1435, 1411, 913, 788, 720, 644, 456 $cm^{-1}$; HRMS (ESI$^+$) m/z calcd for $C_{10}H_{11}N_4OS^+$ 235.064808 found 235.065442. $^1H$ NMR (400 MHz, $CD_3OD$): δ 9.19 (d, J=3.4 Hz, 1H), 8.95 (d, J=4.0 Hz, 2H), 8.35 (s, 0.35), 8.06 (bs, 0.65H), 7.65 (s, 0.65H), 7.48 (s, 0.35H), 3.45-3.39 (m, 2H), 3.33-3.22 (m, 2H). $^{13}C$ NMR (101 MHz, $CD_3OD$): δ 171.40, 168.10, 157.21, 152.77, 152.51, 147.50, 147.00, 144.18, 141.62, 140.83, 138.61, 135.84, 135.50, 125.19, 118.52, 31.85, 31.82, 29.12, 29.08.

(E/Z)-2-(4-phenylbutyl)thiazole-4-carbaldehyde oxime hydrochloride NM-247

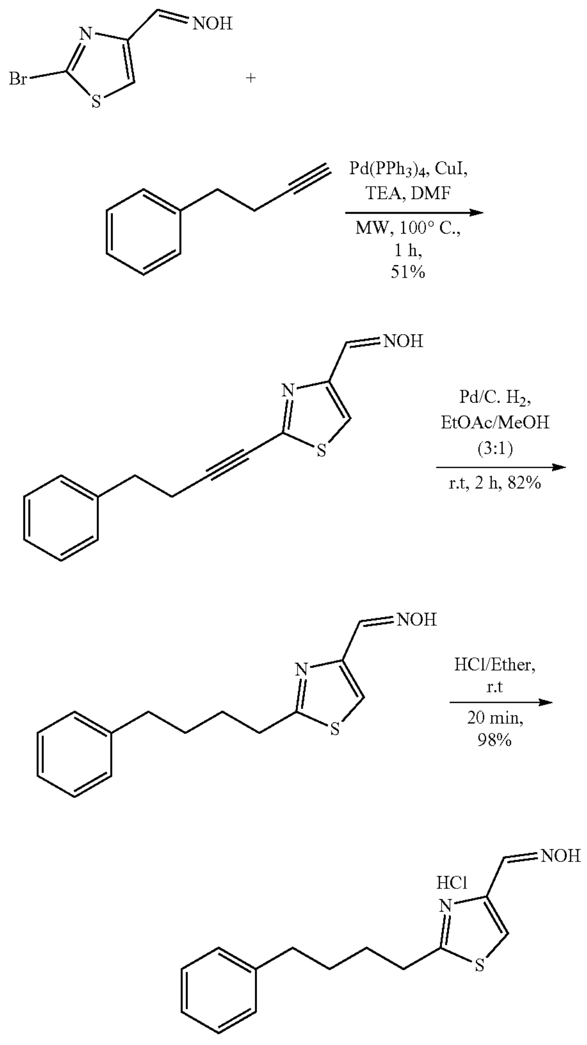

NM-247

(E/Z)-2-(4-phenylbut-1-yn-1-yl)thiazole-4-carbaldehyde oxime

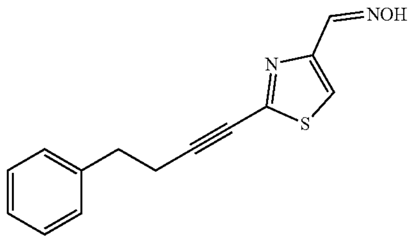

To a degassed solution of (E/Z)-2-bromothiazole-4-carbaldehyde oxime 2 (150 mg, 0.724 mmol, 1 equiv) in THF/$Et_3N$ (6 mL/2 mL), Pd[$PPh_3$]$_4$ (167 mg, 0.144 mmol, 0.2 equiv) and CuI (55 mg, 0.288 mmol, 0.4 equiv) were added. After degassing the reaction mixture for 5 min at r.t, but-3-yn-1-ylbenzene (113 mg, 0.867 mmol, 1.2 equiv) was added dropwise and the reaction mixture was subjected to microwave irradiation at 100° C. for 1 h. Upon completion, the reaction mixture was concentrated under reduced pressure and the residue was purified by column chromatography (EtOAc/PE 30:70) to afford cis/trans isomers (1/1 ratio) of (E/Z)-2-(4-phenylbut-1-yn-1-yl)thiazole-4-carbaldehyde oxime as an off white solid (95 mg, 51%). IR (neat): $v_{max}$ 3158, 3057, 2938, 2855, 2360, 2340, 1488, 1457, 1257, 1132, 982, 888, 731, 700, 505 $cm^{-1}$; $R_f$(30% EtOAc/PE) 0.30; HRMS (ESI$^+$) m/z calcd for $C_{14}H_{13}N_2OS^+$ 257.074310 found 257.071919. $^1H$ NMR (400 MHz, $CDCl_3$): δ 8.21 (bs, 1H), 7.72 (s, 0.5H), 7.44 (s, 0.5H), 7.44-7.19 (m, 2H), 7.20-7.11 (m, 3H), 2.91-2.86 (m, 2H), 2.71-2.66 (m, 2H). $^{13}C$ NMR (101 MHz, $CDCl_3$): δ 149.84, 148.67, 148.18, 144.35, 140.42, 139.96, 139.91, 128.58, 128.56, 128.43, 126.62, 126.58, 126.25, 96.85, 96.64, 74.40, 74.10, 34.28, 21.77.

(E/Z)-2-(4-phenylbutyl)thiazole-4-carbaldehyde oxime

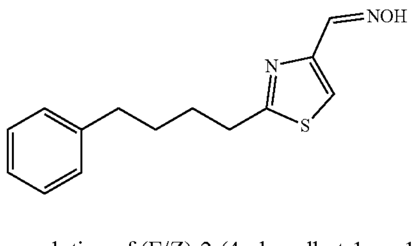

To a solution of (E/Z)-2-(4-phenylbut-1-yn-1-yl)thiazole-4-carbaldehyde oxime (30 mg, 0.117 mmol) in 3:1 ratio of EtOAc/MeOH (5 mL) was added 10% Pd/C (10 mg) at room temperature under Argon atmosphere and stirred the mixture for 2 h under $H_2$ atmosphere using balloon pressure. Upon completion, the mixture was filtered using celite pad, concentrated under reduced pressure and purified by column chromatography (EtOAc/PE), 40:60 to afford cis/trans isomers (1/1 ratio) of (E/Z)-2-(4-phenylbutyl)thiazole-4-carbaldehyde oxime as an off white solid (25 mg, 82%). $R_f$(30% EtOAc/PE) 0.20; IR (neat): $v_{max}$ 3158, 3023, 2919, 2853, 1488, 1458, 1257, 1179, 1131, 754, 699 $cm^{-1}$; HRMS (ESI$^+$): m/z calcd for $C_{14}H_{17}N_2OS^+$ 261.105611 found 260. 261.103834. 1H NMR (400 MHz, $CDCl_3$): δ 8.13 (s, 0.5H), 7.95 (s, 0.5H), 7.64 (s, 0.5H), 7.29 (s, 0.5H), 7.24-7.14 (m, 2H), 7.14-7.00 (m, 3H), 3.00-2.96 (m, 2H), 2.61-2.56 (m, 2H), 1.83-1.60 (m, 5H). $^{13}C$ NMR (101 MHz, $CDCl_3$): δ 172.53, 170.70, 148.14, 145.33, 144.31, 142.02, 141.92, 140.13, 128.40, 128.39, 128.35, 125.88, 125.83, 123.89, 118.27, 35.51, 33.32, 32.95, 30.78, 30.72, 29.71, 29.54, 29.39.

(E/Z)-2-(4-phenylbutyl)thiazole-4-carbaldehyde oxime hydrochloride NM-247

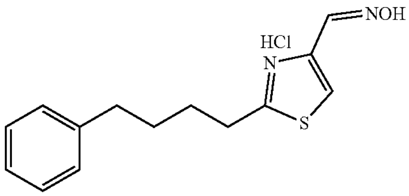

NM-247

To a solution of (E/Z)-2-(4-phenylbutyl)thiazole-4-carbaldehyde oxime (25 mg, 0.06 mmol) was added 2N HCl/Ether (2 mL) at r.t and stirred for 20 min at same temperature. Upon completion, solvent was distilled off under reduced pressure and the resulting solid was washed with diethyl ether. The solid was dried under vacuum to give cis/trans mixture (7.3/2.7 ratio) of (E/Z)-2-(4-phenylbutyl)thiazole-4-carbaldehyde oxime hydrochloride as a light brown solid (28 mg, 98%). IR (neat): $v_{max}$ 3098, 3050, 2332, 1871, 1491, 1454, 1331, 1002, 935, 749, 701, 502 $cm^{-1}$; HRMS ($ESI^+$): m/z calcd for $C_{14}H_{17}N_2OS^+$ 261.105611 found 260. 261.105488. $^1H$ NMR (400 MHz, $CD_3OD$): δ 8.54 (s, 0.27H), 8.19 (s, 0.73H), 7.94 (s, 0.73H), 7.61 (s, 0.27H), 7.34-7.11 (m, 5H), 3.28-3.18 (m, 2H), 2.72-3.68 (m, 2H), 1.94-1.69 (m, 4H). $^{13}C$ NMR (101 MHz, $CD_3OD$): δ 173.66, 141.71, 141.59, 139.00, 136.14, 128.04, 128.01, 125.57, 125.52, 125.25, 34.87, 34.80, 31.02, 30.43, 30.39, 28.94.

(E/Z)-2-(2-(pyridin-2-yl)ethyl)thiazole-5-carbaldehyde oxime hydrochloride NM-204

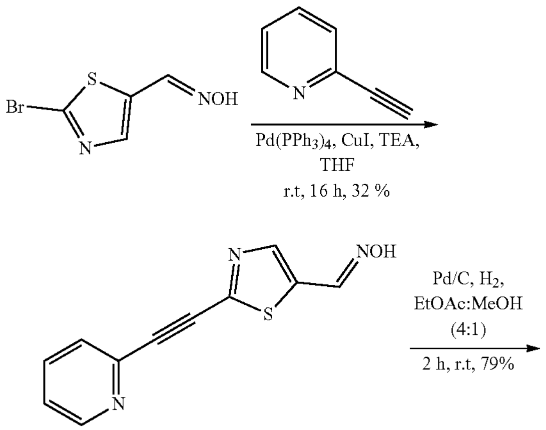

-continued

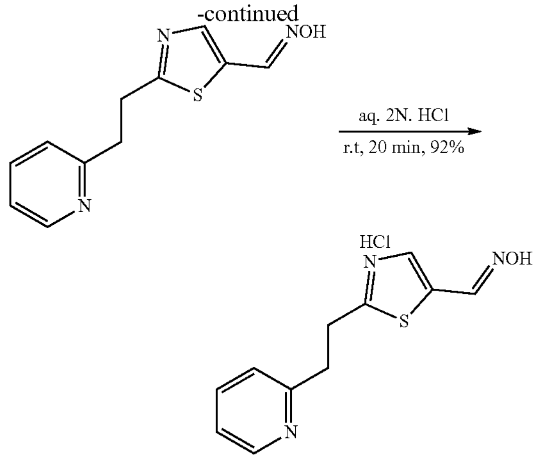

NM-204

(E/Z)-2-(pyridin-2-ylethynyl)thiazole-5-carbaldehyde oxime

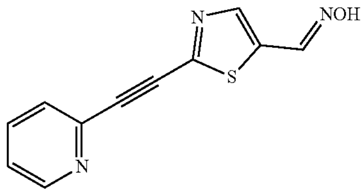

To a degassed solution of (E/Z)-2-bromothiazole-5-carbaldehyde oxime (132 mg, 0.637 mmol, 1 equiv) in THF/$Et_3N$ (6 mL/2 mL), $Pd[PPh_3]_4$ (101 mg, 0.087 mmol, 0.15 equiv) and CuI (33 mg, 0.173 mmol, 0.3 equiv) were added. After degassing the reaction mixture for 5 min at room temperature, 2-ethynylpyridine (60 mg, 0.582 mmol, 1 equiv) was added dropwise and the reaction mixture was stirred at room temperature for 16 h. Upon completion, the reaction mixture was concentrated under reduced pressure and the residue was purified by column chromatography (EtOAc/PE 50:50) to afford cis/trans isomer of (E/Z)-2-(pyridin-2-ylethynyl)thiazole-5-carbaldehyde oxime as a light yellow solid. ESI-MS: m/z 230.05.

(E/Z)-2-(2-(pyridin-2-yl)ethyl)thiazole-5-carbaldehyde oxime

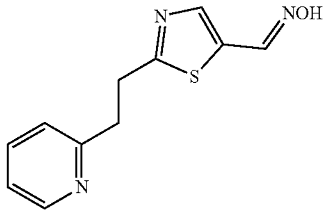

To a solution of (E/Z)-2-(pyridin-2-ylethynyl)thiazole-5-carbaldehyde oxime (25 mg, 0.109 mmol) in 4:1 ratio of EtOAc/MeOH (5 mL) was added 10% Pd/C (20 mg) at r.t under Argon atmosphere and stirred the mixture for 1 h under $H_2$ atmosphere using balloon pressure. Upon completion, the mixture was filtered using small celite pad and concentrated under reduced pressure. The crude was purified by preparative TLC to afford cis/trans isomers (9.4/0.6 ratio) of (E/Z)-2-(2-(pyridin-2-yl)ethyl)thiazole-5-carbaldehyde oxime as lite yellow solid (20 mg, 79%). $R_f$ (100% EtOAc) 0.25; HRMS (ESI$^+$) m/z calcd for $C_{11}H_{12}N_3OS^+$ 234.069559 found 234.069337. $^1$H NMR (400 MHz, $CD_3OD$): δ 8.50-8.47 (m, 1H), 8.00 (s, 1H), 7.79-7.71 (m, 2H), 7.34-7.24 (m, 2H), 3.47 (t, J=7.6 Hz, 2H), 3.30 (t, J=7.6 Hz, 2H). $^{13}$C NMR (101 MHz, $CD_3OD$): δ 174.25, 159.35, 148.49, 144.97, 142.23, 137.58, 137.38, 125.67, 123.53, 121.89, 36.93, 36.81, 32.46, 32.02.

(E/Z)-2-(2-(pyridin-2-yl)ethyl)thiazole-5-carbaldehyde oxime hydrochloride NM-204

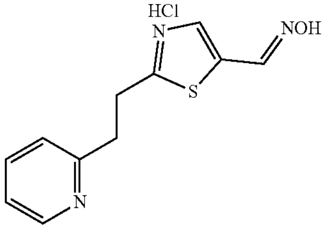

NM-204

To a solution of (E/Z)-2-(2-(pyridin-2-yl)ethyl)thiazole-5-carbaldehyde oxime (15 mg, 0.064 mmol) was added aq. 2N HCl (2 mL) at r.t and stirred for 20 min at same temperature. Upon completion, solvent was distilled off under reduced pressure and the resulting solid was washed with diethyl ether (2×3 mL). The solid was dried under vacuum to give cis/trans isomers (8/2 ratio) of (E/Z)-2-(2-(pyridin-2-yl)ethyl)thiazole-5-carbaldehyde oxime hydrochloride NM-204 as a light yellow solid (16 mg, 92%). HRMS (ESI$^+$) m/z calcd for $C_{11}H_{12}N_3OS^+$ 234.069559 found 234.069252. $^1$H NMR (400 MHz, Methanol-d4): δ 8.87-8.80 (m, 1H), 8.66-8.58 (m, 1H), 8.41 (s, 0.8H), 8.31 (s, 0.2H), 8.16-8.09 (m, 1H), 8.07-7.98 (m, 1.2H), 7.96 (s, 0.8H), 3.88-3.63 (m, 4H). $^{13}$C NMR (101 MHz, MeOD) δ 172.72, 154.17, 147.09, 141.37, 139.11, 136.21, 127.50, 125.54, 31.93, 29.25.

(E/Z)-2-phenethylthiazole-4-carbaldehyde oxime hydrochloride FR-78

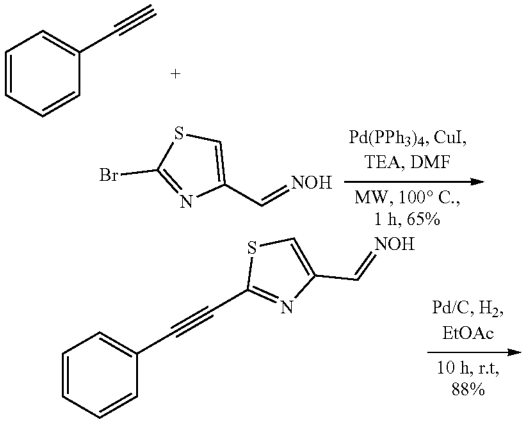

-continued

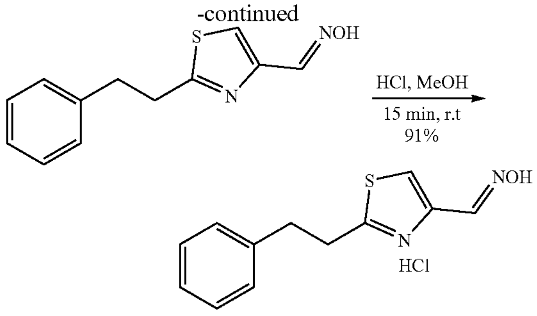

FR-78

(E/Z)-2-(phenylethynyl)thiazole-4-carbaldehyde oxime FR-72

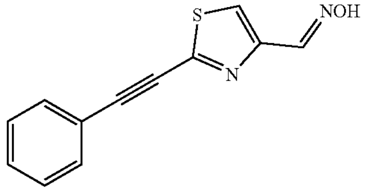

To a degassed solution of (E/Z)-2-bromothiazole-4-carbaldehyde oxime (80 mg, 0.386 mmol, 1 equiv) in DMF/$Et_3N$ (8 mL/2 mL), Pd[$PPh_3$]$_4$ (89.3 mg, 0.077 mmol, 0.2 equiv) and CuI (29.44 mg, 0.154 mmol, 0.4 equiv) were added. After degassing the reaction mixture for 5 min at room temperature, the ethynylbenzene, (47.36 mg, 0.463 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/Pentane 1:5) to afford cis/trans isomers (0.56/0.44 ratio) of (E/Z)-2-(phenylethynyl)thiazole-4-carbaldehyde oxime as off white solid (57 mg, 65%). $R_f$ (20% EA/Pentane) 0.30; IR (neat): $v_{max}$ 3055, 2209, 1572, 1268, 1158, 920, 752, 537 cm$^{-1}$. HRMS (ESI$^+$): m/z calcd 251.025495 for $C_{12}H_8N_2NaOS^+$ found 251.024955. $^1$H NMR (400 MHz, Chloroform-d): δ 8.36 (s, 0.56H), 8.29 (s, 0.44H), 7.84 (s, 0.56H), 7.60 (ddd, J=7.9, 4.7, 1.7 Hz, 2.44H), 7.43-7.34 (m, 3H). $^{13}$C NMR (100 MHz, $CDCl_3$): δ (ppm) 149.58, 147.98, 140.62, 132.22, 129.94, 126.98, 121.23, 95.02, 81.97.

(E/Z)-2-phenethylthiazole-4-carbaldehyde oxime FR-74

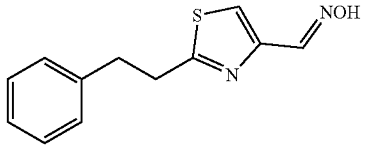

FR-74

To a degassed solution of (E/Z)-2-(phenylethynyl)thiazole-4-carbaldehyde oxime (30 mg, 0.13 mmol, 1 equiv) in dry EtOAc (3 mL), 10% Pd/C (3.5 mg, 0.0177 mmol, 0.25 equiv) was added. After flushing with $H_2$ three times, the reaction mixture was stirred at room temperature under $H_2$ (1 atm.) for 10 h. Upon completion (monitored by TLC), the catalyst was removed by filtration through a short column of celite, the solvent was evaporated, and the residue was purified by column chromatography (EtOAc/PE, 1/9) to afford cis/trans isomers (0.5/0.5 ratio) (E/Z)-2-phenethylthiazole-4-carbaldehyde oxime of as off white solid (28 mg, 88%). $R_f$ (20% EA/PE) 0.25; IR (neat) $v_{max}$:3055, 2851, 2209, 1572. 1158, 1117.44, 1093, 996, 720, 687 $cm^{-1}$. HRMS ($ESI^+$): m/z calcd 255.056799 for $C_{12}H_{12}N_2NaOS^+$ found 255.056255. $^1H$ NMR (400 MHz, Chloroform-d): δ 8.23 (s, 0.5H), 8.04 (dd, J=5.3, 2.8 Hz, 0.5H), 7.74 (s, 0.5H), 7.35 (s, 0.5H), 7.32-7.08 (m, 5H), 3.34 (t, J=7.9 Hz, 2H), 3.12 (t, J=7.9 Hz, 2H). $^{13}C$ NMR (101 MHz, $CDCl_3$): δ 171.49, 169.63, 148.26, 145.37, 144.41, 140.30, 140.18, 139.93, 128.73, 128.68, 128.58, 128.56, 126.65, 126.55, 124.34, 118.52, 35.95, 35.81, 35.23, 34.85.

(E/Z)-2-phenethylthiazole-4-carbaldehyde oxime hydrochloride FR-78

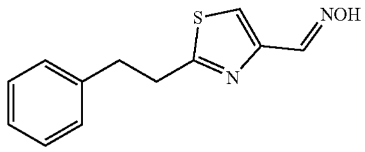

FR-78

To a dry solid of (E/Z)-2-phenethylthiazole-4-carbaldehyde oxime (10 mg), MeOH·HCl (3 mL, 2N) was added. The reaction mixture was stirred at room temperature for 15 min. Upon completion (monitored by TLC), the solvent was evaporated and the dry mixture was washed with diethyl ether (2x3 mL). The solid was dried under vacuum to afford cis/trans isomers (0.5/0.5 ratio) (E/Z)-2-phenethylthiazole-4-carbaldehyde oxime hydrochloride as a white solide (11 mg, 91%). IR (neat) $v_{max}$: 2921, 2851, 2359, 1732, 1330, 1111, 1030, 975, 945, 797, 739, 699, 472. HRMS ($ESI^+$): m/z calcd 255.056799 for $C_{12}H_{12}N_2NaOS^+$ found 255.056255. $^1H$ NMR (400 MHz, Methanol-$d_4$): δ 8.52 (s, 0.5H), 8.17 (s, 0.5H), 7.94 (s, 0.5H), 7.60 (s, 0.5H), 7.46-7.13 (m, 5H), 3.58 (ddt, J=20.2, 14.5, 9.7 Hz, 2H), 3.22-3.08 (m, 2H). $^{13}C$ NMR (101 MHz, Methanol-$d_4$): δ 169.71, 144.50, 139.93, 139.82, 139.12, 128.18, 128.17, 128.14, 126.13, 126.08, 124.65, 35.46, 34.06.

(Z/E)-2-(2-(pyridin-4-yl)ethyl)thiazole-5-carbaldehyde oxime hydrochloride FR-80

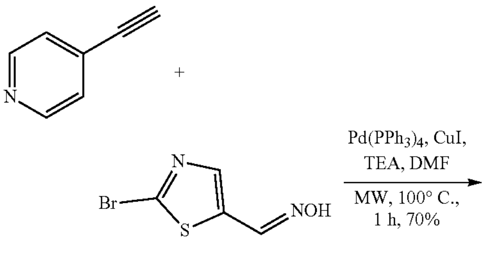

-continued

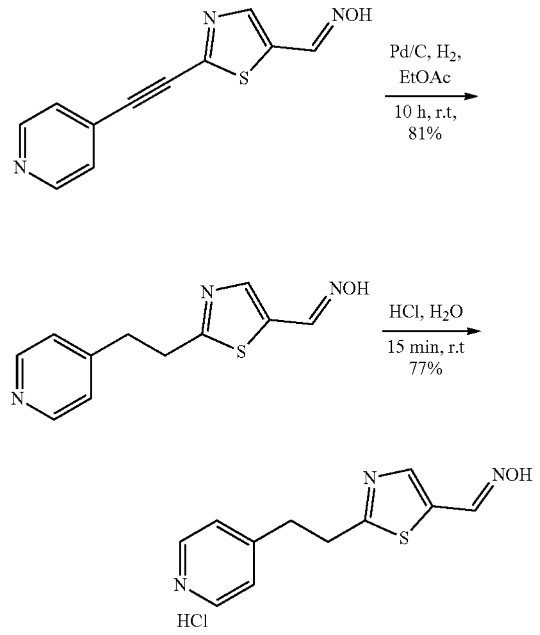

FR-80

(E/Z)-5-(pyridin-4-ylethynyl)thiazole-2-carbaldehyde oxime FR-73

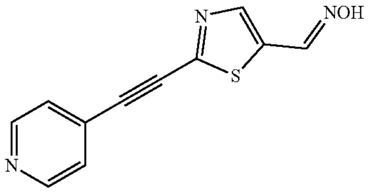

FR-73

To a degassed solution of (E/Z)-2-bromothiazole-5-carbaldehyde oxime (80 mg, 0.386 mmol, 1 equiv) in DMF/$Et_3N$ (8 mL/2 mL), $Pd[PPh_3]_4$ (89.3 mg, 0.077 mmol, 0.2 equiv) and CuI (29.44 mg, 0.154 mmol, 0.4 equiv) were added. After degassing the reaction mixture for 5 min at room temperature, a degassed solution of 4-ethynylpyridine (47.82 mg, 0.463 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/PE 1:1) to afford cis/trans isomers (0.9/0.1 ratio) (E/Z)-5-(pyridin-4-ylethynyl)thiazole-2-carbaldehyde oxime as a brown solid (62 mg, 70%). $R_f$ (55% EA+PE): 0.30; IR (neat): $v_{max}$: 3045, 2716, 2359, 2122, 1731, 1668, 1540, 1466, 1318, 1266, 941, 876, 752, 683. HRMS ($ESI^+$): m/z calcd 230.038806 for $C_{11}H_8N_3OS^+$ found 230.038259. $^1H$ NMR (400 MHz, Acetic acid-$d_4$): δ 8.94 (s, 2H), 8.51 (s, 1H), 8.20 (s, 1H), 7.94 (d, J=4.6 Hz, 2H). $^{13}C$ NMR (101 MHz, Acetic acid-$d_4$): δ 151.89, 148.45, 148.09, 145.57, 142.35, 138.81, 133.61, 128.86, 128.04, 93.59, 87.84.

(Z/E)-2-(2-(pyridin-4-yl)ethyl)thiazole-5-carbaldehyde oxime FR-77

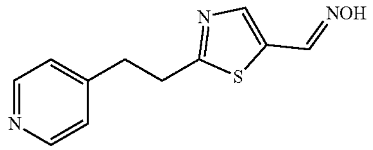

FR-77

To a degassed solution of ((Z/E)-2-(2-(pyridin-4-yl)ethynyl)thiazole-5-carbaldehyde oxime (18 mg, 0.078 mmol, 1 equiv) in dry EtOAc (3 mL), 10% Pd/C (7 mg, 0.0354 mmol, 0.45 equiv) was added. After flushing with $H_2$ three times, the reaction mixture was stirred at room temperature under $H_2$ (1 atm.) for 10 h. Upon completion (monitored by TLC), the catalyst was removed by filtration through a short column of celite, the solvent was evaporated, and the residue was purified by column chromatography (EtOAc) to afford cis/trans isomers (0.8/0.2 ratio) (E/Z)-5-(pyridin-4-ylethynyl)thiazole-2-carbaldehyde oxime as a yellow solid (15 mg, 81%). $R_f$(EA) 0.30. IR (neat): $v_{max}$ 3045, 2716, 1731, 1540, 1495, 1466, 1212, 1176, 1108, 1064, 941, 876, 683. HRMS ($ESI^+$): m/z calcd 234.07008 for $C_{11}H_{12}N_3OS^+$ found 230.069559. $^1H$ NMR (400 MHz, Acetic Acid-$d_4$): δ 8.90 (d, J=6.1 Hz, 2H), 8.41 (s, 0.21H), 8.24 (s, 0.81H), 7.99 (s, 1H), 7.92 (d, J=6.3 Hz, 2H), 3.73-3.57 (m, 2H), 3.52 (d, J=8.3 Hz, 2H). $^{13}C$ NMR (101 MHz, Acetic Acid-$d_4$): δ 175.56, 160.63, 146.98, 143.94, 143.70, 142.69, 139.05, 127.67, 49.77, 36.13, 36.03, 33.10, 32.64, 20.59, 20.39, 20.20, 20.00, 19.80, 19.61, 19.41.

(Z/E)-2-(2-(pyridin-4-yl)ethyl)thiazole-5-carbaldehyde oxime hydrochloride FR-80

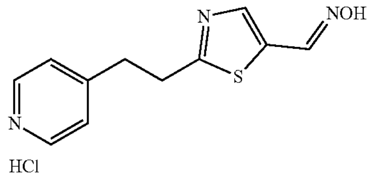

To a dry solid of (Z/E)-2-(2-(pyridin-4-yl)ethyl)thiazole-5-carbaldehyde oxime (10 mg), $H_2O·HCl$ (2 mL, 2N). was added The reaction mixture was stirred at room temperature for 15 min. Upon completion (monitored by TLC), the solvent was evaporated and the dry mixture was washed with diethyl ether (2×3 mL). The solid was dried under vacuum to afford cis/trans isomers (0.9/0.1 ratio) (Z/E)-2-(2-(pyridin-4-yl)ethyl)thiazole-5-carbaldehyde oxime hydrochloride (9 mg, 77%). IR (neat): $v_{max}$ 3044, 3005, 2716, 2340, 1715, 1598, 1495, 1317, 1266, 1176, 813, 752, 625, 588. HRMS: ($ESI^+$): m/z calcd 234.07008 for $C_{11}H_{12}N_3OS^+$ found 230.069559. $^1H$ NMR (400 MHz, Methanol-$d_4$): δ 8.81-8.71 (m, 2H), 8.26 (d, J=6.8 Hz, 1H), 8.07-7.97 (m, 2H), 7.88 (d, J=12.1 Hz, 1H), 3.71-3.45 (m, 4H). $^{13}C$ NMR: (101 MHz, Methanol-$d_4$): δ 161.85, 141.06, 140.49, 136.49, 127.40, 48.24, 48.03, 47.82, 47.60, 47.39, 47.18, 46.96, 34.49, 31.15, 30.27.

(Z/E)-2-heptylthiazole-4-carbaldehyde oxime hydrochloride FR-79

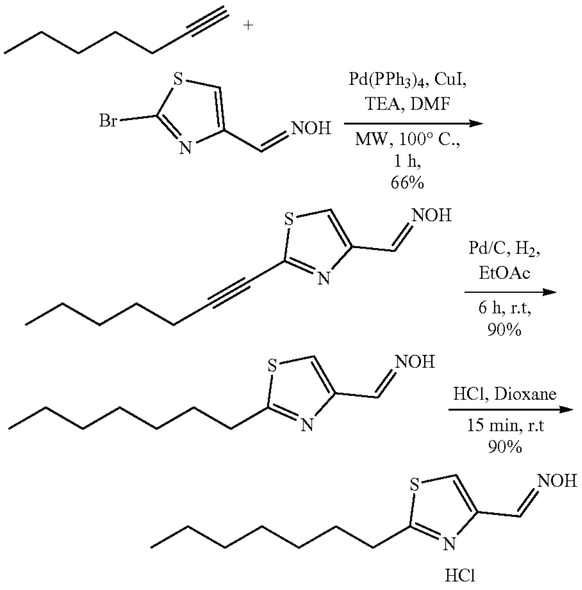

FR-79

(E/Z)-4-(hept-1-yn-1-yl)thiazole-2-carbaldehyde oxime FR-75

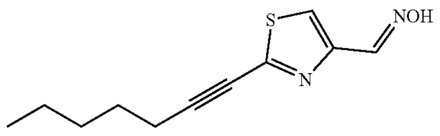

To a degassed solution of (E/Z)-2-bromothiazole-4-carbaldehyde oxime (80 mg, 0.386 mmol, 1 equiv) in DMF/$Et_3N$ (8 mL/2 mL), $Pd[PPh_3]_4$ (89.3 mg, 0.077 mmol, 0.2 equiv) and CuI (29.44 mg, 0.154 mmol, 0.4 equiv) were added. After degassing the reaction mixture for 5 min at room temperature, the hept-1-yne (44.59 mg, 0.463 mmol, 1.2 equiv) was added dropwise and the reaction mixture was subjected to microwave irradiation for 1 hour at 90° C. After completion (monitored by TLC), the reaction mixture was concentrated under reduced pressure and the residue was purified by column chromatography (EtOAc/PE, 1:5) to afford cis/trans isomers (1/1 ratio) (E/Z)-4-(hept-1-yn-1-yl) thiazole-2-carbaldehyde oxime as a white solid (66 mg, 76%). $R_f$(20% EA/PE): 0.30; IR (neat): $v_{max}$, 3151, 2927, 2857, 2230, 1667, 1588, 1508, 1458, 1436, 1375, 1322, 1290, 1250, 1203, 1119, 993, 916, 773, 721, 693. HRMS ($ESI^+$): m/z calcd 245.073045 for $C_{11}H_{14}N_2NaOS^+$ found 245.071905. $^1H$ NMR (400 MHz, Chloroform-d): δ 8.24 (s, 1H), 7.76 (s, 0.5H), 7.61 (s, 0.5H) 2.52-2.41 (m, 2H), 1.70-1.57 (m, 2H), 1.47-1.31 (m, 4H), 0.91 (td, J=7.2, 2.9 Hz, 3H). $^{13}C$ NMR (100 MHz, $CDCl_3$): δ (ppm) 150.11, 148.57, 144.45, 125.85, 98.00, 73.37, 31.09, 27.64, 22.16, 19.53, 13.91.

(Z/E)-2-heptylthiazole-4-carbaldehyde oxime FR-76

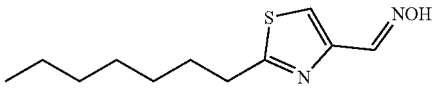

To a degassed solution of (E/Z)-4-(hept-1-yn-1-yl)thiazole-2-carbaldehyde oxime (25 mg, 0.112 mmol, 1 equiv) in dry EtOAc (3 mL), 10% Pd/C (7 mg, 0.0354 mmol, 0.3 equiv) was added. After flushing with $H_2$ three times, the reaction mixture was stirred at room temperature under $H_2$ (1 atm.) for 6 h. Upon completion (monitored by TLC), the catalyst was removed by filtration through a short column of celite, the solvent was evaporated to afford cis/trans isomers (0.5/0.5 ratio) of (Z/E)-2-heptylthiazole-4-carbaldehyde oxime as a white solid (23 mg, 90%). $R_f$(20% EA+PE): 0.30 IR (neat): $v_{max}$ 3151, 2927, 1667, 1588, 1508, 1458, 1436, 1290, 1119, 993, 916, 773, 721. HRMS ($ESI^+$): m/z calcd 249.10388 for $C_{11}H_{14}N_2NaOS^+$ found 249.103205. $^1$H NMR (400 MHz, $CDCl_3$): δ 8.20 (s, 0.45H), 7.97 (s, 0.55H), 7.71 (s, 0.55H), 7.37 (s, 0.45H), 3.02 (td, J=7.7, 1.6 Hz, 2H), 1.86-1.74 (m, 2H), 1.43-1.26 (m, 8H), 0.87 (dt, J=7.0, 3.4 Hz, 3H). $^{13}$C NMR (101 MHz, $CDCl_3$): δ 172.95, 171.24, 148.02, 145.38, 144.46, 140.04, 123.58, 118.26, 77.35, 77.03, 76.71, 33.52, 33.14, 31.65, 30.02, 29.85, 29.06, 28.98, 28.93, 28.90, 22.60, 14.06.

(Z/E)-2-heptylthiazole-4-carbaldehyde oxime hydrochloride FR-79

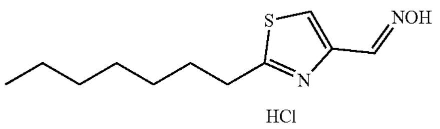

To a dry solid of (Z/E)-2-heptylthiazole-4-carbaldehyde oxime (10 mg), Dioxane·HCl was added (1 mL, 4N). The reaction mixture was stirred at room temperature for 5 min. Upon completion (monitored by TLC), the solvent was evaporated and the dry mixture was washed with diethyl ether (2×3 mL). The solid was dried under vacuum to afford cis/trans isomers (0.5/0.5 ratio) of (Z/E)-2-heptylthiazole-4-carbaldehyde oxime hydrochloride (10.5 mg, 90%). IR (neat): $v_{max}$ 2923, 2853, 2359, 1455, 1132, 969, 922, 756, 723, 669, 541. HRMS ($ESI^+$): m/z calcd 249.10388 for $C_{11}H_{14}N_2NaOS^+$ found 249.103205. $^1$H NMR (400 MHz, Methanol-$d_4$): δ 8.46 (s, 0.5H), 8.14 (s, 0.5H), 7.87 (s, 0.5H), 7.57 (s, 0.5H), 3.10 (dd, J=18.0, 10.5 Hz, 2H), 1.92-1.67 (m, 2H), 1.39-1.23 (m, 8H), 0.95-0.84 (m, 3H). $^{13}$C NMR (101 MHz, Methanol-$d_4$): δ 172.99, 172.95, 140.21, 137.24, 125.06, 125.02, 31.62, 31.41, 31.39, 29.61, 28.66, 28.62, 28.58, 28.55, 22.83, 22.25, 13.01.

(Z/E)-2-(3-cyclohexylprop-1-yn-1-yl)thiazole-4-carbaldehyde oxime FR-84

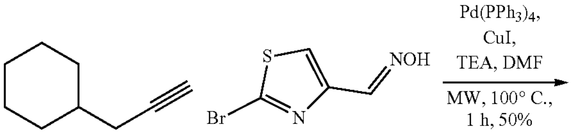

-continued

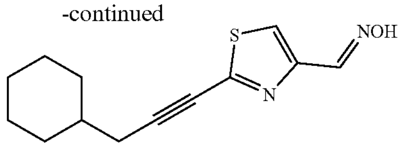

To a degassed solution of (E/Z)-2-bromothiazole-4-carbaldehyde oxime (50 mg, 0.241 mmol, 1 equiv) in DMF/$Et_3N$ (8 mL/2 mL), $Pd[PPh_3]_4$ (55.81 mg, 0.048 mmol, 0.2 equiv) and CuI (18.4 mg, 0.096 mmol, 0.4 equiv) were added. After degassing the reaction mixture for 5 min at room temperature, the prop-2-yn-1-ylcyclohexane (35.42 mg, 0.289 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/PE 1:5) to afford cis/trans isomers (0.5/0.5 ratio) of (Z/E)-2-(3-cyclohexylprop-1-yn-1-yl)thiazole-4-carbaldehyde oxime as a white solid (30 mg, 50%). $R_f$ (20% EA+PE) 0.30; IR (neat): $v_{max}$ 2846.76, 2228.43, 1446.96, 1321.44, 1277.02, 975.14, 676.93, 705.34. HRMS ($ESI^+$): m/z calcd 249.10617 for $C_{13}H_{17}N_2OS^+$ found 249.106475. $^1$H NMR (400 MHz, Chloroform-d): δ 8.22 (s, 1H), 7.80 (s, 0.5H), 7.51 (s, 0.5H), 2.36 (t, J=6.5 Hz, 2H), 1.86 (d, J=12.1 Hz, 2H), 1.67 (dddt, J=35.2, 14.7, 7.7, 3.5 Hz, 4H), 1.31-1.00 (m, 5H). $^{13}$C NMR (101 MHz, $CDCl_3$): δ 148.61, 126.01, 97.23, 96.87, 74.24, 37.05, 32.85, 32.83, 27.36, 26.14, 26.09.

Methyl 6-(4-((hydroxyimino)methyl)thiazol-2-yl)hex-5-ynoate FR-85

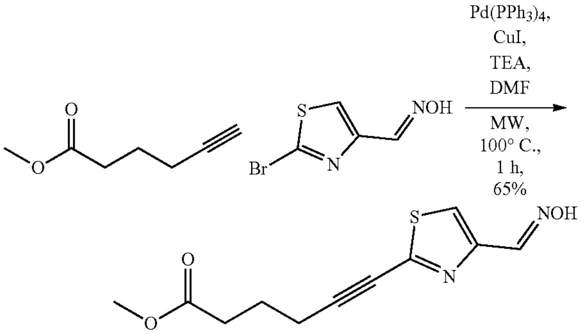

To a degassed solution of (E/Z)-2-bromothiazole-4-carbaldehyde oxime (50 mg, 0.241 mmol, 1 equiv) in DMF/$Et_3N$ (8 mL/2 mL), $Pd[PPh_3]_4$ (55.81 mg, 0.048 mmol, 0.2 equiv) and CuI (18.4 mg, 0.096 mmol, 0.4 equiv) were added. After degassing the reaction mixture for 5 min at room temperature, the methyl hex-5-ynoate (37.69 mg, 0.289 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/P 1:4) to afford cis/trans isomers (0.5/0.5 ratio) of methyl 6-(4-((hydroxyimino)methyl)thiazol-2-yl)hex-5-ynoate as a white solid (40 mg, 65%). $R_f$ (30% EA+P) 0.30; IR (neat): $v_{max}$ 3179, 3099, 3003, 2925, 2360, 2234, 1726, 1632, 1508, 1436, 1375, 1319, 1248, 1197, 977, 766, 666, 421. $^1$H NMR (400 MHz, Chloroform-d) δ 8.32 (s, 1H), 7.77 (s, 0.5H), 7.53 (s, 0.5H), 3.68 (d, J=2.3 Hz, 3H), 2.55 (q, J=6.9 Hz, 2H), 2.50 (td, J=7.3, 3.0 Hz, 2H), 1.95 (h, J=7.1 Hz, 2H). $^{13}C$ NMR (101 MHz, $CDCl_3$) δ 173.46, 173.43, 149.71, 148.77, 148.01, 144.28, 126.33, 96.16, 96.00, 74.51, 74.19, 51.79, 51.78, 32.78, 32.76, 29.73, 23.15, 22.98, 19.00. HRMS ($ESI^+$): m/z calcd 275.046629 for $C_{11}H_{12}N_2NaOS^+$ found 275.045988.

(E/Z)-2-(pyren-2-ylethynyl)thiazole-4-carbaldehyde oxime FR-109

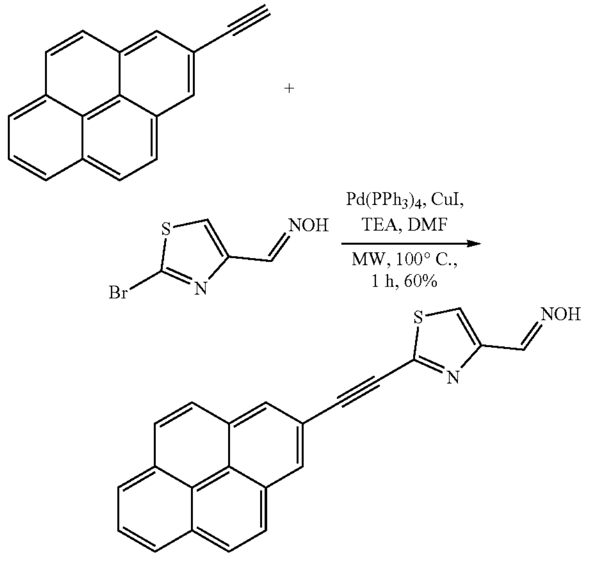

To a degassed solution of (E/Z)-2-bromothiazole-4-carbaldehyde oxime (50 mg, 0.241 mmol, 1 equiv) in DMF/$Et_3N$ (8 mL/2 mL), $Pd[PPh_3]_4$ (55.81 mg, 0.048 mmol, 0.2 equiv) and CuI (18.4 mg, 0.096 mmol, 0.4 equiv) were added. After degassing the reaction mixture for 2 min at room temperature, the alkyne (2-ethynylpyrene, 65.57 mg, 0.289 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by preparative chromatography (EtOAc/Pentane, 1:4) to afford cis/trans isomers (0.6/0.4 ratio) of (E/Z)-2-(pyren-2-ylethynyl)thiazole-4-carbaldehyde oxime as a yellow solid (51 mg, 60%). $R_f$ (25% EA+Pentane) 0.30; IR (neat): $v_{max}$ 3734, 2921, 2360, 2340, 1507, 1456, 1188, 1050, 1033.06, 995, 923, 835, 819, 751, 710, 677, 668. HRMS ($ESI^+$) m/z calcd 353.07483 for $C_{22}H_{13}N_2OS^+$ found 353.074310. $^1H$ NMR (400 MHz, DMSO-$d_6$): δ 12.24 (s, 0.4H), 11.52 (s, 0.6H), 8.70 (s, 0.4H), 8.51 (d, J=9.1 Hz, 1H), 8.44-8.36 (m, 3H), 8.34 (s, 2H), 8.30 (d, J=8.9 Hz, 1H), 8.27-8.20 (m, 1.6H), 8.14 (t, J=7.7 Hz, 1H), 8.10 (s, 1H), 7.77 (s, 0.4H). $^{13}C$ NMR (101 MHz, DMSO-$d_6$): δ 150.54, 146.73, 146.40, 143.25, 139.62, 132.48, 132.08, 131.17, 130.84, 130.53, 130.09, 129.71, 128.32, 127.70, 127.49, 127.02, 126.97, 125.54, 124.72, 123.97, 123.68, 121.57, 114.69.

2-(3-hydroxyprop-1-yn-1-yl)thiazole-4-carbaldehyde oxime FR-101

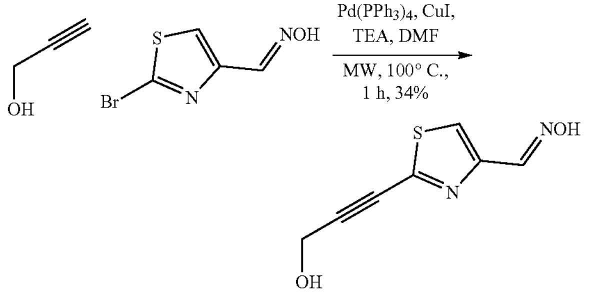

To a degassed solution of (E/Z)-2-bromothiazole-4-carbaldehyde oxime (80 mg, 0.386 mmol, 1 equiv) in DMF/$Et_3N$ (8 mL/2 mL), $Pd[PPh_3]_4$ (89.3 mg, 0.077 mmol, 0.2 equiv) and CuI (29.44 mg, 0.154 mmol, 0.4 equiv) were added. After degassing the reaction mixture for 2 min at room temperature, the alkyne (prop-2-yn-1-ol, 0.027 mL, 0.463 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/Pentane 1:5) to afford the desired coupled oxime as a white solid (24 mg, 34%). $R_f$ (25% EA+Pentane) 0.30. IR (neat): $v_{max}$ 3095, 2359, 1429, 1209, 1036, 984, 753. HRMS ($ESI^+$) m/z calcd 183.0228 for $C_7H_6N_2O_2S^+$ found 183.022275. $^1H$ NMR (400 MHz, Acetone-$d_6$): δ 11.33 (s, 0.25H), 10.60 (s, 0.75H), 8.59 (s, 0.25H), 8.21 (s, 0.75H), 7.86 (s, 0.75H), 7.65 (s, 0.25H), 4.60 (s, 1H), 4.49 (d, J=5.1 Hz, 2H). $^{13}C$ NMR (101 MHz, Acetone-$d_6$): δ 150.87, 148.75, 147.31, 146.81, 143.87, 140.30, 127.19, 119.39, 94.98, 94.92, 77.45, 77.27, 50.65, 50.54.

2-((hydroxyimino)methyl)-4-phenethylthiazol-3-ium chloride CV-05

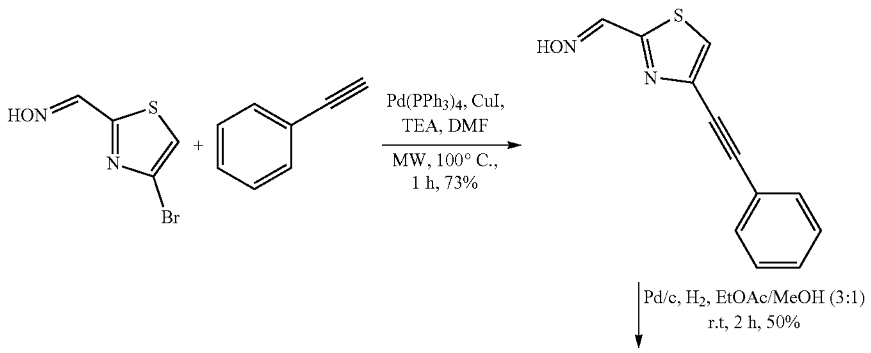

-continued

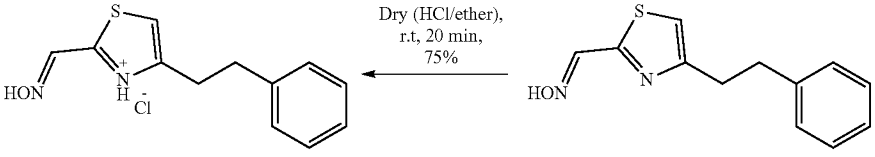

CV-05

4-(phenylethynyl)thiazole-2-carbaldehyde oxime CV-01

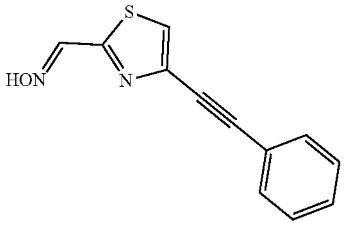

To a degassed solution of oxime (100 mg, 0.483 mmol, 1 equiv) in DMF/$Et_3N$ (8 mL/2 mL), $Pd[PPh_3]_4$ (112 mg, 0.097 mmol, 0.2 equiv) and CuI (37 mg, 0.193 mmol, 0.4 equiv) were added. After degassing the reaction mixture for 5 min at room temperature, the alkyne (phenylacetylene, 59.2 mg, 0.580 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/P 1:4) to afford the desired coupled oxime as an orange-yellow solid (80 mg, 73%). $R_f$ (20% EA+P) {0.36; 0.51}; IR (neat) $v_{max}$ 3103.55, 2920.87, 2849.95, 1499.95 $cm^{-1}$. HRMS ($ESI^+$) m/z calcd 229.04353 for $C_{12}H_9N_2OS^+$ found 229.043010. $^1H$ NMR (400 MHz, Acetone-$d_6$) δ 12.24 (s, 0.5H), 11.37 (s, 0.5H), 8.33 (d, J=0.9 Hz, 0.5H), 8.09 (d, J=1.0 Hz, 0.5H), 7.97 (d, J=1.1 Hz, 0.5H), 7.84 (d, J=0.9 Hz, 0.5H), 7.58 (tdd, J=5.3, 3.0, 1.6 Hz, 2H), 7.43 (ddt, J=5.5, 4.0, 2.0 Hz, 3H). $^{13}C$ NMR (101 MHz, Acetone) δ 162.70, 154.68, 144.55, 140.97, 138.43, 137.85, 132.58, 132.48, 132.18, 132.16, 129.64, 129.29, 127.96, 124.69, 122.87, 122.83, 122.75, 89.43, 89.26, 83.98, 83.84.

4-phenethylthiazole-2-carbaldehyde oxime CV-03

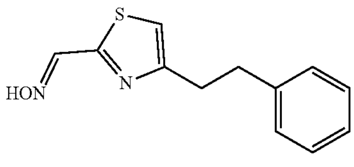

To a degassed solution of CV01 (30 mg, 0.131 mmol, 1 equiv) in EtOAc/MeOH (3 mL/1 mL), Pd/C (14 mg (10% w), 0.013 mmol, 0.1 equiv) was added. After degassing for 5 min, the reaction mixture was stirred under $H_2$ pressure for 1 h. After completion (monitored by TLC), the reaction mixture was concentrated under reduced pressure and the residue was purified by preparative chromatography (EtOAc/P 1:5; 3 times) to afford the desired hydrogenated compound as a white solid (15 mg, 50%). $R_f$ (20% EA+P) {0.62; 0.85}; IR (neat) $v_{max}$ 2920.68, 2851.88, 2360.37, 1452.98 $cm^{-1}$. HRMS ($ESI^+$) m/z calcd 232,06703 for $C_{12}H_{13}N_2OS^+$ found 233.074310 $^1H$ NMR (400 MHz, $CDCl_3$) δ 8.35 (s, OH), 7.99 (s, OH), 7.24-7.15 (m, 2H), 7.12 (td, J=7.0, 1.8 Hz, 3H), 6.73 (s, OH), 3.13-2.91 (m, 4H)$^{13}C$ NMR (101 MHz, $CDCl_3$) δ 161.86, 157.73, 156.99, 145.68, 141.54, 141.48, 128.90, 128.87, 128.85, 126.56, 126.53, 119.13, 115.31, 46.56, 35.97, 35.87, 33.60, 33.45.

2-((hydroxyimino)methyl)-4-phenethylthiazol-3-ium chloride CV-05

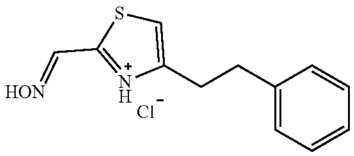

To a solution of CV03 (14 mg, 0.060 mmol, 1 equiv) in minimal volume of dichloromethane dry HCl/ether (2 mL) was added dropwise. The mixture was stirred at room temperature. After completion (monitored by TLC), the formed salt (12 mg, 75%) was concentrated under reduced pressure and washed with pentane IR (neat) $v_{max}$ 2918.47, 2752.43, 2360.18, 2340.23, 1513.34, 1452.39 $cm^{-1}$. HRMS ($ESI^+$) m/z calcd 232,06703 for $C_{12}H_{13}N_2OS^+$ found 233.074310 $^1H$ NMR (400 MHz, MeOD) δ 8.36 (s, OH), 8.15-8.07 (m, 1H), 7.73 (d, J=3.4 Hz, 1H), 7.50 (s, OH), 7.21-7.14 (m, 3H), 7.14-7.05 (m, 4H), 3.12 (dt, J=25.4, 7.7 Hz, 4H). $^{13}C$ NMR (101 MHz, MeOD) δ 150.37, 134.67, 129.43, 129.39, 129.19, 127.40, 127.34, 123.01, 49.21, 49.00, 48.79, 48.57, 35.21, 30.54.

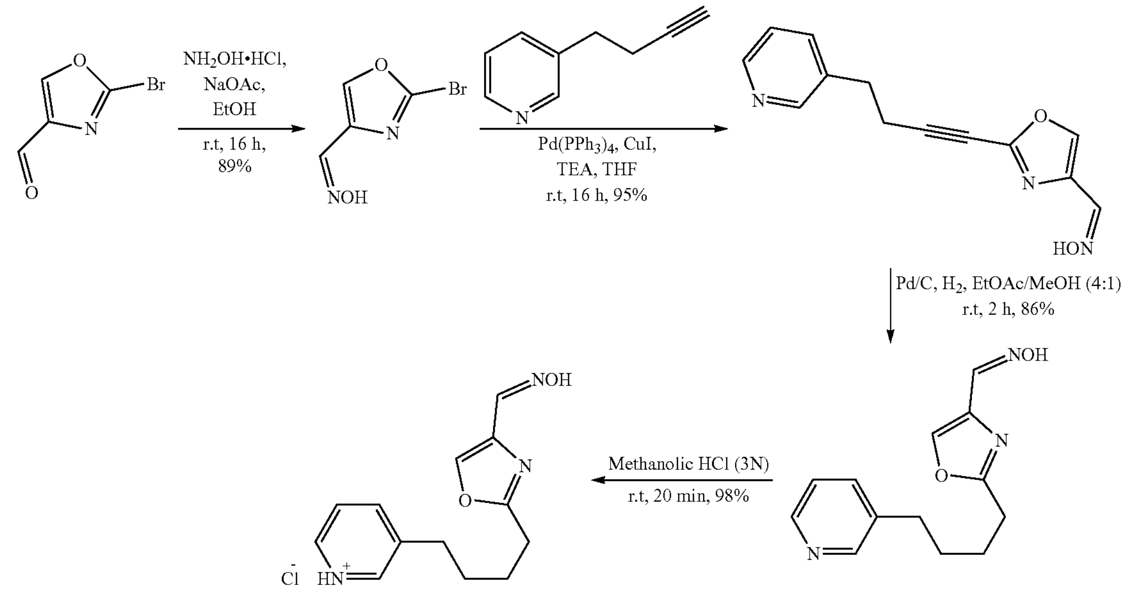

Bromooxazole-4-carbaldehyde oxime CV-19

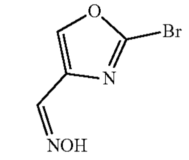

To a degassed solution of aldehyde (100 mg, 0.568 mmol, 1 equiv) in EtOH (8 mL), NaOAc (140 mg, 1.70 mmol, 3 equiv) and hydroxylamine hydrochloride (60 mg, 0.852 mmol, 1.5 equiv) were added. The mixture was stirred at rt for 16 h. After completion monitored by TLC, the reaction mixture was concentrated under reduced pressure and purified by column chromatography (EtOAc/PE 3:7) to obtain the cis/trans isomer (15/85, ratio) (97 mg, 89%). $R_f$ (30% EtOAc/PE) 0.37; 0.46. IR (neat) $v_{max}$ 3171.99, 3133.58, 3092.36, 2922.25, 2848.70, 1672.12, 1519.88 $cm^{-1}$ $^1H$ NMR (400 MHz, Acetone) δ 8.69 (s, 1H), 8.29 (s, 0.15H), 7.99 (s, 0.15H), 7.41 (s, 1H). $^{13}C$ NMR (101 MHz, Acetone) δ 206.35, 147.50, 138.62, 134.49, 134.46.

2-(4-(pyridin-3-yl)but-1-yn-1-yl)oxazole-4-carbaldehyde oxime CV-22

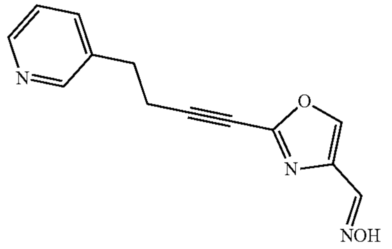

To a degassed solution of oxime (43 mg, 0.225 mmol, 1 equiv) in THF/$Et_3N$ (8 mL/2 mL), Pd[$PPh_3$]$_4$ (52 mg, 0.045 mmol, 0.2 equiv) and CuI (17 mg, 0.090 mmol, 0.4 equiv) were added. After degassing the reaction mixture for 5 min at room temperature, the alkyne (3-(but-3-yn-1-yl)pyridine, 35 mg, 0.270 mmol, 1.2 equiv) was added dropwise and the reaction mixture was stirred at the room temperature for 16 h. After completion (monitored by TLC), the reaction mixture was concentrated under reduced pressure and the residue was purified by chromatography column (EtOAc/PE 7:3) followed by preparative TLC (MeOH/DCM 1:9) to afford the desired coupled oxime as a white solid (51 mg, 59%). $R_f$(100% EtOAc) 0.52; IR (neat) $v_{max}$ 3141.78, 3008.49, 2921.77, 2852.27, 2244.65, 1743.79, 1543.98 $cm^{-1}$ $^1H$ NMR (400 MHz, MeOD) δ 8.54 (s, 1H), 8.52 (d, J=2.3 Hz, 1H), 8.46-8.41 (m, 1H), 7.87-7.82 (m, 1H), 7.42 (ddd, J=7.9, 4.9, 0.9 Hz, 1H), 7.36 (s, 1H), 3.02 (t, J=7.0 Hz, 2H), 2.88 (td, J=7.0, 0.9 Hz, 2H). $^{13}C$ NMR (101 MHz, MeOD) δ 150.28, 148.30, 147.12, 144.78, 138.85, 138.53, 132.75, 125.23, 94.53, 70.22, 31.82, 21.40.

4-(pyridin-3-yl)butyl)oxazole-4-carbaldehyde oxime CV-23

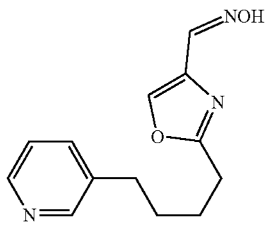

To a solution of 2-(4-(pyridin-3-yl)but-1-yn-1-yl)oxazole-4-carbaldehyde oxime (25 mg, 0.104 mmol in EtOAc (3 mL) was added 10% Pd/C (10 mg) After degassing for 5 min, the reaction mixture was stirred under $H_2$ pressure for 1 h. Upon completion, the mixture was filtered through a small celite pad, concentrated under reduced pressure followed by column chromatography (EtOAc/PE, 8:2) to afford 4-(pyridin-3-yl)butyl)oxazole-4-carbaldehyde oxime as a white solid (18 mg, 72%). $R_f$ (100% EtOAc) 0.49. IR (neat) $\nu_{max}$ 3099.54, 3023.32, 2922.20, 2851.19, 2698.84, 2359.07, 1577.19 $cm^{-1}$ $^1H$ NMR (400 MHz, MeOD) δ 8.48 (s, 1H), 8.38 (s, 2H), 7.99 (s, OH), 7.71 (dt, J=8.0, 1.8 Hz, 1H), 7.36 (s, 2H), 2.86 (t, J=7.3 Hz, 2H), 2.72 (dd, J=9.0, 6.0 Hz, 2H), 1.89-1.78 (m, 2H), 1.78-1.67 (m, 2H). $^{13}C$ NMR (101 MHz, MeOD) δ 165.86, 150.03, 147.58, 144.09, 139.45, 138.25, 131.90, 33.25, 31.47, 28.21, 27.27. HRMS ($ESI^+$) m/z calcd 246.12370 for $C_{13}H_{16}N_3O_2^+$ found 246.124385.

3-(4-(4-((hydroxyimino)methyl)oxazol-2-yl)butyl) pyridin-1-ium chloride CV-24

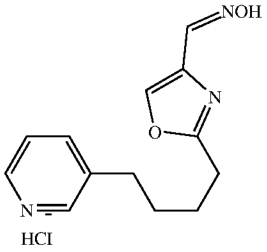

To a solution of 4-(pyridin-3-yl)butyl)oxazole-4-carbaldehyde oxime (17.8 mg, 0.073 mmol) was added methanolic HCl (3N, 3 mL) at room temperature and stirred for 20 min at same temperature. Upon completion, solvent was distilled off under reduced pressure and the resulted solid was washed with diethyl ether (2×4 mL). The solid was dried under vacuum to give the desired compound as a yellow solid (20.2 mg, 98%) IR (neat) $\nu_{max}$ 2921.57, 2852.21, 2364.21, 1745.30, 1639.93, 463.23 $cm^{-1}$ $^1H$ NMR (400 MHz, MeOD) δ 8.82 (d, J=2.0 Hz, 1H), 8.74 (d, J=5.2 Hz, 1H), 8.59 (d, J=12.7 Hz, 2H), 8.33 (s, 0.2H), 8.06 (dd, J=8.1, 5.8 Hz, 1H), 7.42 (s, 0.6H), 2.97 (q, J=7.0 Hz, 4H), 1.98-1.78 (m, 4H). $^{13}C$ NMR (101 MHz, MeOD) δ 166.46, 148.33, 148.29, 144.59, 144.32, 144.20, 142.16, 140.40, 137.84, 130.32, 128.43, 32.89, 30.65, 27.95, 26.75. HRMS ($ESI^+$) m/z calcd 246.12370 for $C_{13}H_{16}N_3O_2^+$ found 246.124385.

Example 2: In Vitro Reactivation of Human Acetyicholinesterase (hAChE) by Compounds of the Invention Compounds NM-55, NM-109, NM-130, NM-131, NM-132, NM-139, NM-141, NM-143, NM-152, NM-168, NM-171 and NM-176 of the invention were tested for their reactivation properties of hAChE inhibited by O-ethyl S-[2-(diisopropylamino)ethyl]methylphosphonothioate (VX), tabun, sarin or paraoxon. 2-PAM (pralidoxime or 2-[(E)-(hydroxyimino)methyl]-1-methylpyridinium) and HI6 (asoxime chloride or [1-[(4-carbamoylpyridin-1-ium-1-yl) methoxymethyl]pyridin-2-ylidene]methyl-oxoazanium dichloride) were used as comparative compounds.

Inhibition of hAChE by OPNAs. Recombinant hAChE was produced and purified as previously described (see reference https://www.ncbi.nlm.nih.gov/pubmed/31132435). VX, sarin and tabun have been supplied by DGA maîtrise NRBC (Vert le Petit, France). Stock solutions of OPNA at 5 mM in isopropanol were used to inhibit the purified hAChE as previously described [Carletti, E. et al.

2008]. Briefly, a ten-fold excess of OPNA was used to perform the inhibition of hAChE in a sodium phosphate buffer (100 mM, pH 7.4, 0.1% BSA) at 25° C. Complete inhibition of hAChE was monitored by measuring the residual activity with a modified Ellman assay as previously described [Ellman, G. L., et al. 1961] and excess of OPNA were removed by using a desalting PD-10 column (GE Healthcare).

$IC_{50}$ measurements. Compounds were dissolved in water to make 40 mM stock solutions. Recombinant hAChE activity was measured spectrophotometrically at 25° C., monitoring the absorbance at 412 nm, in 1 mL of Ellman's buffer (0.5 mM DTNB, 0.1% BSA, 0.1 M phosphate, pH 7.4), in the presence of appropriate oxime concentrations. Measurements were performed at least in duplicate for each concentration tested. The oxime concentration producing 50% inhibition was determined by nonlinear fitting with ProFit (Quantumsoft) using the standard IC 50 equation: % activity=100×IC50/(IC50+[Ox]).

Reactivation of hAChE inhibited by OPNAs. The ability of the compounds to reactivate OP-inhibited hAChE were assessed with a modified Ellman assay using a microplate reader (SPARK 10M, Tecan) and a continuous method described previously [Kitz, R. J., et al. 1965, Worek, F., et al., 2004] with minor modifications. Briefly, the desired oximes concentrations to be tested were dispensed in a 96-well flat-bottomed polystyrene microplate containing 0.1% BSA phosphate buffer and DTNB. At t=0, OP-inhibited hAChE and acetylthiocholine (ATCh) diluted in 0.1% BSA phosphate buffer were injected in each well containing oximes using the built-in injectors of the microplate reader to a final volume of 200 μL. ATCh hydrolysis was continuously monitored over 30 minutes and the increase of absorbance at 412 nm recorded every 10 seconds at 25° C. Activities were individually corrected for oxime-induced hydrolysis of ATCh.

Reactivation of OP-inhibited hAChE by oximes proceeds according to scheme 1 and kinetics of oximes reactivation were determined as previously described [Worek, F., et al., 2004]. For each oxime concentration, the apparent reactivation rate, $k_{obs}$, the dissociation constant, $K_D$ and the reactivation rate constant, $k_r$, were calculated by nonlinear fitting with ProFit (Quantumsoft) using the standard oxime-concentration-dependent reactivation equation (1):

Scheme 1

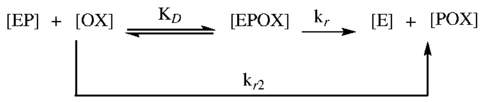

$$k_{obs} = \frac{k_r[OX]}{K_D + [OX]} \quad \text{Eq (1)}$$

When $[OX] \ll K_D$, Eq (1) simplifies to Eq (2):

$$k_{obs} = \left(\frac{k_r}{K_D}\right)[OX] \quad \text{Eq (2)}$$

The second order reactivation rate constant $k_{r2}$, describing the specific reactivity can be derived from Eq (2).

$$k_{r2} = \frac{k_r}{K_D} \quad \text{Eq (3)}$$

For the continuous method of recording OP-inhibited hAChE reactivation by oximes, the velocity of substrate hydrolysis (v) is proportional to the concentration of the reactivated hAChE and is expressed and derived as equation 4 and 5 respectively. $v_t$ is the velocity at time t and $v_0$ represents the maximum velocity. Equation 5 was used to determine the $k_{obs}$ by non-linear regression analysis for each individual oxime concentration with ProFit (Quantumsoft).

$$v_t = v_0(1 - e^{-k_{obs}t}) \quad \text{Eq (4)}$$

$$-d[S] = \int_0^t vdt = v_0 t + \frac{v_0}{k_{obs}}(e^{-k_{obs}t} - 1) \quad \text{Eq (5)}$$

The results are as follows:

TABLE 1

Reactivation of OP-inhibited human hAChE by oximes 2-PAM, HI-6 and NMs

| OP | Oximes | $k_r$ ($min^{-1}$) | $K_D$ (μM) | $k_{r2}$ ($mM^{-1} \cdot min^{-1}$) |
|---|---|---|---|---|
| VX | 2-PAM | 0.2 ± 0.01 | 26 ± 7 | 7 |
| | HI-6 | 0.4 ± 0.02 | 19 ± 4 | 20 |
| | NM-55 | 0.06 ± 0.002 | 6 ± 1 | 10 |
| | NM-109 | 0 | 0 | 0 |
| | NM-130 | 0 | 0 | 0 |
| | NM-131 | 0.1 ± 0.004 | 7 ± 1 | 14 |
| | NM-132 | 0.07 ± 0.002 | 2 ± 0.3 | 35 |
| | CV05 | 0.61 ± 0.01 | 2.3 ± 0.3 | 260 |
| | NM-250 | 0.38 ± 0.03 | 48 ± 14 | 8 |
| | NM-261 | 0.54 ± 0.01 | 12.8 ± 2.5 | 42 |
| Sarin | 2-PAM | 0.3 ± 0.02 | 25 ± 7 | 11 |
| | HI-6 | 0.8 ± 0.06 | 57 ± 11 | 13 |
| | NM-55 | 0.08 ± 0.003 | 3 ± 1 | 27 |
| | NM-109 | 0 | 0 | 0 |
| | NM-130 | 0 | 0 | 0 |
| | NM-131 | 0.08 ± 0.003 | 5 ± 1 | 16 |
| | NM-132 | 0.3 ± 0.002 | 3 ± 1 | 88 |
| Tabun | 2-PAM | 0.5 ± 0.2 | 211 ± 113 | 2 |
| | HI-6 | 0 | 0 | 0 |
| | NM-55 | 0 | 0 | 0 |
| | NM-109 | 0 | 0 | 0 |
| | NM-130 | 0 | 0 | 0 |
| | NM-131 | 0 | 0 | 0 |
| | NM-132 | 0 | 0 | 0 |
| Paraoxon | 2-PAM | 0.07 ± 0.02 | 68 ± 16 | 1 |
| | HI-6 | 0.8 ± 0.06 | 290 ± 70 | 0.4 |
| | NM-55 | 0.11 ± 0.004 | 0.12 ± 0.03 | 917 |
| | NM-109 | 0 | 0 | 0 |
| | NM-130 | 0 | 0 | 0 |
| | NM-131 | 0.2 ± 0.006 | 12 ± 2 | 17 |
| | NM-132 | 0.3 ± 0.02 | 56 ± 11 | 5 |

TABLE 2

Reactivation of OP-inhibited human hAChE by oximes 2-PAM, HI-6 and NMs

| OP | Oximes | $k_r$ ($min^{-1}$) | $K_D$ (μM) | $k_{r2}$ ($mM^{-1} \cdot min^{-1}$) |
|---|---|---|---|---|
| VX | 2-PAM | 0.2 ± 0.01 | 26 ± 7 | 7 |
| | HI-6 | 0.4 ± 0.02 | 19 ± 4 | 20 |
| | NM-139 | 0.2 ± 0.008 | 19 ± 4 | 8 |
| | NM-141 | 0.09 ± 0.004 | 1 ± 0.2 | 90 |
| | NM-143 | 0.07 ± 0.0007 | 0.1 ± 0.02 | 700 |
| | NM-152 | 0 | 0 | 0 |

TABLE 2-continued

Reactivation of OP-inhibited human hAChE by oximes 2-PAM, HI-6 and NMs

| OP | Oximes | $k_r$ ($min^{-1}$) | $K_D$ (μM) | $k_{r2}$ ($mM^{-1} \cdot min^{-1}$) |
|---|---|---|---|---|
| Sarin | 2-PAM | 0.3 ± 0.02 | 25 ± 7 | 11 |
| | HI-6 | 0.8 ± 0.06 | 57 ± 11 | 13 |
| | NM-139 | 0.18 ± 0.02 | 111 ± 22 | 1.6 |
| | NM-141 | 0.11 ± 0.002 | 45 ± 3 | 2.5 |
| | NM-143 | 0.1 ± 0.002 | 10 ± 1 | 10 |
| | NM-152 | 0 | 0 | 0 |
| Tabun | 2-PAM | 0.5 ± 0.2 | 211 ± 113 | 2 |
| | HI-6 | 0 | 0 | 0 |
| | NM-139 | 0 | 0 | 0 |
| | NM-141 | 0 | 0 | 0 |
| | NM-143 | 0 | 0 | 0 |
| | NM-152 | 0 | 0 | 0 |
| Paraoxon | 2-PAM | 0.07 ± 0.02 | 68 ± 16 | 1 |
| | HI-6 | 0.8 ± 0.06 | 290 ± 70 | 0.4 |
| | NM-139 | 0.6 ± 0.005 | 257 ± 45 | 2 |
| | NM-141 | 0.14 ± 0.005 | 6 ± 1 | 24 |
| | NM-143 | 0.3 ± 0.008 | 11 ± 2 | 27 |
| | NM-152 | 0 | 0 | 0 |

TABLE 3

IC50 for AChE of oximes: 2-PAM, HI6 and NMs

| Oxime | IC50 (μM) |
|---|---|
| 2-PAM | 580 ± 28 |
| HI-6 | 82 ± 6 |
| NM-55 | 57 ± 12 |
| NM-109 | 246 ± 28 |
| NM-130 | 590 ± 47 |
| NM-131 | 99 ± 12 |
| NM-132 | 133 ± 12 |
| NM-139 | 328 ± 30 |
| NM-141 | 114 ± 6 |
| NM-143 | 436 ± 22 |
| NM-152 | 1 ± 0.06 |
| NM-168 | 394 ± 33 |
| NM-171 | 398 ± 17 |
| NM-176 | 2 ± 0.01 |
| CV-05 | 437 ± 49 |
| NM-250 | 526 ± 25 |
| NM-261 | 375 ± 28 |

These results show that the compounds of the invention have a broad spectrum of reactivation of OPNA-inhibited AChE: particularly they show an increased efficacy for VX and paraoxon, and a good potency against sarin. In addition, we found that CV-05, NM-250 and NM-261 exhibited highly selective efficacy in reactivation VX-hAChE.

The invention claimed is:

1. Compound which is chosen from compounds of formula (I) and their pharmaceutically acceptable salts:

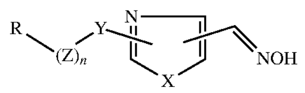

(I)

wherein:

X is O or S;

Y is $-CH_2-CH_2-$, or $-C\equiv C-$;

Z is $-CH_2-$, n is an integer from 0 to 4; and

R is an alkyl group, a hydroxyalkyl group, an alkyl group ended by a radical-$C(=O)-O-CH_3$, an aryl group, a heteroaryl group, a cycloalkyl group, or a group —N(R1) (R2), wherein R1 and R2 are each independently H, or heteroaryl.

2. Compound according to claim 1, which is a salt of a compound of formula (I) with an acid or a base.

3. Compound according to claim 1, wherein R is a heteroaryl group or a group —N(R1) (R2), wherein R1 and R2 are each independently H or a heteroaryl.

4. Compound according to claim 1, wherein the heteroaryl group is a pyridine group, or a quinoline group, or a pyrimidine group such.

5. Compound according to claim 1, wherein the compound is chosen from:

compounds of formula (II) and their pharmaceutically acceptable salts:

(II)

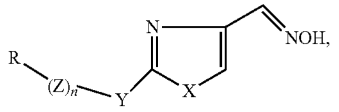

wherein X, Y, Z, n and R are as in claim 1;

compounds of formula (III) and their pharmaceutically acceptable salts:

(III)

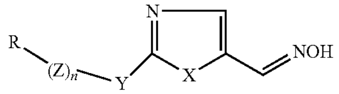

wherein X, Y, Z, n and R are as in claim 1;

compounds of formula (IV) and their pharmaceutically acceptable salts:

(IV)

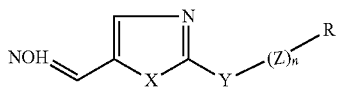

wherein X, Y, Z, n and R are as in claim 1; and compounds of formula (V) and their pharmaceutically acceptable salts:

(V)

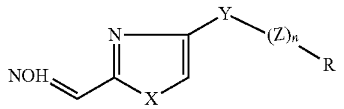

wherein X, Y, Z, n and R are as in claim 1.

6. Compound according to claim 5, wherein the compound is chosen from:

compounds of formula (II) and their pharmaceutically acceptable salts, wherein:

X is S;

Y is $—CH_2—CH_2—$ or —C≡C—, n is 0, 1 or 2; and

R is an alkyl, a hydroxyalkyl group, an alkyl group ended by a radical-C(=O)—O—$CH_3$, an aryl group, a heteroaryl group or a group —N(R1) (R2);

or R1 is H and R2 is a heteroaryl; or

X is O;

Y is $—CH_2—CH_2—$ or —C≡C—, n is 0, 1 or 2, and

R is a heteroaryl group;

compounds of formula (III) and their pharmaceutically acceptable salts, wherein:

X is S;

Y is $—CH_2—CH_2—$ or —C≡C—, n is 0, 1 or 2, and

R is a heteroaryl group or a group —N(R1) (R2), or R1 is H and R2 is a heteroaryl; or X is O;

Y is $—CH_2—CH_2—$ or —C≡C—, n is 0, 1 or 2, and

R is a heteroaryl group;

compounds of formula (IV) and their pharmaceutically acceptable salts, wherein:

X is S;

Y is $—CH_2—CH_2—$ or —C≡C—, n is 0, 1 or 2, and

R is a heteroaryl group; and compounds of formula (V) and their pharmaceutically acceptable salts, wherein:

X is S;

Y is $—CH_2—CH_2—$ or —C≡C—, n is 0, 1 or 2, and

R is an aryl group or a heteroaryl group.

7. A pharmaceutical composition comprising at least one compound of formula (I) according to claim 1, and at least one pharmaceutically acceptable support.

8. The compound according to claim 2, wherein the salt is a chlorhydrate salt.

9. The compound according to claim 4, wherein the pyridine group is 2-, 3- or 4-pyridino, the quinoline group is 4-quinolinyl, and the pyrimidine group is a pyrimidin-2-yl.

10. Compound according to claim 1, wherein the compound is chosen from:

NM-55

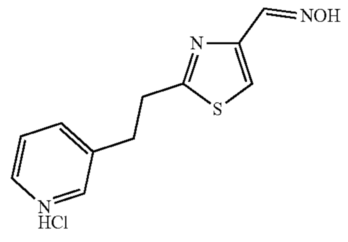

NM-131

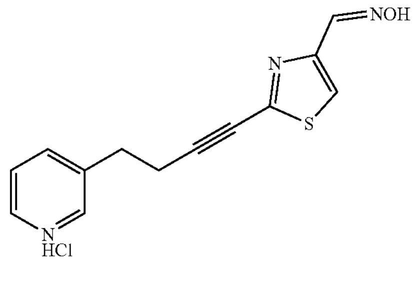

-continued
NM-132
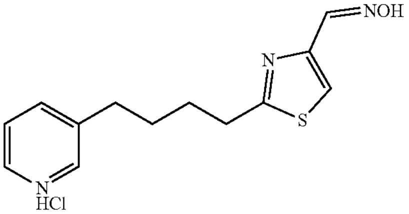
NM-109
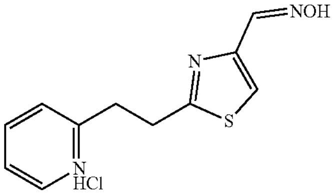
NM-130
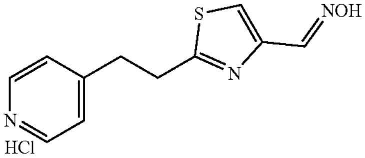
NM-46
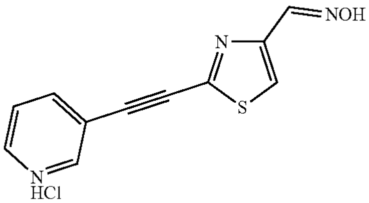
NM-176
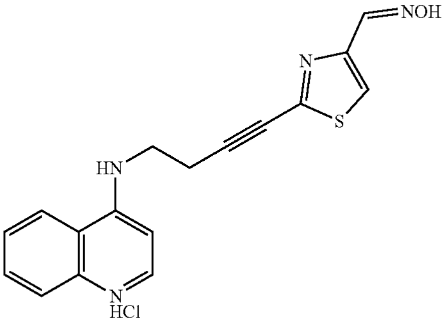
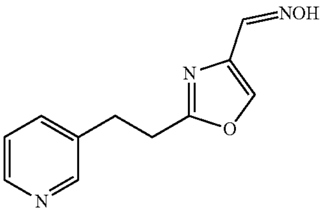
NM-139
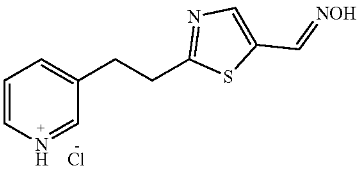
-continued
NM-141
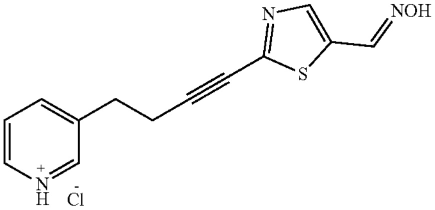
NM-143
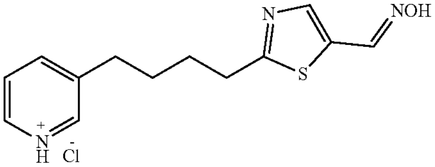
NM-152
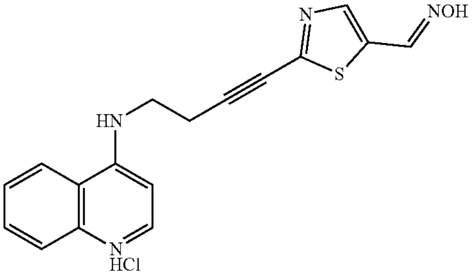
NM-168
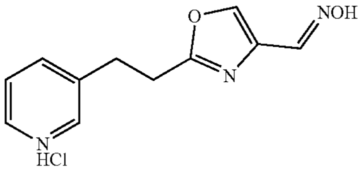
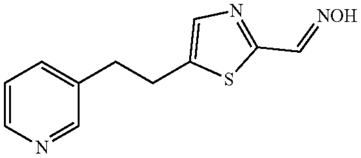
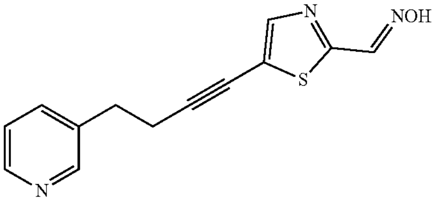
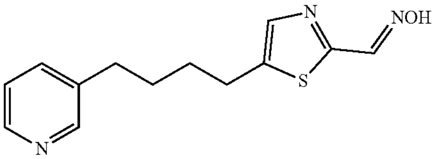
NM-171
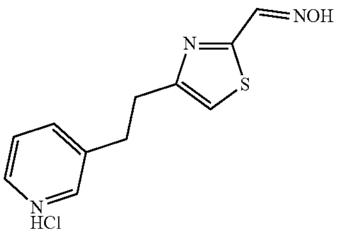

-continued
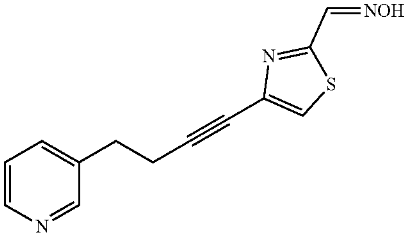
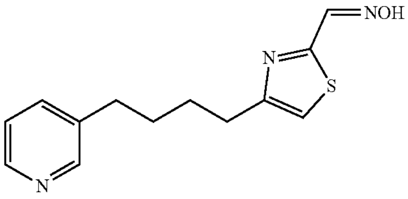
4
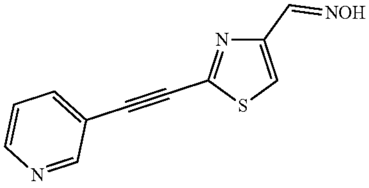
5
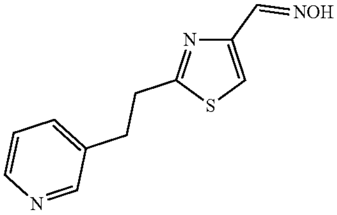
7
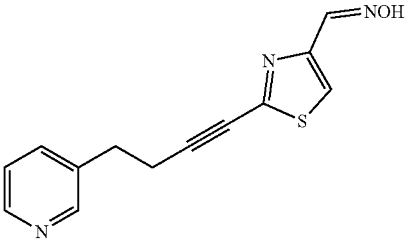
8
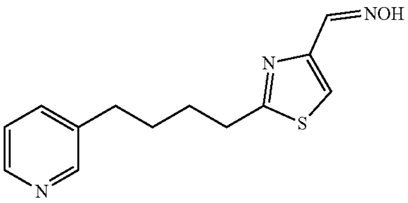
10
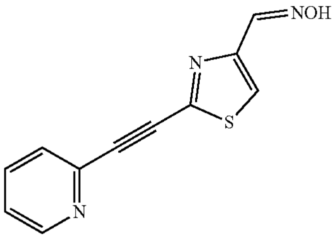
-continued
11
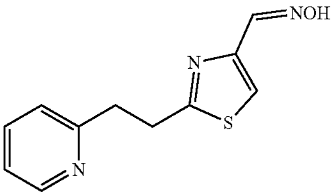
13
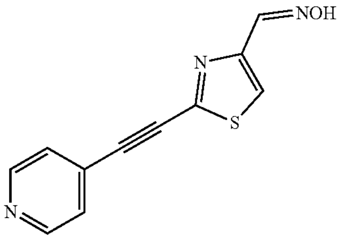
14
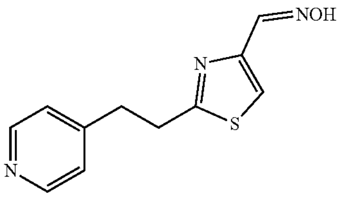
17
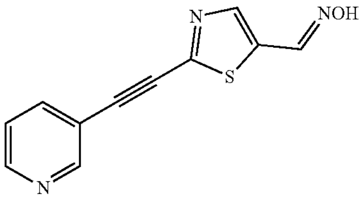
18
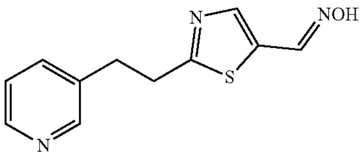
19
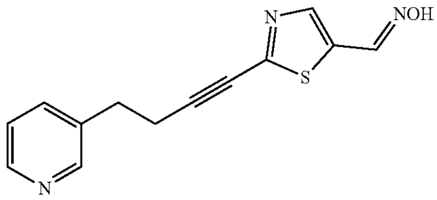
20
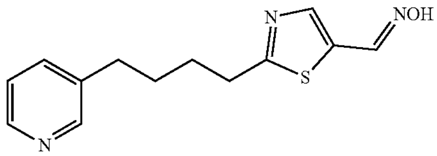

-continued
22
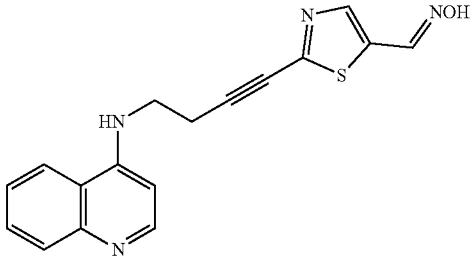
23
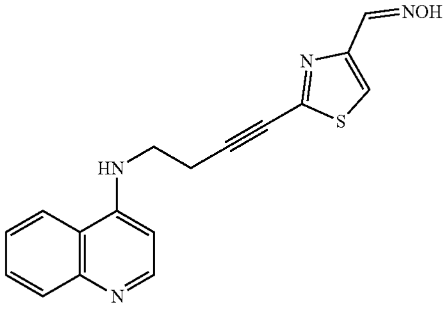
26
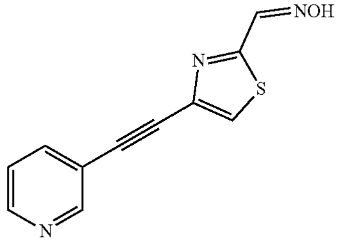
27
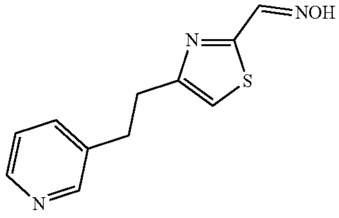
32
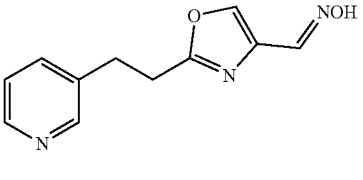
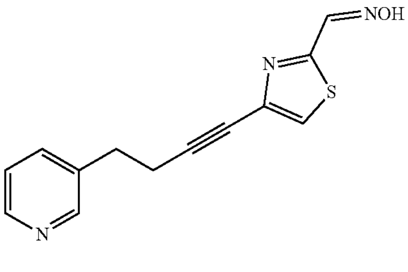
-continued
NM-259
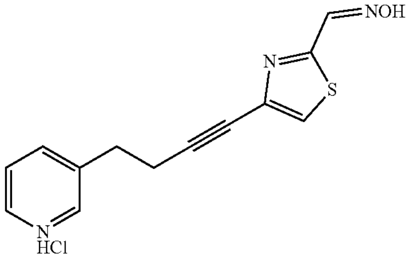
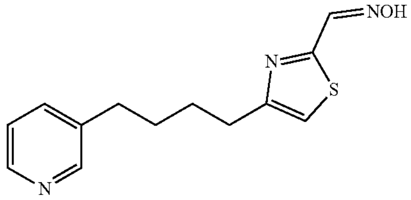
NM-260
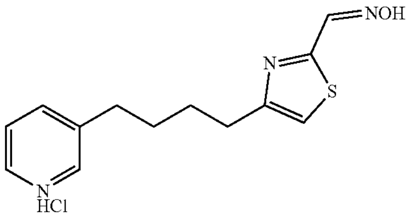
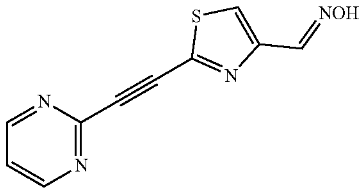
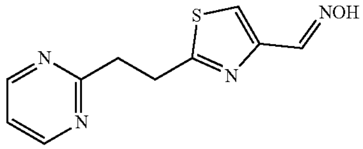
NM-250
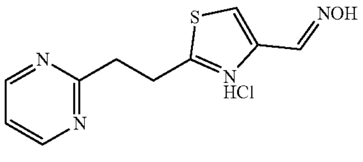
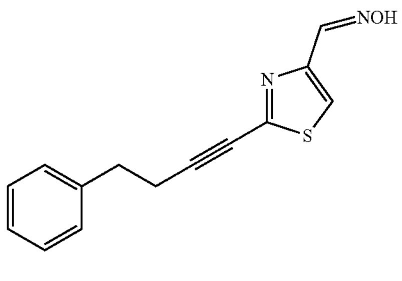

-continued
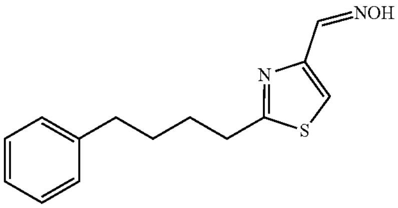
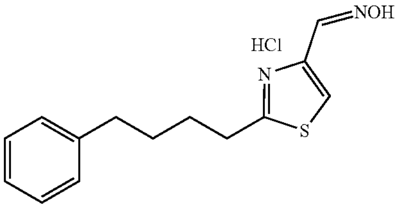
NM-247
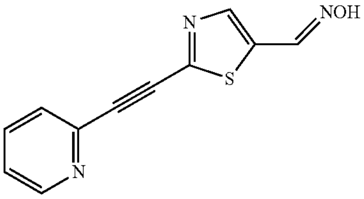
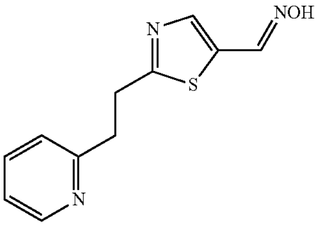
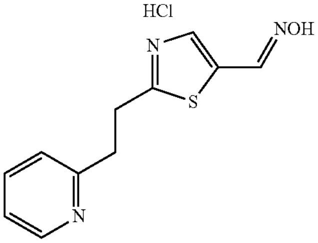
NM-204
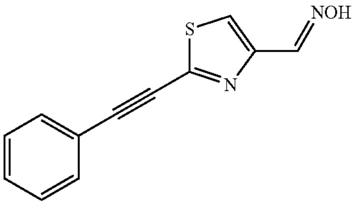
FR-72
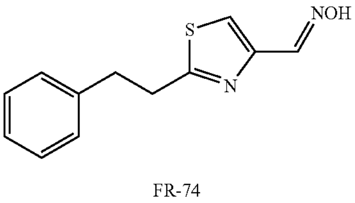
FR-74
-continued
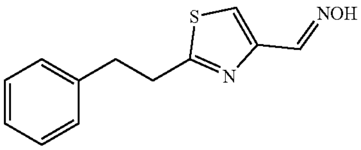
FR-78
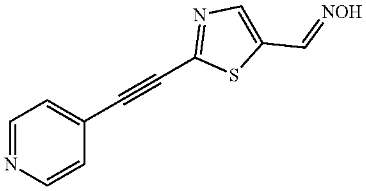
FR-73
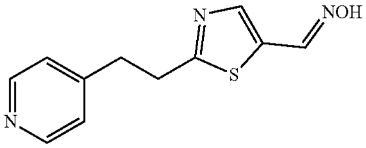
FR-77
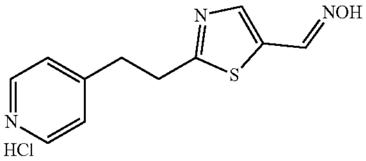
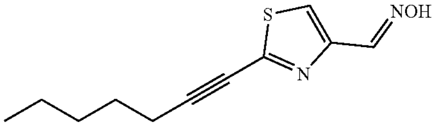
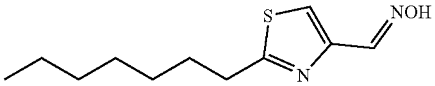
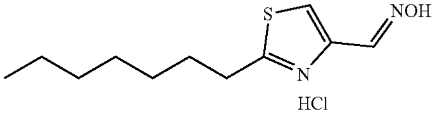
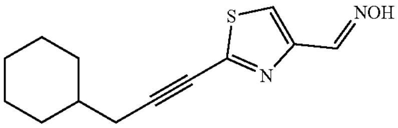
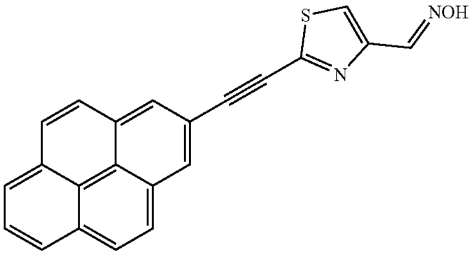
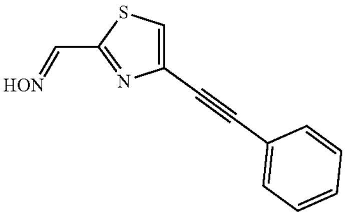

-continued
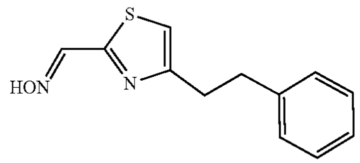
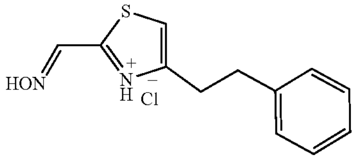
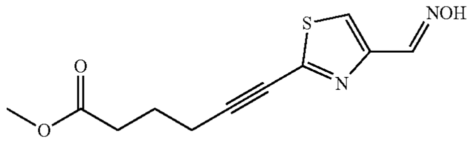
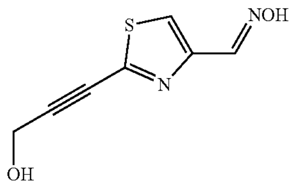
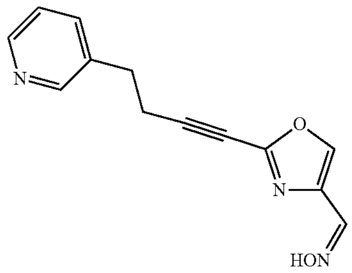
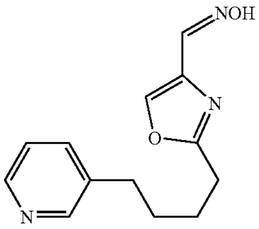
and
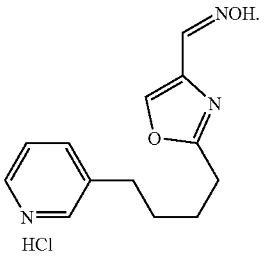
11. Compound according to claim 1, wherein the compound is chosen from:
NM-55
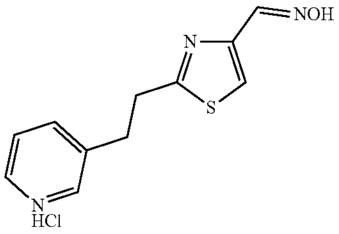
NM-131
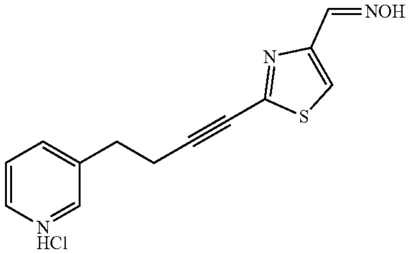
NM-132
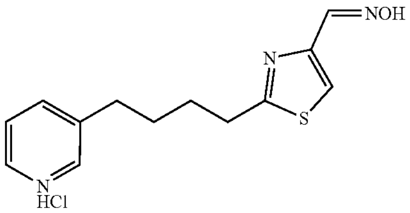
NM-109
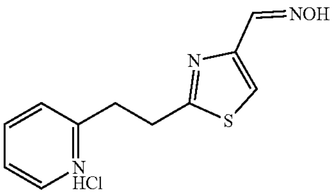
NM-130
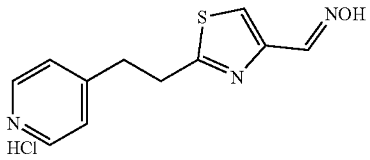
NM-46
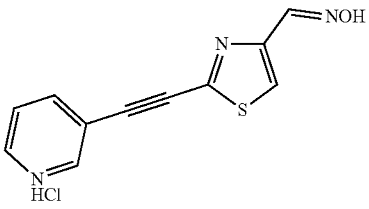
NM-176
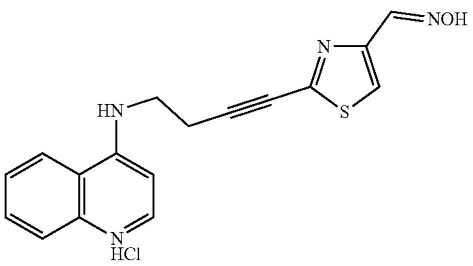

-continued
NM-139
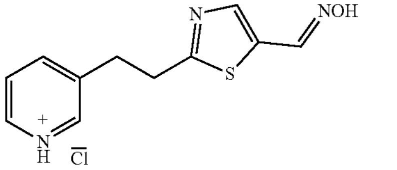
NM-141
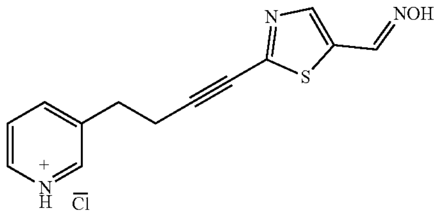
NM-143
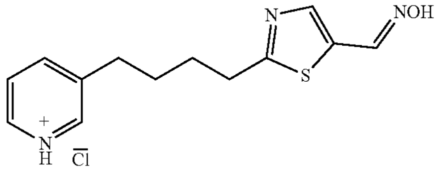
NM-152
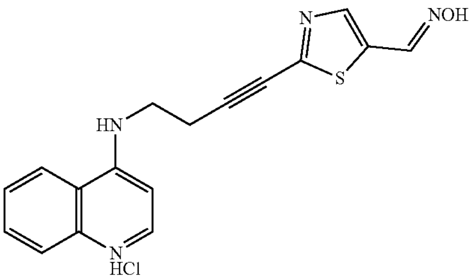
NM-168
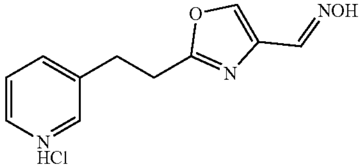
NM-171
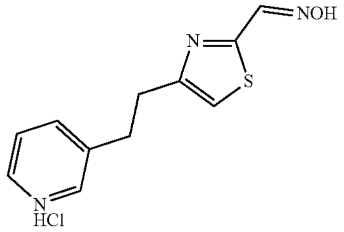
NM-259
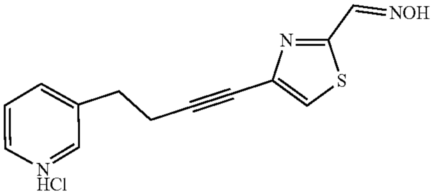
-continued
NM-261
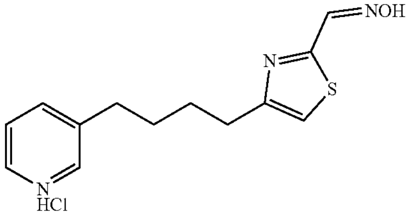
NM-250
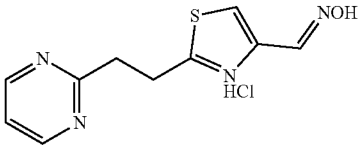
NM-247
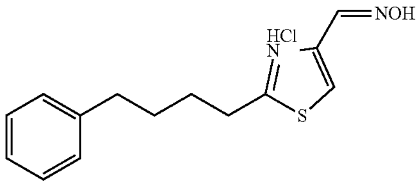
NM-204
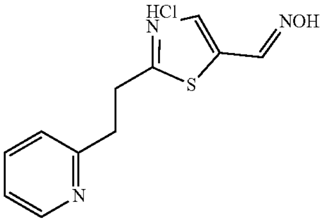
FR-78
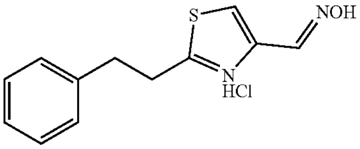
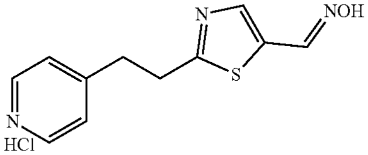
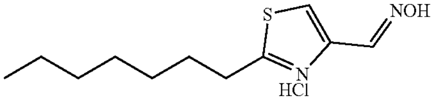
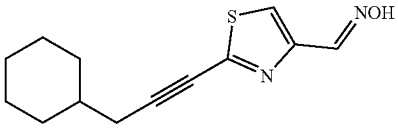
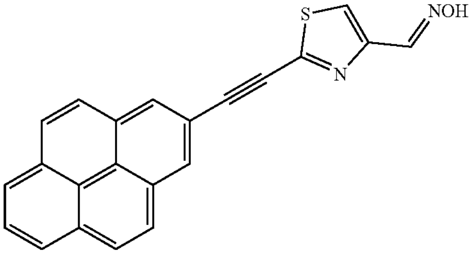

-continued
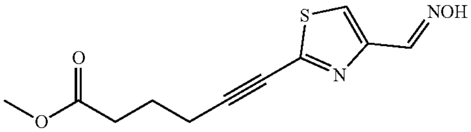
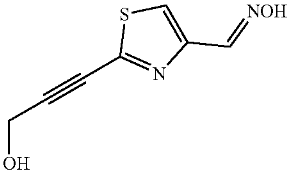
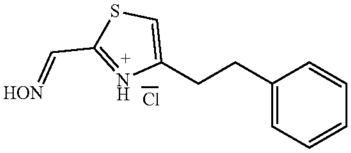
-continued
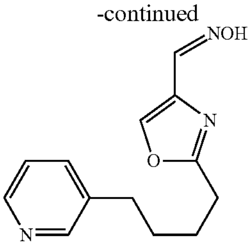
and
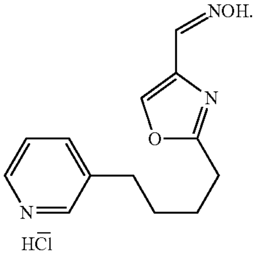
* * * * *